US008663921B2

(12) United States Patent
Mitchell et al.

(10) Patent No.: US 8,663,921 B2
(45) Date of Patent: *Mar. 4, 2014

(54) DETECTING FETAL CHROMOSOMAL ABNORMALITIES USING TANDEM SINGLE NUCLEOTIDE POLYMORPHISMS

(75) Inventors: Aoy Tomita Mitchell, Elm Grove, WI (US); Michael Mitchell, Elm Grove, WI (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/850,588

(22) Filed: Aug. 4, 2010

(65) Prior Publication Data

US 2011/0059451 A1 Mar. 10, 2011

Related U.S. Application Data

(63) Continuation of application No. 11/713,069, filed on Feb. 28, 2007, now Pat. No. 7,799,531.

(60) Provisional application No. 60/777,865, filed on Feb. 28, 2006.

(51) Int. Cl.
*C12Q 1/68* (2006.01)
*C12P 19/34* (2006.01)

(52) U.S. Cl.
USPC .......... 435/6.11; 435/6.1; 435/6.12; 435/91.2

(58) Field of Classification Search
None
See application file for complete search history.

(56) References Cited

U.S. PATENT DOCUMENTS

| | | | |
|---|---|---|---|
| 6,258,540 B1 | 7/2001 | Lo et al. | |
| 6,979,541 B1 | 12/2005 | Pont-Kingdon et al. | |
| 7,799,531 B2 * | 9/2010 | Mitchell et al. | 435/6.12 |
| 8,399,195 B2 * | 3/2013 | Mitchell et al. | 435/6.11 |
| 2001/0048756 A1 | 12/2001 | Staub et al. | |
| 2003/0082606 A1 | 5/2003 | Lebo et al. | |
| 2003/0211522 A1 | 11/2003 | Landes et al. | |
| 2004/0137452 A1 | 7/2004 | Levett et al. | |
| 2004/0137470 A1 | 7/2004 | Dhallan | |
| 2005/0049793 A1 | 3/2005 | Paterlini-Brechot | |
| 2005/0164241 A1 | 7/2005 | Hahn et al. | |
| 2005/0228172 A9 * | 10/2005 | Wang | 536/24.3 |
| 2006/0121452 A1 | 6/2006 | Dhallan | |
| 2006/0160105 A1 | 7/2006 | Dhallan | |
| 2007/0207466 A1 | 9/2007 | Cantor et al. | |
| 2008/0318235 A1 | 12/2008 | Handyside | |

FOREIGN PATENT DOCUMENTS

| | | |
|---|---|---|
| WO | WO 00/34652 | 6/2000 |
| WO | WO 02/068685 | 9/2002 |
| WO | WO 03/062441 | 7/2003 |
| WO | WO 2004/078999 | 9/2004 |
| WO | WO 2004/079011 | 9/2004 |
| WO | WO 2005/023091 | 3/2005 |
| WO | WO 2005/035725 | 4/2005 |
| WO | WO 2005/044086 | 5/2005 |
| WO | WO 2006/011738 | 2/2006 |
| WO | WO 2011/057094 A1 | 5/2011 |

OTHER PUBLICATIONS

Adams et al., "Microchimerism: an investigative frontier in autoimmunity and transplantation," *JAMA* 291(9):1127-1131 (2004).
Andonova et al., "Introduction of the QF-PCR analysis for the purposes of prenatal diagnosis in Bulgaria—estimation of applicability of 6 STR markers on chromosomes 21 and 18," *Prenat. Diagn.* 24(3):202-208 (2004).
André et al., "Fidelity and mutational spectrum of Pfu DNA polymerase on a human mitochondrial DNA sequence," *Genome Res.* 7(8):843-852 (1997).
Antonarakis et al., "Analysis of DNA haplotypes suggests a genetic predisposition to trisomy 21 associated with DNA sequences on chromosome 21," *Proc. Natl. Acad. Sci. U.S.A.* 82(10):3360-3364 (1985).
BBC News, Safer test for unborn babies hope. BBC News Oct. 4, 2005 http://news.bbc.co.uk/2/hi/health/4307628.stm.
Birch et al., "Accurate and robust quantification of circulating fetal and total DNA in maternal plasma from 5 to 41 weeks of gestation," *Clin. Chem.* 51(2):312-320 (2005).
Chim et al., "Detection of the placental epigenetic signature of the maspin gene in maternal plasma," *Proc. Natl. Acad. Sci. U.S.A.* 102(41):14753-14758 (2005).
Cline et al., "PCR fidelity of pfu DNA polymerase and other thermostable DNA polymerases," *Nucleic Acids Res.* 24(18):3546-3551 (1996).
Database SNP (Online) Retrieved from NCBI Database Accession No. rs2822654 Abstract (2004).
Dhallan et al., "A non-invasive test for prenatal diagnosis based on fetal DNA present in maternal blood: a preliminary study," www.thelancet.com 2007. DOI:10.1016/S0140-6736(07)60115-9.
Dhallan et al., "Methods to Increase the Percentage of Free Fetal DNA Recovered From the Maternal Circulation," *JAMA* 291(9):1114-1119 (2004).
Ding et al., "MS analysis of single-nucleotide differences in circulating nucleic acids: Application to noninvasive prenatal diagnosis," *Proc. Natl. Acad. Sci. U.S.A.* 101(29):10762-10767 (2004).
Howdy Database, Human Organized Whole Genome Database, Marker 5618, NM_003895, available via url: <howdy.jst.go.jp/HOWDYCL//HOWDY.pl?Cls=Marker&Key=UKEY&Val=5618>, Oct. 14, 2008.
Human Chromosome 21 cSNP database, University of Geneva. Swiss Institute of Bioinformatics, HC21S00131, available via url: <csnp.unige.ch/cgi-bin/csnp_fetch?db=csnp&format=html&entry=HC21G0062>, Oct. 14, 2008.
Human Chromosome 21 cSNP database, University of Geneva. Swiss Institute of Bioinformatics, HC21S00027, available via url: <csnp.unige.ch/cgi-bin/csnp_fetch?db=csnp&format=html&entry=HC21G00018>, Oct. 14, 2008.
Illanes et al., "Detection of cell-free fetal DNA in maternal urine," *Prenat. Diagn.* 26(13):1216-1218 (2006).
International Search Report for International Application No. PCT/US2007/005399 (2007).

(Continued)

*Primary Examiner* — Carla Myers
(74) *Attorney, Agent, or Firm* — Convergent Law Group LLP

(57) ABSTRACT

The invention provides tandem single nucleotide polymorphisms and methods for their use, for example, in diagnosing Down Syndrome.

9 Claims, 2 Drawing Sheets

(56) References Cited

OTHER PUBLICATIONS

Khrapko et al., "Constant denaturant capillary electrophoresis (CDCE): a high resolution approach to mutational analysis," *Nucleic Acids Res.* 22(3):364-369 (1994).

Lerman et al., "Computational simulation of DNA melting and its application to denaturing gradient gel electrophoresis," *Methods Enzymol.* 155:482-501 (1987).

Li et al., Detection of paternally inherited fetal point mutations for beta-thalassemia using size-fractionated cell-free DNA in maternal plasma, *JAMA* 293(7):843-849 (2005). Corr:JAMA, 2005 293(14): p. 1728.

Li et al., "Inability to detect cell free fetal DNA in the urine of normal pregnant women nor in those affected by preeclampsia associated HELLP syndrome," *J. Soc. Gynecol. Investig.* 10(8):503-508 (2003).

Li et al., "Size separation of circulatory DNA in maternal plasma permits ready detection of fetal DNA polymorphisms," *Clin. Chem.* 50(6):1002-1011 (2004).

Lim et al., "Combination of competitive quantitative PCR and constant-denaturant capillary electrophoresis for high-resolution detection and enumeration of microbial cells," *Appl. Environ. Microbiol.* 67(9):3897-3903 (2001).

Li-Sucholeiki et al., "A sensitive scanning technology for low frequency nuclear point mutations in human genomic DNA," *Nucleic Acids Res.* 28(9): E44 (2000).

Lo et al., "Free Fetal DNA in Maternal Circulation," *JAMA* 292(23):2835-2836 (2004).

Lo et al., "Increased fetal DNA concentrations in the plasma of pregnant women carrying fetuses with trisomy 21," *Clin. Chem.* 45(10):1747-1751 (1999).

Lo et al., "Quantitative analysis of fetal DNA in maternal plasma and serum: implications for noninvasive prenatal diagnosis," *Am. J. Hum. Genet.* 62(4):768-775 (1998).

Malone et al., "First-trimester sonographic screening for Down syndrome," *Obstet. Gynecol.* 102(5 Pt 1):1066-1079 (2003).

Nagy et al., "Rapid determination of trisomy 21 from amniotic fluid cells using single-nucleotide polymorphic loci," *Prenat. Diagn.* 25(12):1138-1141 (2005).

Parsons et al., "Genotypic selection methods for the direct analysis of point mutations," *Mutat. Res.* 387:97-121 (1997).

Pertl et al., "Detection of male and female fetal DNA in maternal plasma by multiplex fluorescent polymerase chain reaction amplification of short tandem repeats," *Hum. Genet.* 106:45-49 (2000).

Pont-Kingdon et al., "Direct molecular haplotyping by melting curve analysis of hybridization probes: beta 2-adrenergic receptor haplotypes as an example," *Nucleic Acids Res.* 33(10):e89 (2005).

Poon et al., "Differential DNA methylation between fetus and mother as a strategy for detecting fetal DNA in maternal plasma," *Clin. Chem.* 48(1):35-41 (2002).

Puers et al., "Identification of repeat sequence heterogeneity at the polymorphic short tandem repeat locus HUMTH01[AATG]n and reassignment of alleles in population analysis by using a locus-specific allelic ladder," *Am. J. Hum. Genet.* 53(4):953-958 (1993).

Samura et al., "Diagnosis of trisomy 21 in fetal nucleated erythrocytes from maternal blood by use of short tandem repeat sequences," *Clin. Chem.* 47(9):1622-1626 (2001).

Simpson et al., "Cell-free fetal DNA in maternal blood: evolving clinical applications," *JAMA* 291(9):1135-1137 (2004).

The EMBL-EBI Database, EBI Dbfetch, Accession No. AF239726, Mar. 22, 2000.

The International HapMap Consortium, "A haplotype map of the human genome," *Nature* 437:1299-1320 (2005).

The International HapMap Consortium, "The International HapMap Project," *Nature* 426:789-796 (2003).

Thompson et al., "Heteroduplexes in mixed-template amplifications: formation, consequence and elimination by 'reconditioning PCR'," *Nucleic Acids Res.* 30(9):2083-2088 (2002).

Thorisson et al., "The International HapMap Project Web site," *Genome Res.* 15:1592-1593 (2005).

Wald et al., "Antenatal screening for Down's syndrome with the quadruple test," *Lancet* 361(9360):835-836 (2003).

Zheng et al., "Origins of human mitochondrial point mutations as DNA polymerase gamma-mediated errors." *Mutat. Res.* 599(1-2):11-20 (2006).

Zhong et al. *Annals NY Acad. Sci.* 945:250-257 (2006).

\* cited by examiner

```
                              SEQUENCE LISTING

<160> NUMBER OF SEQ ID NOS: 357

<210> SEQ ID NO 1
<211> LENGTH: 127
<212> TYPE: DNA
<213> ORGANISM: Homo sapiens

<400> SEQUENCE: 1
aacaaatctt catcttggaa tagcctgtga gaatgcctaa tcatctacga atgttacttt        60
ggcaccatct actggacaga ttaaataaca accaactcac tgtggattag acctacttct      120
atttcag                                                                127

<210> SEQ ID NO 2
<211> LENGTH: 20
<212> TYPE: DNA
<213> ORGANISM: Homo sapiens

<400> SEQUENCE: 2
atagcctgtg agaatgccta                                                   20

<210> SEQ ID NO 3
<211> LENGTH: 20
<212> TYPE: DNA
<213> ORGANISM: Homo sapiens

<400> SEQUENCE: 3
atccacagtg agttggttgt                                                   20

<210> SEQ ID NO 4
<211> LENGTH: 84
<212> TYPE: DNA
<213> ORGANISM: Homo sapiens

<400> SEQUENCE: 4
ttcctggaaa acaaaagtat ttctttcata gcccagctag catgataaat cagcgagtca       60
gaattctagc tttgttgtaa ggtt                                              84

<210> SEQ ID NO 5
<211> LENGTH: 20
<212> TYPE: DNA
<213> ORGANISM: Homo sapiens

<400> SEQUENCE: 5
tcctggaaaa caaaagtatt                                                   20

<210> SEQ ID NO 6
<211> LENGTH: 21
<212> TYPE: DNA
<213> ORGANISM: Homo sapiens

<400> SEQUENCE: 6
aaccttacaa caaagctaga a                                                 21
```

<210> SEQ ID NO 7
<211> LENGTH: 71
<212> TYPE: DNA
<213> ORGANISM: Homo sapiens

<400> SEQUENCE: 7
cactaagcct tggggatcca gctgcttaag gactaagacc gtatctagct cctttagta      60 tttccacagc a                                                          71

<210> SEQ ID NO 8
<211> LENGTH: 20
<212> TYPE: DNA
<213> ORGANISM: Homo sapiens

<400> SEQUENCE: 8
actaagcctt ggggatccag                                                 20

<210> SEQ ID NO 9
<211> LENGTH: 21
<212> TYPE: DNA
<213> ORGANISM: Homo sapiens

<400> SEQUENCE: 9
tgctgtggaa atactaaaag g                                               21

<210> SEQ ID NO 10
<211> LENGTH: 155
<212> TYPE: DNA
<213> ORGANISM: Homo sapiens

<400> SEQUENCE: 10
tcctccagag gtaatcctgt gatcagcact aacaccacat accagcccctt tcatcagctt    60 gttggagaag catctttact tcccgccaag cagtgaccta gataccatct cacaccagtt   120
agaatcagga tcattaaaaa gtcaagaaaa aacag                               155

<210> SEQ ID NO 11
<211> LENGTH: 20
<212> TYPE: DNA
<213> ORGANISM: Homo sapiens

<400> SEQUENCE: 11
ctccagaggt aatcctgtga                                                 20

<210> SEQ ID NO 12
<211> LENGTH: 21
<212> TYPE: DNA
<213> ORGANISM: Homo sapiens

<400> SEQUENCE: 12
tggtgtgaga tggtatctag g                                               21

<210> SEQ ID NO 13
<211> LENGTH: 146
<212> TYPE: DNA
<213> ORGANISM: Homo sapiens

<400> SEQUENCE: 13
tccaagtata atccatgaat cttgtttaaa tatagatcaa ataaaccact ataccaaaaa     60
catcaaaaga caactgggta aatttttaa atgactagct atttgatgtt aaggaagtaa    120
tgttactctc ttatatacaa tttgaa                                         146

```
<210> SEQ ID NO 14
<211> LENGTH: 22
<212> TYPE: DNA
<213> ORGANISM: Homo sapiens

<400> SEQUENCE: 14
gtataatcca tgaatcttgt tt                                              22

<210> SEQ ID NO 15
<211> LENGTH: 22
<212> TYPE: DNA
<213> ORGANISM: Homo sapiens

<400> SEQUENCE: 15
ttcaaattgt atataagaga gt                                              22

<210> SEQ ID NO 16
<211> LENGTH: 132
<212> TYPE: DNA
<213> ORGANISM: Homo sapiens

<400> SEQUENCE: 16
atggaaccga aacttcaagt agtttcatac gtatcacatt gacagttttc tctaagtttt     60
ctggtcttat gactcgttgt tcattatta aaactgtgcc agtgtatgca tagggcttag     120 aaattttta at                                                         132

<210> SEQ ID NO 17
<211> LENGTH: 18
<212> TYPE: DNA
<213> ORGANISM: Homo sapiens

<400> SEQUENCE: 17
atggaaccga aacttcaa                                                   18

<210> SEQ ID NO 18
<211> LENGTH: 22
<212> TYPE: DNA
<213> ORGANISM: Homo sapiens

<400> SEQUENCE: 18
ttaataatga aacaacgagt ca                                              22

<210> SEQ ID NO 19
<211> LENGTH: 157
<212> TYPE: DNA
<213> ORGANISM: Homo sapiens

<400> SEQUENCE: 19
acaggatcct tcctgaagac accaccttgg ggagggtgaa ggataaagaa tttgatcaga     60
aatcaagggt ggtgagatac atgttaagga tgaataaact ggccttttag gattcttgct    120
aaaattagac aatgcagagg caaccacaga gtccaag                             157

<210> SEQ ID NO 20
<211> LENGTH: 19
<212> TYPE: DNA
<213> ORGANISM: Homo sapiens

<400> SEQUENCE: 20
ttcctgaaga caccacctt                                                  19
```

<210> SEQ ID NO 21
<211> LENGTH: 18
<212> TYPE: DNA
<213> ORGANISM: Homo sapiens

<400> SEQUENCE: 21
cttggactct gtggttgc                                                    18

<210> SEQ ID NO 22
<211> LENGTH: 173
<212> TYPE: DNA
<213> ORGANISM: Homo sapiens

<400> SEQUENCE: 22
aatttccatt aaatcttgtt cgttgcttta ctgaggcact gaagttacca atgttccact      60
ggttgacctg cggggctatc tctaggttat gttactccag aaaatgaatt gtgtataaaa     120
gaggccttgg aggaaggcgt tttattcaca tcagttgttt tgcacattgc tta            173

<210> SEQ ID NO 23
<211> LENGTH: 20
<212> TYPE: DNA
<213> ORGANISM: Homo sapiens

<400> SEQUENCE: 23
actgaggcac tgaagttacc                                                  20

<210> SEQ ID NO 24
<211> LENGTH: 20
<212> TYPE: DNA
<213> ORGANISM: Homo sapiens

<400> SEQUENCE: 24
taagcaatgt gcaaaacaac                                                  20

<210> SEQ ID NO 25
<211> LENGTH: 191
<212> TYPE: DNA
<213> ORGANISM: Homo sapiens

<400> SEQUENCE: 25
tcggtttcag caggaaagtt attttttaata acttccctgt atttcttggt ttcagttatt     60
aattaactca ttaatgctaa actttgtgat cctaggttaa aaaacatatt caagatagct    120
tcagaatgtt tggtatacaa gtaggtctgg ctaaatataa gtgttagctt tctcaagcat    180
ctaaatgctg g                                                          191

<210> SEQ ID NO 26
<211> LENGTH: 20
<212> TYPE: DNA
<213> ORGANISM: Homo sapiens

<400> SEQUENCE: 26
gcaggaaagt tatttttaat                                                  20

<210> SEQ ID NO 27
<211> LENGTH: 21
<212> TYPE: DNA
<213> ORGANISM: Homo sapiens

<400> SEQUENCE: 27
tgcttgagaa agctaacact t                                                21

```
<210> SEQ ID NO 28
<211> LENGTH: 166
<212> TYPE: DNA
<213> ORGANISM: Homo sapiens

<400> SEQUENCE: 28
aagttatttt taataacttc cctgtatttc ttggtttcag ttattaatta actcattaat      60
gctaaacttt gtgatcctag gttaaaaaac atattcaaga tagcttcaga atgtttggta     120
tacaagtagg tctggctaaa tataagtgtt agctttctca agcatc                    166

<210> SEQ ID NO 29
<211> LENGTH: 20
<212> TYPE: DNA
<213> ORGANISM: Homo sapiens

<400> SEQUENCE: 29 attttaata acttccctgt                                                   20

<210> SEQ ID NO 30
<211> LENGTH: 20
<212> TYPE: DNA
<213> ORGANISM: Homo sapiens

<400> SEQUENCE: 30
cacttatatt tagccagacc                                                  20

<210> SEQ ID NO 31
<211> LENGTH: 152
<212> TYPE: DNA
<213> ORGANISM: Homo sapiens

<400> SEQUENCE: 31
attcattgtg tagaaagtgc ctgactcagt gtttggaaat tgtctgactt ttcctcatat      60
atagtgtggt ttcatgttat tgtatataag aactgacatg aactctgttt acaataatct     120
cccagtgcca taaagaccat aataaataat at                                   152

<210> SEQ ID NO 32
<211> LENGTH: 20
<212> TYPE: DNA
<213> ORGANISM: Homo sapiens

<400> SEQUENCE: 32
cagtgtttgg aaattgtctg                                                  20

<210> SEQ ID NO 33
<211> LENGTH: 20
<212> TYPE: DNA
<213> ORGANISM: Homo sapiens

<400> SEQUENCE: 33
ggcactggga gattattgta                                                  20

<210> SEQ ID NO 34
<211> LENGTH: 163
<212> TYPE: DNA
<213> ORGANISM: Homo sapiens

<400> SEQUENCE: 34
cactgggtcc tgttgttaag tacacataat accacacagg agaaaatcag gctaattgta      60
aatgggcaac ctactaatt gtttcattaa aaagcataca gattcatttt acactatagc      120
tagtcttgtt tgttttttta ttttgcaaaa gtaattacgg ccc                       163
```

```
<210> SEQ ID NO 35
<211> LENGTH: 20
<212> TYPE: DNA
<213> ORGANISM: Homo sapiens

<400> SEQUENCE: 35
tcctgttgtt aagtacacat                                              20

<210> SEQ ID NO 36
<211> LENGTH: 18
<212> TYPE: DNA
<213> ORGANISM: Homo sapiens

<400> SEQUENCE: 36
gggccgtaat tacttttg                                                18

<210> SEQ ID NO 37
<211> LENGTH: 108
<212> TYPE: DNA
<213> ORGANISM: Homo sapiens

<400> SEQUENCE: 37
ctactcagta ggcactttgt gtctagaaac ttctgtgtca acggttttcc ctctctctgg   60
aattcatcag gacagaagtg attggtgtgg tggaagaggg ttgtgsta              108

<210> SEQ ID NO 38
<211> LENGTH: 21
<212> TYPE: DNA
<213> ORGANISM: Homo sapiens

<400> SEQUENCE: 38
actcagtagg cactttgtgt c                                            21

<210> SEQ ID NO 39
<211> LENGTH: 18
<212> TYPE: DNA
<213> ORGANISM: Homo sapiens

<400> SEQUENCE: 39
tcttccacca caccaatc                                                18

<210> SEQ ID NO 40
<211> LENGTH: 144
<212> TYPE: DNA
<213> ORGANISM: Homo sapiens

<400> SEQUENCE: 40
tggcttttca aaggtaaaat ttactaagtg tattaatatt ttaccaattt ccagccagga   60
gagtatgaat gttgcattat tacattgctt tgaaacaaag cattagtctt aattcagaag  120
tttaaattca gatgttaacg ttgc                                        144

<210> SEQ ID NO 41
<211> LENGTH: 19
<212> TYPE: DNA
<213> ORGANISM: Homo sapiens

<400> SEQUENCE: 41
tggcttttca aaggtaaaa                                               19

<210> SEQ ID NO 42
<211> LENGTH: 21
```

```
<212> TYPE: DNA
<213> ORGANISM: Homo sapiens

<400> SEQUENCE: 42
gcaacgttaa catctgaatt t                                              21

<210> SEQ ID NO 43
<211> LENGTH: 110
<212> TYPE: DNA
<213> ORGANISM: Homo sapiens

<400> SEQUENCE: 43
taagtattga agaaaggaga atttaaatta cttcatatac ctgataaagg aaaacatata    60
caaggcaaat aaacatctta gatcatgaca tataaaataa tagattatta              110

<210> SEQ ID NO 44
<211> LENGTH: 20
<212> TYPE: DNA
<213> ORGANISM: Homo sapiens

<400> SEQUENCE: 44
ttgaagaaag gagaatttaa                                                20

<210> SEQ ID NO 45
<211> LENGTH: 22
<212> TYPE: DNA
<213> ORGANISM: Homo sapiens

<400> SEQUENCE: 45
attttatatg tcatgatcta ag                                             22

<210> SEQ ID NO 46
<211> LENGTH: 165
<212> TYPE: DNA
<213> ORGANISM: Homo sapiens

<400> SEQUENCE: 46
tgcagagatt acaggtgtga gccaccgtgc ccagcctcat aaccgtttca actacttttt    60
cacttgacaa gcagatgtga agttaacaaa gtcacccata tttgaaataa agatagtata   120
ttcctggggt aggcagaggc agttgaggat catgaaataa ctatg                   165

<210> SEQ ID NO 47
<211> LENGTH: 19
<212> TYPE: DNA
<213> ORGANISM: Homo sapiens

<400> SEQUENCE: 47
agagattaca ggtgtgagc                                                 19

<210> SEQ ID NO 48
<211> LENGTH: 19
<212> TYPE: DNA
<213> ORGANISM: Homo sapiens

<400> SEQUENCE: 48
atgatcctca actgcctct                                                 19

<210> SEQ ID NO 49
<211> LENGTH: 178
<212> TYPE: DNA
<213> ORGANISM: Homo sapiens

<400> SEQUENCE: 49
```

```
tgcaatgaaa ctcaaaagag aaaagttaac aggtgcaaaa ggtagtttta ttataaaagg      60
agggtaggca acaagaatat gtttaatttt tcttcctttt catgagtaag gacaagagtg     120
tcatatatgt gaatatttt atttaatttt aagtagaaat ctgtttttaa aatatggg       178
```

<210> SEQ ID NO 50
<211> LENGTH: 20
<212> TYPE: DNA
<213> ORGANISM: Homo sapiens

<400> SEQUENCE: 50

```
tgaaactcaa aagagaaaag                                                  20
```

<210> SEQ ID NO 51
<211> LENGTH: 20
<212> TYPE: DNA
<213> ORGANISM: Homo sapiens

<400> SEQUENCE: 51

```
acagatttct acttaaaatt                                                  20
```

<210> SEQ ID NO 52
<211> LENGTH: 102
<212> TYPE: DNA
<213> ORGANISM: Homo sapiens

<400> SEQUENCE: 52

```
ccaccattca tcaaaacttt gatactggac tcaattgtga atttgacttg aaatttgata     60
atgcttttgt tttactgttc tgctcagcaa aatagtacat gt                       102
```

<210> SEQ ID NO 53
<211> LENGTH: 20
<212> TYPE: DNA
<213> ORGANISM: Homo sapiens

<400> SEQUENCE: 53

```
caaaactttg atactggact                                                  20
```

<210> SEQ ID NO 54
<211> LENGTH: 19
<212> TYPE: DNA
<213> ORGANISM: Homo sapiens

<400> SEQUENCE: 54

```
acatgtacta ttttgctga                                                   19
```

<210> SEQ ID NO 55
<211> LENGTH: 166
<212> TYPE: DNA
<213> ORGANISM: Homo sapiens

<400> SEQUENCE: 55

```
gcctgcataa agtgaggatg gtgtagtaat tgggtatctc cagttataaa cacaaaaagc     60
atgatagagc tgggactgtg attgcaggaa agcaatagtc actccaaaag gagatcctca    120
tgatatgaat acggaagaaa caatatttcc tgctaatgta gtagcc                    166
```

<210> SEQ ID NO 56
<211> LENGTH: 20
<212> TYPE: DNA
<213> ORGANISM: Homo sapiens

<400> SEQUENCE: 56
cctgcataaa gtgaggatgg                                                    20

<210> SEQ ID NO 57
<211> LENGTH: 21
<212> TYPE: DNA
<213> ORGANISM: Homo sapiens

<400> SEQUENCE: 57
tgaggatctc cttttggagt g                                                  21

<210> SEQ ID NO 58
<211> LENGTH: 154
<212> TYPE: DNA
<213> ORGANISM: Homo sapiens

<400> SEQUENCE: 58 gcaaagggt actctatgta atgaacatga cctggcagta ctgacatctc ctgagggact         60
gttagaagtg cagactcttg tatcttttct caagtctatg aaatctagac ttcattttaa       120
caagatgacc cgatatttac atacacatta aagt                                   154

<210> SEQ ID NO 59
<211> LENGTH: 20
<212> TYPE: DNA
<213> ORGANISM: Homo sapiens

<400> SEQUENCE: 59 gcaaagggt actctatgta                                                     20

<210> SEQ ID NO 60
<211> LENGTH: 20
<212> TYPE: DNA
<213> ORGANISM: Homo sapiens

<400> SEQUENCE: 60
tatcgggtca tcttgttaaa                                                    20

<210> SEQ ID NO 61
<211> LENGTH: 174
<212> TYPE: DNA
<213> ORGANISM: Homo sapiens

<400> SEQUENCE: 61
gtatctaaca aagctctgtc caaaattttg aatttctcgt taaaagcatc atgattatag        60
aacagaggtt acaatcaatt attcagtcac acaatcactc tcatcagtca ttaaggtgcg      120
tacctggtgt tccagttatt cagtgtggta taacaaacta cctggaactt aatg            174

<210> SEQ ID NO 62
<211> LENGTH: 22
<212> TYPE: DNA
<213> ORGANISM: Homo sapiens

<400> SEQUENCE: 62
tctaacaaag ctctgtccaa aa                                                 22

<210> SEQ ID NO 63
<211> LENGTH: 21
<212> TYPE: DNA
<213> ORGANISM: Homo sapiens

<400> SEQUENCE: 63
ccacactgaa taactggaac a                                                  21

<210> SEQ ID NO 64
<211> LENGTH: 202
<212> TYPE: DNA
<213> ORGANISM: Homo sapiens

<400> SEQUENCE: 64

```
agagtggtta agtgacttga tcaattcctc aggtggggat tcaagctctt aaagctgtag      60
actatgtcgt ccaaacaaac actgacatga atatgacttc caataggcaa gaaaagaggc     120
ctaggtcgag atactgcaag acatgcaagc aatctagtaa tggcataaaa cctgctatcc     180
gaattggcta aaattatgta tt                                              202
```

<210> SEQ ID NO 65
<211> LENGTH: 20
<212> TYPE: DNA
<213> ORGANISM: Homo sapiens

<400> SEQUENCE: 65

```
ggtggggatt caagctctta                                                  20
```

<210> SEQ ID NO 66
<211> LENGTH: 22
<212> TYPE: DNA
<213> ORGANISM: Homo sapiens

<400> SEQUENCE: 66

```
ggatagcagg ttttatgcca tt                                               22
```

<210> SEQ ID NO 67
<211> LENGTH: 156
<212> TYPE: DNA
<213> ORGANISM: Homo sapiens

<400> SEQUENCE: 67

```
ttctttctca cacaatgggt tccattccca ctactactcc attcaaattg aagtgccttc      60
aatgattatt aaaaaactct ctttaaaata gctcacgtaa ccttacatcc tttgactgag     120
gctcaactca tgtcaatgct tcagtatcaa cttttc                               156
```

<210> SEQ ID NO 68
<211> LENGTH: 21
<212> TYPE: DNA
<213> ORGANISM: Homo sapiens

<400> SEQUENCE: 68

```
aatgggttcc attcccacta c                                                21
```

<210> SEQ ID NO 69
<211> LENGTH: 20
<212> TYPE: DNA
<213> ORGANISM: Homo sapiens

<400> SEQUENCE: 69

```
tgagcctcag tcaaaggatg                                                  20
```

<210> SEQ ID NO 70
<211> LENGTH: 202
<212> TYPE: DNA
<213> ORGANISM: Homo sapiens

<400> SEQUENCE: 70

```
atttgtaata acatttagta agtatttatt tgaggagttt gaattttgtt cttgtttatc      60
```

```
ttgttctctt tcttcgtaga ttagttggtg ttaacatcaa taggataacc ctttctttca      120
gcatatgtga atgaaataaa ccaattattg ccactttcca ggttaaccag aatatacata      180
gatacgagga cagtggactg tt                                               202
```

<210> SEQ ID NO 71
<211> LENGTH: 22
<212> TYPE: DNA
<213> ORGANISM: Homo sapiens

<400> SEQUENCE: 71

```
ttgaggagtt tgaattttgt tc                                                22
```

<210> SEQ ID NO 72
<211> LENGTH: 20
<212> TYPE: DNA
<213> ORGANISM: Homo sapiens

<400> SEQUENCE: 72

```
aacctggaaa gtggcaataa                                                   20
```

<210> SEQ ID NO 73
<211> LENGTH: 171
<212> TYPE: DNA
<213> ORGANISM: Homo sapiens

<400> SEQUENCE: 73

```
tagggcagag agagcaagca agctctctac cttctcatat aagggcacta atcccaccat       60
gaaggcgcca ctgtcatgac ctgattatgt cacaaagacc ccggggcaaa tattaccact      120
gtgaggagta cagttttagc atgtgaattt tggaagaaca caaacattta g              171
```

<210> SEQ ID NO 74
<211> LENGTH: 21
<212> TYPE: DNA
<213> ORGANISM: Homo sapiens

<400> SEQUENCE: 74

```
gcaagcaagc tctctacctt c                                                 21
```

<210> SEQ ID NO 75
<211> LENGTH: 22
<212> TYPE: DNA
<213> ORGANISM: Homo sapiens

<400> SEQUENCE: 75

```
tgttcttcca aaattcacat gc                                                22
```

<210> SEQ ID NO 76
<211> LENGTH: 195
<212> TYPE: DNA
<213> ORGANISM: Homo sapiens

<400> SEQUENCE: 76

```
attctaattt taaatatcat tgatgtagaa cattctattt cactattcct tcattttatt       60
attatgggaa attatataca gttctccaga ttttttaaagc cttgctaaca tgttttaagt     120
cacacaaata ttctcctgtg ggaaaatgac agtaatttag tgtgcaacaa ttatatagaa      180
ctatttttca aactt                                                       195
```

<210> SEQ ID NO 77
<211> LENGTH: 21

-continued

```
<212> TYPE: DNA
<213> ORGANISM: Homo sapiens

<400> SEQUENCE: 77
atttcactat tccttcattt t                                              21

<210> SEQ ID NO 78
<211> LENGTH: 22
<212> TYPE: DNA
<213> ORGANISM: Homo sapiens

<400> SEQUENCE: 78
taattgttgc acactaaatt ac                                             22

<210> SEQ ID NO 79
<211> LENGTH: 138
<212> TYPE: DNA
<213> ORGANISM: Homo sapiens

<400> SEQUENCE: 79
actgtcatgg acttaaacaa ttgtctttga attgtctttt ttcatacttt tatttgcatc    60
tttccactaa aaagatggca caaagtaatc ctagtttaca ttttttacca tgtaattcca   120 tattacttttt tcctgaaa                                                138

<210> SEQ ID NO 80
<211> LENGTH: 20
<212> TYPE: DNA
<213> ORGANISM: Homo sapiens

<400> SEQUENCE: 80
actgtcatgg acttaaacaa                                                20

<210> SEQ ID NO 81
<211> LENGTH: 22
<212> TYPE: DNA
<213> ORGANISM: Homo sapiens

<400> SEQUENCE: 81
ttcaggaaaa agtaatatgg aa                                             22

<210> SEQ ID NO 82
<211> LENGTH: 119
<212> TYPE: DNA
<213> ORGANISM: Homo sapiens

<400> SEQUENCE: 82
aaagaaaaaa aagccacaga aatcagtcct agagaaaacc gatctatgag ctgcctgaaa    60
ataattataa aataactatc ataaaaatgc ccagtgagat ataagaaaac acagacaac    119

<210> SEQ ID NO 83
<211> LENGTH: 21
<212> TYPE: DNA
<213> ORGANISM: Homo sapiens

<400> SEQUENCE: 83
aaaaagccac agaaatcagt c                                              21

<210> SEQ ID NO 84
<211> LENGTH: 22
<212> TYPE: DNA
<213> ORGANISM: Homo sapiens

<400> SEQUENCE: 84
```

-continued ttcttatatc tcactgggca tt                                                22

<210> SEQ ID NO 85
<211> LENGTH: 143
<212> TYPE: DNA
<213> ORGANISM: Homo sapiens

<400> SEQUENCE: 85
caaggtcaga gaagttatct tggatggtag aagagaagaa aggagaagaa aggataagca      60
gaaaatcaaa aagggcataa aaaaattact ggggaaaata attcttagtc actcaccatt    120
tcttatgttt gtgaaaacag aaa                                            143

<210> SEQ ID NO 86
<211> LENGTH: 22
<212> TYPE: DNA
<213> ORGANISM: Homo sapiens

<400> SEQUENCE: 86
ggatggtaga agagaagaaa gg                                                22

<210> SEQ ID NO 87
<211> LENGTH: 22
<212> TYPE: DNA
<213> ORGANISM: Homo sapiens

<400> SEQUENCE: 87
tcacaaacat aagaaatggt ga                                                22

<210> SEQ ID NO 88
<211> LENGTH: 136
<212> TYPE: DNA
<213> ORGANISM: Homo sapiens

<400> SEQUENCE: 88
gaccacaatt cacaaatgca aagatgcaga accaacctaa gtggccactg actaatgaga      60
ggataaagaa gatgtggcat atatatatca gggactacta ctcagccatt acaaggaaca    120
aaataatgtc ttttgc                                                    136

<210> SEQ ID NO 89
<211> LENGTH: 20
<212> TYPE: DNA
<213> ORGANISM: Homo sapiens

<400> SEQUENCE: 89
tgcaaagatg cagaaccaac                                                   20

<210> SEQ ID NO 90
<211> LENGTH: 22
<212> TYPE: DNA
<213> ORGANISM: Homo sapiens

<400> SEQUENCE: 90
ttttgttcct tgtaatggct ga                                                22

<210> SEQ ID NO 91
<211> LENGTH: 160
<212> TYPE: DNA
<213> ORGANISM: Homo sapiens

<400> SEQUENCE: 91
gaccacaatt cacaaatgca aagatgcaga accaacctaa gtggccactg actaatgaga      60

```
ggataaagaa gatgtggcat atatacatca gggactactt ctcagccatt acaaggaaca    120
aaataatgtc ttttgcaaca acttggatag agctggaggc                          160

<210> SEQ ID NO 92
<211> LENGTH: 20
<212> TYPE: DNA
<213> ORGANISM: Homo sapiens

<400> SEQUENCE: 92
tgcaaagatg cagaaccaac                                                 20

<210> SEQ ID NO 93
<211> LENGTH: 21
<212> TYPE: DNA
<213> ORGANISM: Homo sapiens

<400> SEQUENCE: 93
gcctccagct ctatccaagt t                                               21

<210> SEQ ID NO 94
<211> LENGTH: 160
<212> TYPE: DNA
<213> ORGANISM: Homo sapiens

<400> SEQUENCE: 94
aatcctagac cttggattgc aagagactcc ttaatatctt cccatgtcca catttccttc     60
acatagtttg aatgtggctt ctattatata cagatacaag attcaaatcc aacctctatg    120
atgactggtc ttgtgaataa gcagaagagg cactaacaat                          160

<210> SEQ ID NO 95
<211> LENGTH: 22
<212> TYPE: DNA
<213> ORGANISM: Homo sapiens

<400> SEQUENCE: 95
ccttaatatc ttcccatgtc ca                                              22

<210> SEQ ID NO 96
<211> LENGTH: 22
<212> TYPE: DNA
<213> ORGANISM: Homo sapiens

<400> SEQUENCE: 96
attgttagtg cctcttctgc tt                                              22

<210> SEQ ID NO 97
<211> LENGTH: 162
<212> TYPE: DNA
<213> ORGANISM: Homo sapiens

<400> SEQUENCE: 97
aagagaagtg aggtcagcag ctgcaagcca cctccgtcat ttagaaaagc ttcatgatgt     60
agtgtgtcgt ttcgatgtga cactgtctca cagagttaaa atgatgttaa ggaactgttc   120
aatggaaatt tagaaatttc tcttttctc aattttagtg ta                        162

<210> SEQ ID NO 98
<211> LENGTH: 20
<212> TYPE: DNA
<213> ORGANISM: Homo sapiens

<400> SEQUENCE: 98
```

```
gagaagtgag gtcagcagct                                                   20

<210> SEQ ID NO 99
<211> LENGTH: 22
<212> TYPE: DNA
<213> ORGANISM: Homo sapiens

<400> SEQUENCE: 99
tttctaaatt tccattgaac ag                                                22

<210> SEQ ID NO 100
<211> LENGTH: 160
<212> TYPE: DNA
<213> ORGANISM: Homo sapiens

<400> SEQUENCE: 100
atggctgaat agtattccct tgtgtatata tctatttatc cttttattca ttgatggaca      60
cttaggctga ttttctctct tctcatggct ggcttctcat cacccttttgg tcctcctgta   120 tcctcgtgta ataaagctct tccccaatat ctcgatagat                           160

<210> SEQ ID NO 101
<211> LENGTH: 22
<212> TYPE: DNA
<213> ORGANISM: Homo sapiens

<400> SEQUENCE: 101
ggctgaatag tattcccttg tg                                                22

<210> SEQ ID NO 102
<211> LENGTH: 20
<212> TYPE: DNA
<213> ORGANISM: Homo sapiens

<400> SEQUENCE: 102
tcgagatatt ggggaagagc                                                   20

<210> SEQ ID NO 103
<211> LENGTH: 199
<212> TYPE: DNA
<213> ORGANISM: Homo sapiens

<400> SEQUENCE: 103
cattttaact tgattacctc cacaaagact attccagaat aaggttatgt tctgaggtat      60 tagggttac aacttcaaca tatgaatttt gagtggacac aattcaaccc atagcacctc     120
cgtgtaagag ctgggaaggg aaagtggcta agttgtgcaa atgtgcacat tggttggaga   180
tgattaactt ctggcatgt                                                  199

<210> SEQ ID NO 104
<211> LENGTH: 22
<212> TYPE: DNA
<213> ORGANISM: Homo sapiens

<400> SEQUENCE: 104
cctccacaaa gactattcca ga                                                22

<210> SEQ ID NO 105
<211> LENGTH: 20
<212> TYPE: DNA
<213> ORGANISM: Homo sapiens

<400> SEQUENCE: 105
```

```
cactttccct tcccagctct                                              20

<210> SEQ ID NO 106
<211> LENGTH: 157
<212> TYPE: DNA
<213> ORGANISM: Homo sapiens

<400> SEQUENCE: 106 aggggggaaat tggcaatctg attctaaaat tcatacggaa aaaaacaatg gagttagaat    60
aactaaaaca gtccgaaaa agaaaaagaa atggaggact aatgctacct gatttcaagt   120
cttatcttat aaatctacat caataaagga caagttg                            157

<210> SEQ ID NO 107
<211> LENGTH: 20
<212> TYPE: DNA
<213> ORGANISM: Homo sapiens

<400> SEQUENCE: 107
gaaattggca atctgattct                                              20

<210> SEQ ID NO 108
<211> LENGTH: 21
<212> TYPE: DNA
<213> ORGANISM: Homo sapiens

<400> SEQUENCE: 108
caacttgtcc tttattgatg t                                            21

<210> SEQ ID NO 109
<211> LENGTH: 173
<212> TYPE: DNA
<213> ORGANISM: Homo sapiens

<400> SEQUENCE: 109
tctgtgtttg tctatgttga taaaacattg aaatgccaaa tagctcaaag gtcattcact    60
taagaaatct aagtactgat aacatcttag ccccgattct tcataggcat tgttaagcct   120
attataattt tggttcagag agaaggtaaa ctatattcca gacaggcata taa          173

<210> SEQ ID NO 110
<211> LENGTH: 22
<212> TYPE: DNA
<213> ORGANISM: Homo sapiens

<400> SEQUENCE: 110
ctatgttgat aaaacattga aa                                           22

<210> SEQ ID NO 111
<211> LENGTH: 20
<212> TYPE: DNA
<213> ORGANISM: Homo sapiens

<400> SEQUENCE: 111
gcctgtctgg aatatagttt                                              20

<210> SEQ ID NO 112
<211> LENGTH: 126
<212> TYPE: DNA
<213> ORGANISM: Homo sapiens

<400> SEQUENCE: 112
tgcagggcat ataatctaag ctgtaaacgt cctgtcagaa gacaacatat tcatcttgct    60
```

```
aaggtttaag ctatatgact ggcactgtgc tcaactcaga gtcattgaat gaacagtatt    120
tattta                                                               126

<210> SEQ ID NO 113
<211> LENGTH: 22
<212> TYPE: DNA
<213> ORGANISM: Homo sapiens

<400> SEQUENCE: 113
cagggcatat aatctaagct gt                                              22

<210> SEQ ID NO 114
<211> LENGTH: 21
<212> TYPE: DNA
<213> ORGANISM: Homo sapiens

<400> SEQUENCE: 114
caatgactct gagttgagca c                                               21

<210> SEQ ID NO 115
<211> LENGTH: 132
<212> TYPE: DNA
<213> ORGANISM: Homo sapiens

<400> SEQUENCE: 115
ttcacattat tcccttaaaa taaactctct ccctcccctc tcccgtctca accttgtccc     60
tttctttata taatgggtaa ttcgttaatg tcagcagaat agttttgggg ccataatggc    120
aagtatcacg tg                                                        132

<210> SEQ ID NO 116
<211> LENGTH: 19
<212> TYPE: DNA
<213> ORGANISM: Homo sapiens

<400> SEQUENCE: 116
aactctctcc ctcccctct                                                  19

<210> SEQ ID NO 117
<211> LENGTH: 20
<212> TYPE: DNA
<213> ORGANISM: Homo sapiens

<400> SEQUENCE: 117
tatggcccca aaactattct                                                 20

<210> SEQ ID NO 118
<211> LENGTH: 110
<212> TYPE: DNA
<213> ORGANISM: Homo sapiens

<400> SEQUENCE: 118
tcaggaagca acaagtactg ggcagattga tactgtagct aggctctagc tctatacctc     60
tagaataaat gttacaaact agcaacttga aagctaaacc tggcccacag                110

<210> SEQ ID NO 119
<211> LENGTH: 20
<212> TYPE: DNA
<213> ORGANISM: Homo sapiens

<400> SEQUENCE: 119
acaagtactg ggcagattga                                                 20
```

<210> SEQ ID NO 120
<211> LENGTH: 20
<212> TYPE: DNA
<213> ORGANISM: Homo sapiens

<400> SEQUENCE: 120
gccaggttta gctttcaagt                                                 20

<210> SEQ ID NO 121
<211> LENGTH: 106
<212> TYPE: DNA
<213> ORGANISM: Homo sapiens

<400> SEQUENCE: 121
tggttcttga gaattttata tcaggagaaa cactgtcagt ctgtattgaa aggaacagag     60
aaaattcgaa attaaagaag actattaaac ctccaaaatt ctggca                  106

<210> SEQ ID NO 122
<211> LENGTH: 22
<212> TYPE: DNA
<213> ORGANISM: Homo sapiens

<400> SEQUENCE: 122
ttttatatca ggagaaacac tg                                              22

<210> SEQ ID NO 123
<211> LENGTH: 21
<212> TYPE: DNA
<213> ORGANISM: Homo sapiens

<400> SEQUENCE: 123
ccagaatttt ggaggtttaa t                                               21

<210> SEQ ID NO 124
<211> LENGTH: 171
<212> TYPE: DNA
<213> ORGANISM: Homo sapiens

<400> SEQUENCE: 124
gcatcaaact acacactgtc attcctcctt tatctccaaa agcttgaaaa ttcctcactt     60
gtatctcatt ctttctctct tagaaaactg atcacctctg atgaattaga acggaatgac   120
caagctttgg gagaggcaaa agaatctcgg tgttaaagac tcagagttta a             171

<210> SEQ ID NO 125
<211> LENGTH: 22
<212> TYPE: DNA
<213> ORGANISM: Homo sapiens

<400> SEQUENCE: 125
tgtcattcct cctttatctc ca                                              22

<210> SEQ ID NO 126
<211> LENGTH: 20
<212> TYPE: DNA
<213> ORGANISM: Homo sapiens

<400> SEQUENCE: 126
ttcttttgcc tctcccaaag                                                 20

<210> SEQ ID NO 127
<211> LENGTH: 163

```
<212> TYPE: DNA
<213> ORGANISM: Homo sapiens

<400> SEQUENCE: 127
ttgaaaatta agaaaccctg gcacagtgtt gactggagcc acttacctta atagaaaata      60
aagctcacat atatccataa tgaaaagcag agaccagcac aaccatagtc acctgacagt     120
tttaaaatcc aaggccagga tcttctcaac tcaggcccac tca                       163

<210> SEQ ID NO 128
<211> LENGTH: 20
<212> TYPE: DNA
<213> ORGANISM: Homo sapiens

<400> SEQUENCE: 128
accctggcac agtgttgact                                                  20

<210> SEQ ID NO 129
<211> LENGTH: 20
<212> TYPE: DNA
<213> ORGANISM: Homo sapiens

<400> SEQUENCE: 129
tgggcctgag ttgagaagat                                                  20

<210> SEQ ID NO 130
<211> LENGTH: 20
<212> TYPE: DNA
<213> ORGANISM: Homo sapiens

<400> SEQUENCE: 130
ttttccccat ttccaactct                                                  20

<210> SEQ ID NO 131
<211> LENGTH: 122
<212> TYPE: DNA
<213> ORGANISM: Homo sapiens

<400> SEQUENCE: 131
aaaaaaaaag atgagacagg caggtgcgaa agaaataaaa gtcaaaactg atccagttgg      60
gaaactcaga attgacagtt acgtgtccttt tcatttattg atattttgag attcacaggg    120
gt                                                                    122

<210> SEQ ID NO 132
<211> LENGTH: 20
<212> TYPE: DNA
<213> ORGANISM: Homo sapiens

<400> SEQUENCE: 132
aaaagatgag acaggcaggt                                                  20

<210> SEQ ID NO 133
<211> LENGTH: 20
<212> TYPE: DNA
<213> ORGANISM: Homo sapiens

<400> SEQUENCE: 133
acccctgtga atctcaaaat                                                  20

<210> SEQ ID NO 134
<211> LENGTH: 150
<212> TYPE: DNA
<213> ORGANISM: Homo sapiens
```

```
<400> SEQUENCE: 134
gagttaaata aagcacttgc ttctattgtt tgtacctaaa cttaacagaa cacagtaagt      60
aacaagtcat tgggatgcag aaaagaaaaa agagagtgaa ggaaggagaa aaggtgaagg     120
gagaatggaa gagaggaagg gagggaggaa                                      150

<210> SEQ ID NO 135
<211> LENGTH: 21
<212> TYPE: DNA
<213> ORGANISM: Homo sapiens

<400> SEQUENCE: 135
gcacttgctt ctattgtttg t                                                21

<210> SEQ ID NO 136
<211> LENGTH: 20
<212> TYPE: DNA
<213> ORGANISM: Homo sapiens

<400> SEQUENCE: 136
cccttcctct cttccattct                                                  20

<210> SEQ ID NO 137
<211> LENGTH: 129
<212> TYPE: DNA
<213> ORGANISM: Homo sapiens

<400> SEQUENCE: 137
aaacgagcca ccagtgggag cactgcaggt atctgtgtga gacccgtact tcacaactcc      60
tgctttccct ccataaagta gcttgcattt tccacattga ctttgcagtt ctttggtatc     120
tgtattggt                                                             129

<210> SEQ ID NO 138
<211> LENGTH: 18
<212> TYPE: DNA
<213> ORGANISM: Homo sapiens

<400> SEQUENCE: 138
gtgggagcac tgcaggta                                                    18

<210> SEQ ID NO 139
<211> LENGTH: 21
<212> TYPE: DNA
<213> ORGANISM: Homo sapiens

<400> SEQUENCE: 139
acagatacca aagaactgca a                                                21

<210> SEQ ID NO 140
<211> LENGTH: 145
<212> TYPE: DNA
<213> ORGANISM: Homo sapiens

<400> SEQUENCE: 140
tggacacctt tcaacttaga aatcataaac agattcattt ccttaaagtt aatgaaaaga      60
attaacagac cctcctcaaa aaagacatat atgcagccta caatcatatg aaaaaaagtt     120
caacattact gttcagcaaa tcaaa                                           145

<210> SEQ ID NO 141
<211> LENGTH: 20
```

```
<212> TYPE: DNA
<213> ORGANISM: Homo sapiens

<400> SEQUENCE: 141
tggacacctt tcaacttaga                                              20

<210> SEQ ID NO 142
<211> LENGTH: 22
<212> TYPE: DNA
<213> ORGANISM: Homo sapiens

<400> SEQUENCE: 142
gaacagtaat gttgaacttt tt                                           22

<210> SEQ ID NO 143
<211> LENGTH: 155
<212> TYPE: DNA
<213> ORGANISM: Homo sapiens

<400> SEQUENCE: 143
tggatacatt cctagaaata gatggaaact gctcttgcaa aaagcttagc acatgttaaa   60
aattttagaa acaatttgcc aaagtttatt tagtctagtg attttgacag gttaaatgga  120
ccctttgaga tcttttttcc tcaagtacaa aggct                             155

<210> SEQ ID NO 144
<211> LENGTH: 21
<212> TYPE: DNA
<213> ORGANISM: Homo sapiens

<400> SEQUENCE: 144
tcttgcaaaa agcttagcac a                                            21

<210> SEQ ID NO 145
<211> LENGTH: 21
<212> TYPE: DNA
<213> ORGANISM: Homo sapiens

<400> SEQUENCE: 145
aaaaagatct caaagggtcc a                                            21

<210> SEQ ID NO 146
<211> LENGTH: 119
<212> TYPE: DNA
<213> ORGANISM: Homo sapiens

<400> SEQUENCE: 146
gcttttgctg aacatcaagt ggtgagccag gactcaaagc cagatcttct tgtttccctg   60
ttaggtgttt gtagcacaac tggtatctgc agactatgct gctggaaggg ctagccgtc   119

<210> SEQ ID NO 147
<211> LENGTH: 20
<212> TYPE: DNA
<213> ORGANISM: Homo sapiens

<400> SEQUENCE: 147
gcttttgctg aacatcaagt                                              20

<210> SEQ ID NO 148
<211> LENGTH: 19
<212> TYPE: DNA
<213> ORGANISM: Homo sapiens

<400> SEQUENCE: 148
```
ccttccagca gcatagtct                                                 19

<210> SEQ ID NO 149
<211> LENGTH: 161
<212> TYPE: DNA
<213> ORGANISM: Homo sapiens

<400> SEQUENCE: 149
actgtcctag aaaatccagg atgtgcagtg atcatgtatg aatgcatgga cctgcacaca   60
caggagtgaa caaagaccc accctgcca ggtcaccact catatctcac cccagcccac   120
gctagctcac actcctcccc acacaccact gacctcatca t                      161

<210> SEQ ID NO 150
<211> LENGTH: 18
<212> TYPE: DNA
<213> ORGANISM: Homo sapiens

<400> SEQUENCE: 150
aaatccagga tgtgcagt                                                  18

<210> SEQ ID NO 151
<211> LENGTH: 19
<212> TYPE: DNA
<213> ORGANISM: Homo sapiens

<400> SEQUENCE: 151
atgatgaggt cagtggtgt                                                 19

<210> SEQ ID NO 152
<211> LENGTH: 124
<212> TYPE: DNA
<213> ORGANISM: Homo sapiens

<400> SEQUENCE: 152
cacatcacag atcatagtaa atggctttaa ttttttaacg aaatctcact actgcaaatg   60
cattgttgtc ctagctaatg aatgcataga gtattgcctg caaaataata attgagattc  120
tatt                                                               124

<210> SEQ ID NO 153
<211> LENGTH: 22
<212> TYPE: DNA
<213> ORGANISM: Homo sapiens

<400> SEQUENCE: 153
catcacagat catagtaaat gg                                             22

<210> SEQ ID NO 154
<211> LENGTH: 21
<212> TYPE: DNA
<213> ORGANISM: Homo sapiens

<400> SEQUENCE: 154
aattattatt ttgcaggcaa t                                              21

<210> SEQ ID NO 155
<211> LENGTH: 151
<212> TYPE: DNA
<213> ORGANISM: Homo sapiens

<400> SEQUENCE: 155
ttatcctcca catcctcatg aggcaaacac ctttcctacc ttaccgctcc ccagtggcct   60

-continued

```
ccctgttgcc ttcttattca agactaagac tctctagaat gttctttatc ctgagtccag    120
ctgattgtct atactaatat cagtacgggg t                                   151

<210> SEQ ID NO 156
<211> LENGTH: 20
<212> TYPE: DNA
<213> ORGANISM: Homo sapiens

<400> SEQUENCE: 156
catgaggcaa acacctttcc                                                 20

<210> SEQ ID NO 157
<211> LENGTH: 22
<212> TYPE: DNA
<213> ORGANISM: Homo sapiens

<400> SEQUENCE: 157
gctggactca ggataaagaa ca                                              22

<210> SEQ ID NO 158
<211> LENGTH: 145
<212> TYPE: DNA
<213> ORGANISM: Homo sapiens

<400> SEQUENCE: 158
agggtgcagc actttattat ggaagcctga gctgactaat acaggtgtct ctatatctca     60
ctgagggaaa gtgacaggaa agtaagaacc atttatgtcc aagagtccag aggagtcaac    120
cagattctgg gggaaaagaa ggtac                                          145

<210> SEQ ID NO 159
<211> LENGTH: 20
<212> TYPE: DNA
<213> ORGANISM: Homo sapiens

<400> SEQUENCE: 159
tggaagcctg agctgactaa                                                 20

<210> SEQ ID NO 160
<211> LENGTH: 20
<212> TYPE: DNA
<213> ORGANISM: Homo sapiens

<400> SEQUENCE: 160 ccttctttc ccccagaatc                                                  20

<210> SEQ ID NO 161
<211> LENGTH: 154
<212> TYPE: DNA
<213> ORGANISM: Homo sapiens

<400> SEQUENCE: 161
tgagaattta ggagaacaga agatcagagg gctgcacagg ctaaactaga caatgagccc     60
atgcaagtaa gttaagagga gaagcgggta agtatgcacc tgctttgtct aggtgaccag    120
caagcattta gcaatagtct tttcaaaaca acag                                154

<210> SEQ ID NO 162
<211> LENGTH: 22
<212> TYPE: DNA
<213> ORGANISM: Homo sapiens

<400> SEQUENCE: 162
```

```
ttaggagaac agaagatcag ag                                              22

<210> SEQ ID NO 163
<211> LENGTH: 22
<212> TYPE: DNA
<213> ORGANISM: Homo sapiens

<400> SEQUENCE: 163
aaagactatt gctaaatgct tg                                              22

<210> SEQ ID NO 164
<211> LENGTH: 106
<212> TYPE: DNA
<213> ORGANISM: Homo sapiens

<400> SEQUENCE: 164
aaacaggcaa aataagcgta gggctgtgtg tgcaacagtt aatcataaag ccatcaccag     60
gagacgtcac tgggcgcctt ctggagtcta tccgtcctaa ctttgc                   106

<210> SEQ ID NO 165
<211> LENGTH: 20
<212> TYPE: DNA
<213> ORGANISM: Homo sapiens

<400> SEQUENCE: 165
taagcgtagg gctgtgtgtg                                                 20

<210> SEQ ID NO 166
<211> LENGTH: 21
<212> TYPE: DNA
<213> ORGANISM: Homo sapiens

<400> SEQUENCE: 166
ggacggatag actccagaag g                                               21

<210> SEQ ID NO 167
<211> LENGTH: 105
<212> TYPE: DNA
<213> ORGANISM: Homo sapiens

<400> SEQUENCE: 167
gaatgacctt ggcactttta tcaaacatca actggccaca cacaggtgag tctacttctg     60
gacacttatc ctgttccatt catctgtata tctctatcct tacac                    105

<210> SEQ ID NO 168
<211> LENGTH: 23
<212> TYPE: DNA
<213> ORGANISM: Homo sapiens

<400> SEQUENCE: 168
gaatgacctt ggcactttta tca                                             23

<210> SEQ ID NO 169
<211> LENGTH: 27
<212> TYPE: DNA
<213> ORGANISM: Homo sapiens

<400> SEQUENCE: 169
aaggatagag atatacagat gaatgga                                         27

<210> SEQ ID NO 170
<211> LENGTH: 129
```

```
<212> TYPE: DNA
<213> ORGANISM: Homo sapiens

<400> SEQUENCE: 170
ctgctggaat aggctgcttg gccatgttct tggaagctac caccatatca aggtaatttc    60
ccacacaaca ttccagcccc tgctttcctc tctggcctta tctagggcca ttccccaact   120
caggtgaat                                                           129

<210> SEQ ID NO 171
<211> LENGTH: 20
<212> TYPE: DNA
<213> ORGANISM: Homo sapiens

<400> SEQUENCE: 171
ggccatgttc ttggaagcta                                                20

<210> SEQ ID NO 172
<211> LENGTH: 20
<212> TYPE: DNA
<213> ORGANISM: Homo sapiens

<400> SEQUENCE: 172
ttcacctgag ttggggaatg                                                20

<210> SEQ ID NO 173
<211> LENGTH: 138
<212> TYPE: DNA
<213> ORGANISM: Homo sapiens

<400> SEQUENCE: 173
acctttgttc catgcaccgc gcaaatacct gggaacccctt attgcccaac tcaagagcca   60
gagtcctctg tcatcatttt gcctctctcc taagtgagag gactgagtgc agacttggtg   120
tttgtgggtg aggcatgt                                                 138

<210> SEQ ID NO 174
<211> LENGTH: 18
<212> TYPE: DNA
<213> ORGANISM: Homo sapiens

<400> SEQUENCE: 174
catgcaccgc gcaaatac                                                  18

<210> SEQ ID NO 175
<211> LENGTH: 19
<212> TYPE: DNA
<213> ORGANISM: Homo sapiens

<400> SEQUENCE: 175
atgcctcacc cacaaacac                                                 19

<210> SEQ ID NO 176
<211> LENGTH: 159
<212> TYPE: DNA
<213> ORGANISM: Homo sapiens

<400> SEQUENCE: 176
ctcctgagtc caagcccttc tcactcacct ctttcttgaa ctaatttctt cctgtttttt    60
tccagtcctc ccttctgttc atgtctctcc tctgcacact tccattttgt ggttcagaaa   120
atgtcaccgt cccagtcaca cttgccttat ggctgttgt                          159
```

```
<210> SEQ ID NO 177
<211> LENGTH: 20
<212> TYPE: DNA
<213> ORGANISM: Homo sapiens

<400> SEQUENCE: 177
tccaagccct tctcactcac                                                      20

<210> SEQ ID NO 178
<211> LENGTH: 20
<212> TYPE: DNA
<213> ORGANISM: Homo sapiens

<400> SEQUENCE: 178
ctgggacggt gacattttct                                                      20

<210> SEQ ID NO 179
<211> LENGTH: 132
<212> TYPE: DNA
<213> ORGANISM: Homo sapiens

<400> SEQUENCE: 179
cccaggaaga gtggaaagat taacctttgt gagccaaacc agtgacactt gattacttga          60
cagaactaat ccttctgtcc tgatgacaga acttcaacta cacaggtaca tgcaagctaa         120
tatctgttgt aa                                                             132

<210> SEQ ID NO 180
<211> LENGTH: 21
<212> TYPE: DNA
<213> ORGANISM: Homo sapiens

<400> SEQUENCE: 180
cccaggaaga gtggaaagat t                                                    21

<210> SEQ ID NO 181
<211> LENGTH: 21
<212> TYPE: DNA
<213> ORGANISM: Homo sapiens

<400> SEQUENCE: 181
ttagcttgca tgtacctgtg t                                                    21

<210> SEQ ID NO 182
<211> LENGTH: 165
<212> TYPE: DNA
<213> ORGANISM: Homo sapiens

<400> SEQUENCE: 182
gcctggcaag ctagatgggg tgaattttca cctgccacag ccgcaagtca aagccaccgg          60
cttctctctt ctccctccca ttgctcctga cagccagggt taatattttg cctcatgtaa         120
acagggaggc atccacccga gaatctcccc tcagcccaca taagc                         165

<210> SEQ ID NO 183
<211> LENGTH: 20
<212> TYPE: DNA
<213> ORGANISM: Homo sapiens

<400> SEQUENCE: 183
agctagatgg ggtgaatttt                                                      20

<210> SEQ ID NO 184
<211> LENGTH: 18
```

```
<212> TYPE: DNA
<213> ORGANISM: Homo sapiens

<400> SEQUENCE: 184
tgggctgagg ggagattc                                                    18

<210> SEQ ID NO 185
<211> LENGTH: 160
<212> TYPE: DNA
<213> ORGANISM: Homo sapiens

<400> SEQUENCE: 185
atcaagctaa ttaatgttat ctatcacttc acatagttca accttttttt gtggtgagag     60
tactgaagat ctactctctt agcaattttc aaatctaaaa tacattatta ttaacacagt    120
cactgtgccg tacgttagct ctgaggacct tattcatttt                          160

<210> SEQ ID NO 186
<211> LENGTH: 22
<212> TYPE: DNA
<213> ORGANISM: Homo sapiens

<400> SEQUENCE: 186
atcaagctaa ttaatgttat ct                                              22

<210> SEQ ID NO 187
<211> LENGTH: 20
<212> TYPE: DNA
<213> ORGANISM: Homo sapiens

<400> SEQUENCE: 187
aatgaataag gtcctcagag                                                 20

<210> SEQ ID NO 188
<211> LENGTH: 124
<212> TYPE: DNA
<213> ORGANISM: Homo sapiens

<400> SEQUENCE: 188
tttaatctga tcattgccct atgaggtagg gagtattctg attcccattt tataaataag     60
gaacccgagg cttagagagc atcagtgact tgttcaaggt cacccacagc tgtcaagtga    120
caga                                                                 124

<210> SEQ ID NO 189
<211> LENGTH: 21
<212> TYPE: DNA
<213> ORGANISM: Homo sapiens

<400> SEQUENCE: 189
tttaatctga tcattgccct a                                               21

<210> SEQ ID NO 190
<211> LENGTH: 18
<212> TYPE: DNA
<213> ORGANISM: Homo sapiens

<400> SEQUENCE: 190
agctgtgggt gaccttga                                                   18

<210> SEQ ID NO 191
<211> LENGTH: 128
<212> TYPE: DNA
<213> ORGANISM: Homo sapiens
```

<400> SEQUENCE: 191
tgtcccacca ttgtgtatta ggtttgtaga gcgtagacaa cttgcctttt tagtttgtag    60
gtttctgtat caagagaaga tgtgtgtggg cctaacctag attacaggat cctggacttc   120
aagtctga                                                            128

<210> SEQ ID NO 192
<211> LENGTH: 20
<212> TYPE: DNA
<213> ORGANISM: Homo sapiens

<400> SEQUENCE: 192
tgtcccacca ttgtgtatta                                                20

<210> SEQ ID NO 193
<211> LENGTH: 20
<212> TYPE: DNA
<213> ORGANISM: Homo sapiens

<400> SEQUENCE: 193
tcagacttga agtccaggat                                                20

<210> SEQ ID NO 194
<211> LENGTH: 128
<212> TYPE: DNA
<213> ORGANISM: Homo sapiens

<400> SEQUENCE: 194
tcatttgcta aggtcggata gctcctaatt ggcaaagtca cgatgggatc ccagggattc    60
tgaggatgaa gcctgtgttt aataactatt atgccaagtg agcattttca aatatatgag   120
agaaatta                                                            128

<210> SEQ ID NO 195
<211> LENGTH: 19
<212> TYPE: DNA
<213> ORGANISM: Homo sapiens

<400> SEQUENCE: 195
catttgctaa ggtcggata                                                 19

<210> SEQ ID NO 196
<211> LENGTH: 20
<212> TYPE: DNA
<213> ORGANISM: Homo sapiens

<400> SEQUENCE: 196
tatttgaaaa tgctcacttg                                                20

<210> SEQ ID NO 197
<211> LENGTH: 159
<212> TYPE: DNA
<213> ORGANISM: Homo sapiens

<400> SEQUENCE: 197
cattgcttca ggggtgttag ttttgtgttc acaactagat tataaactcc tcttgcattc    60
ctgatggcag tgacttgaag gcatttattt gaagaataat agacatacag aaaggggcac   120
atgtcataaa ggtacagctg gacgactttt cacaaagtg                          159

<210> SEQ ID NO 198
<211> LENGTH: 20

<212> TYPE: DNA
<213> ORGANISM: Homo sapiens

<400> SEQUENCE: 198
gcttcagggg tgttagtttt                                               20

<210> SEQ ID NO 199
<211> LENGTH: 20
<212> TYPE: DNA
<213> ORGANISM: Homo sapiens

<400> SEQUENCE: 199
ctttgtgaaa agtcgtccag                                               20

<210> SEQ ID NO 200
<211> LENGTH: 117
<212> TYPE: DNA
<213> ORGANISM: Homo sapiens

<400> SEQUENCE: 200
gagaggatgg tgccatcatg gaaagcatgg ggcagtcatg gagatgacgg agtagctcat   60
ggagaagata atgccatcat ggaaggcata gtgcagtcat ggagatgatg gtgcagc    117

<210> SEQ ID NO 201
<211> LENGTH: 18
<212> TYPE: DNA
<213> ORGANISM: Homo sapiens

<400> SEQUENCE: 201
ccatcatgga aagcatgg                                                 18

<210> SEQ ID NO 202
<211> LENGTH: 20
<212> TYPE: DNA
<213> ORGANISM: Homo sapiens

<400> SEQUENCE: 202
tcatctccat gactgcacta                                               20

<210> SEQ ID NO 203
<211> LENGTH: 167
<212> TYPE: DNA
<213> ORGANISM: Homo sapiens

<400> SEQUENCE: 203
atggggcagt catggagatg acggagtagc tcatggagaa aataatgcca tcatggaagg   60
catagtgcag tcatggagat gatggtgcag ctcatggaga agatggtgcc atcatggaag  120
gcatggtgca atcatggagt agacagtgca gctgggccaa gattctc                167

<210> SEQ ID NO 204
<211> LENGTH: 20
<212> TYPE: DNA
<213> ORGANISM: Homo sapiens

<400> SEQUENCE: 204
gagatgacgg agtagctcat                                               20

<210> SEQ ID NO 205
<211> LENGTH: 18
<212> TYPE: DNA
<213> ORGANISM: Homo sapiens

<400> SEQUENCE: 205

```
cccagctgca ctgtctac                                                      18

<210> SEQ ID NO 206
<211> LENGTH: 128
<212> TYPE: DNA
<213> ORGANISM: Homo sapiens

<400> SEQUENCE: 206
gatgtgcctc tcttgttcca atcacaggac aggggtataa ctaggggcac tgtctatact        60
ggctgcactc tggccagtgc tgtcccaggt agattcatca gggtctagag cttcagctaa       120
cagcatga                                                                128

<210> SEQ ID NO 207
<211> LENGTH: 20
<212> TYPE: DNA
<213> ORGANISM: Homo sapiens

<400> SEQUENCE: 207
tcttgttcca atcacaggac                                                    20

<210> SEQ ID NO 208
<211> LENGTH: 20
<212> TYPE: DNA
<213> ORGANISM: Homo sapiens

<400> SEQUENCE: 208
atgctgttag ctgaagctct                                                    20

<210> SEQ ID NO 209
<211> LENGTH: 109
<212> TYPE: DNA
<213> ORGANISM: Homo sapiens

<400> SEQUENCE: 209
ttttattcat taagttgaaa gctcctaaag cagagggacc atattttat gtcccaactc         60 tccttaaggc cttgcctatg atagcacatc tcttcaatag aattgtcct                   109

<210> SEQ ID NO 210
<211> LENGTH: 20
<212> TYPE: DNA
<213> ORGANISM: Homo sapiens

<400> SEQUENCE: 210
tgaaagctcc taaagcagag                                                    20

<210> SEQ ID NO 211
<211> LENGTH: 20
<212> TYPE: DNA
<213> ORGANISM: Homo sapiens

<400> SEQUENCE: 211
ttgaagagat gtgctatcat                                                    20

<210> SEQ ID NO 212
<211> LENGTH: 163
<212> TYPE: DNA
<213> ORGANISM: Homo sapiens

<400> SEQUENCE: 212
cacataacta ataaatttgt aagtatgtgc aacggctcac acttgcttcc agaatggcac        60
ctaaaaaaca gatttaccct tccccaaatt cagatatgga attaaatgta atgtcaggaa       120
```

```
aactgtctaa gagttggaaa tgggaaaaaa atgttctttt ggt         163
```

<210> SEQ ID NO 213
<211> LENGTH: 21
<212> TYPE: DNA
<213> ORGANISM: Homo sapiens
<400> SEQUENCE: 213

```
aatttgtaag tatgtgcaac g                                 21
```

<210> SEQ ID NO 214
<211> LENGTH: 207
<212> TYPE: DNA
<213> ORGANISM: Homo sapiens
<400> SEQUENCE: 214

```
aaagaccagc ttttagctga acatcagggc tgccttcaga gtttaattac cgccctcccc    60
atggggccaa atgagccatc gactcctccc aaggggttc ggcttggtac tgatcttaa    120 gtaagtaaac gctaaaccag ctcatcttaa agcgcccaca tctgatttcc tgctctgctg   180
caagacagta ggtgactggt aatgacc                                       207
```

<210> SEQ ID NO 215
<211> LENGTH: 20
<212> TYPE: DNA
<213> ORGANISM: Homo sapiens
<400> SEQUENCE: 215

```
agggctgcct tcagagttta                                   20
```

<210> SEQ ID NO 216
<211> LENGTH: 20
<212> TYPE: DNA
<213> ORGANISM: Homo sapiens
<400> SEQUENCE: 216

```
gcgctttaag atgagctggt                                   20
```

<210> SEQ ID NO 217
<211> LENGTH: 192
<212> TYPE: DNA
<213> ORGANISM: Homo sapiens
<400> SEQUENCE: 217

```
actctgctcc cagtgtgaac atggggaaag ttgattaaac tctctgactt cagattcctc    60
atgtaaaatg tggggaaaca gctctgactt aatggtgtca ctgtgaggag taaatgaggt   120
agcatattta aaggattttg tatagtgctg gtgacagtaa ccagccaata gatgatatag   180
ctagtaatag ca                                                       192
```

<210> SEQ ID NO 218
<211> LENGTH: 20
<212> TYPE: DNA
<213> ORGANISM: Homo sapiens
<400> SEQUENCE: 218

```
tgaacatggg gaaagttgat                                   20
```

<210> SEQ ID NO 219
<211> LENGTH: 22
<212> TYPE: DNA
<213> ORGANISM: Homo sapiens

<400> SEQUENCE: 219
tcaccagcac tatacaaaat cc                                              22

<210> SEQ ID NO 220
<211> LENGTH: 170
<212> TYPE: DNA
<213> ORGANISM: Homo sapiens

<400> SEQUENCE: 220
cttcactgac cacttcctta actgtccact ccgaaacacc ccttcttcct gttcttccaa     60
tacaccaaac tctttcttgc ctctgtgtgc ttgcccatgc tgttccttct ggcttcttcc    120
ttcacattca agtcttgact tagatgtcac ttgccaaggg agaccttgga                170

<210> SEQ ID NO 221
<211> LENGTH: 21
<212> TYPE: DNA
<213> ORGANISM: Homo sapiens

<400> SEQUENCE: 221
acttccttaa ctgtccactc c                                               21

<210> SEQ ID NO 222
<211> LENGTH: 19
<212> TYPE: DNA
<213> ORGANISM: Homo sapiens

<400> SEQUENCE: 222
ccttggcaag tgacatcta                                                  19

<210> SEQ ID NO 223
<211> LENGTH: 181
<212> TYPE: DNA
<213> ORGANISM: Homo sapiens

<400> SEQUENCE: 223
aaacatccca atagacaaaa ctccaagaag agtcaaaaca agaataaagt acaggtcatc     60
ttttcttttg cactcctgac agcactttgt acatggtaat aataatctac caattaacta    120
cataagccac atggttttat catagtgtga agctttgtat ccagaaagga gagaaggctc    180
c                                                                    181

<210> SEQ ID NO 224
<211> LENGTH: 22
<212> TYPE: DNA
<213> ORGANISM: Homo sapiens

<400> SEQUENCE: 224
ccaagaagag tcaaaacaag aa                                              22

<210> SEQ ID NO 225
<211> LENGTH: 21
<212> TYPE: DNA
<213> ORGANISM: Homo sapiens

<400> SEQUENCE: 225
tctcctttct ggatacaaag c                                               21

<210> SEQ ID NO 226
<211> LENGTH: 149
<212> TYPE: DNA
<213> ORGANISM: Homo sapiens

<400> SEQUENCE: 226
ggcagaggca tggggtgcat agggatatgg ggtgggccag tttgctcctc agaccagaag    60
gggtgcagga ctcccccga tcaggatcat ggagaaaggt gtggacagag gaagggaggg   120
agggagaaat ggcagctgcc ctgcagtgg                                      149

<210> SEQ ID NO 227
<211> LENGTH: 20
<212> TYPE: DNA
<213> ORGANISM: Homo sapiens

<400> SEQUENCE: 227
ttgctcctca gaccagaagg                                                20

<210> SEQ ID NO 228
<211> LENGTH: 20
<212> TYPE: DNA
<213> ORGANISM: Homo sapiens

<400> SEQUENCE: 228
ctcccttcct ctgtccacac                                                20

<210> SEQ ID NO 229
<211> LENGTH: 165
<212> TYPE: DNA
<213> ORGANISM: Homo sapiens

<400> SEQUENCE: 229
cagggactaa gtgtctctga caatacattc agccactact acagtatgaa gccagcccct    60
catccccacc ttcagagacc cctggtgcct cagattcctc ggccattctg gagctgctgt   120
gcccgaggct tgtgtagttg gagatcattt tggcagtcag tgctg                    165

<210> SEQ ID NO 230
<211> LENGTH: 22
<212> TYPE: DNA
<213> ORGANISM: Homo sapiens

<400> SEQUENCE: 230
tgtctctgac aatacattca gc                                             22

<210> SEQ ID NO 231
<211> LENGTH: 20
<212> TYPE: DNA
<213> ORGANISM: Homo sapiens

<400> SEQUENCE: 231
ctgactgcca aaatgatctc                                                20

<210> SEQ ID NO 232
<211> LENGTH: 181
<212> TYPE: DNA
<213> ORGANISM: Homo sapiens

<400> SEQUENCE: 232
cctgtctccg tgcgtgaaag ccggctccaa agtgccttct gtcctatctg ccttccgcac    60
ctggctttcc tgaaagaaag aaaacgcgtg gcttatcttt tcacggcacg ccaccttcac   120
tctcactttt tcttttctaa taaataccctc tggatgggtt agtggtaatc tctcctcaaa   180
c                                                                    181

```
<210> SEQ ID NO 233
<211> LENGTH: 20
<212> TYPE: DNA
<213> ORGANISM: Homo sapiens

<400> SEQUENCE: 233
gctccaaagt gccttctgtc                                                    20

<210> SEQ ID NO 234
<211> LENGTH: 20
<212> TYPE: DNA
<213> ORGANISM: Homo sapiens

<400> SEQUENCE: 234
ccactaaccc atccagaggt                                                    20

<210> SEQ ID NO 235
<211> LENGTH: 198
<212> TYPE: DNA
<213> ORGANISM: Homo sapiens

<400> SEQUENCE: 235
gggagcacaa cctaggcccc tcctggggag gtggtggagt cagaatcacg taagagacaa        60
agttccagtc cctcagtgcc ggctccattg tcccctggac ttcccttaca aaccacagat      120
gcaaagagag cacttctcgg aatctccaca cagccacggg ggagcactca acccacgcga      180
ccctcgggcg caggtgct                                                    198

<210> SEQ ID NO 236
<211> LENGTH: 20
<212> TYPE: DNA
<213> ORGANISM: Homo sapiens

<400> SEQUENCE: 236
ctggggaggt ggtggagtca                                                    20

<210> SEQ ID NO 237
<211> LENGTH: 20
<212> TYPE: DNA
<213> ORGANISM: Homo sapiens

<400> SEQUENCE: 237
gagtgctcca ccgtggctgt                                                    20

<210> SEQ ID NO 238
<211> LENGTH: 161
<212> TYPE: DNA
<213> ORGANISM: Homo sapiens

<400> SEQUENCE: 238
cctgagaagc ttccagcaaa gcaccagcac gaaccgcccc acctccccac ctccccgcaa        60
gcgttgccgg gactgacaga ttacagagct ctggtccctc tgcactcctg ctctgccacc      120
cccagggtgt cagaatgtgc cccccacaca gtttccaaaa g                          161

<210> SEQ ID NO 239
<211> LENGTH: 18
<212> TYPE: DNA
<213> ORGANISM: Homo sapiens

<400> SEQUENCE: 239
aaagcaccag cacgaacc                                                      18
```

```
<210> SEQ ID NO 240
<211> LENGTH: 18
<212> TYPE: DNA
<213> ORGANISM: Homo sapiens

<400> SEQUENCE: 240
ggggcacatt ctgacacc                                                 18

<210> SEQ ID NO 241
<211> LENGTH: 162
<212> TYPE: DNA
<213> ORGANISM: Homo sapiens

<400> SEQUENCE: 241
atggagctgc tgcgccggcc tgagctctga tccctcctcc gacccagcct caccctgcaa   60
gcagcaccat gtggggctca gaatggggat cttaagggac cctccccaca acctcccgat  120
aagcctttcc acggagggcc caagcggaga caggagaaca ct                     162

<210> SEQ ID NO 242
<211> LENGTH: 19
<212> TYPE: DNA
<213> ORGANISM: Homo sapiens

<400> SEQUENCE: 242
ctgagctctg atccctcct                                                19

<210> SEQ ID NO 243
<211> LENGTH: 18
<212> TYPE: DNA
<213> ORGANISM: Homo sapiens

<400> SEQUENCE: 243
ttctcctgtc tccgcttg                                                 18

<210> SEQ ID NO 244
<211> LENGTH: 194
<212> TYPE: DNA
<213> ORGANISM: Homo sapiens

<400> SEQUENCE: 244
actttcagaa tgtgctgcct tccacgtgtg aaccagactg agctcctttc tgccactgat   60
gttgaattgt ccatttgctc acatcagtgt ccacgtggca aatccacagg gcgtgggtgg  120
gatcctgcag tctagacaaa gccaaggagc accgctggag gccacgttgg gcttcccaat  180
ccacatgcaa accc                                                    194

<210> SEQ ID NO 245
<211> LENGTH: 20
<212> TYPE: DNA
<213> ORGANISM: Homo sapiens

<400> SEQUENCE: 245
cctttctgcc actgatgttg                                               20

<210> SEQ ID NO 246
<211> LENGTH: 19
<212> TYPE: DNA
<213> ORGANISM: Homo sapiens

<400> SEQUENCE: 246
ttgcatgtgg attgggaag                                                19
```

```
<210> SEQ ID NO 247
<211> LENGTH: 213
<212> TYPE: DNA
<213> ORGANISM: Homo sapiens

<400> SEQUENCE: 247
tctccagcca gcgtgtcaca aagccgctca cctgctcgtg tgagtgtctg aatgcacgtg      60
tttgagtgtc agaggcgtgt gaaccacagc aactcaatct tgaataggg ctgggtaaag     120 tgaggctgag acctcccggg gctgcattcc cagatggtta aggcattcta agtcacaaga    180
tgagatagga agttcgcaca agacactggt cat                                 213

<210> SEQ ID NO 248
<211> LENGTH: 20
<212> TYPE: DNA
<213> ORGANISM: Homo sapiens

<400> SEQUENCE: 248
tcacctgctc gtgtgagtgt                                                 20

<210> SEQ ID NO 249
<211> LENGTH: 20
<212> TYPE: DNA
<213> ORGANISM: Homo sapiens

<400> SEQUENCE: 249
ccttaaccat ctgggaatgc                                                 20

<210> SEQ ID NO 250
<211> LENGTH: 152
<212> TYPE: DNA
<213> ORGANISM: Homo sapiens

<400> SEQUENCE: 250
ttgagtcctc ttaagtagtt actatagtgg agaacttgag tcattctttg tagcgtgctt      60
cgtagagcag cgtgtttgtt agaaggattt gttaatcctg tatagggtct ttacgaaggc    120
tgttttcatg gaagcttctc tttgttgact cc                                  152

<210> SEQ ID NO 251
<211> LENGTH: 22
<212> TYPE: DNA
<213> ORGANISM: Homo sapiens

<400> SEQUENCE: 251
tggagaactt gagtcattct tt                                              22

<210> SEQ ID NO 252
<211> LENGTH: 19
<212> TYPE: DNA
<213> ORGANISM: Homo sapiens

<400> SEQUENCE: 252
ggagtcaaca aagagaagc                                                  19

<210> SEQ ID NO 253
<211> LENGTH: 174
<212> TYPE: DNA
<213> ORGANISM: Homo sapiens

<400> SEQUENCE: 253
cattctctcc agctgcaaac tttcttcaac tttcctaaat tcttactaaa ttcagaggaa      60
taggataaag atcacttaga gaaagggtgc ttatggacat agcctgagtt tcctttaacc    120
```

```
tctctgcaat gggtgctttt aactagcttc tacatggcaa gctgtttcag tttg      174

<210> SEQ ID NO 254
<211> LENGTH: 21
<212> TYPE: DNA
<213> ORGANISM: Homo sapiens

<400> SEQUENCE: 254
ctttcttcaa ctttcctaaa t                                          21

<210> SEQ ID NO 255
<211> LENGTH: 19
<212> TYPE: DNA
<213> ORGANISM: Homo sapiens

<400> SEQUENCE: 255
ttgccatgta gaagctagt                                             19

<210> SEQ ID NO 256
<211> LENGTH: 175
<212> TYPE: DNA
<213> ORGANISM: Homo sapiens

<400> SEQUENCE: 256
ggacatctgg aactgcacca gcacagaacc gacacgttgt tactcatcgt cactcggcag   60
ggctgaagac caccagaact catgacaggc agacgtgcct ggcccagttg aggatgtagc  120
ttcagagcca agcgccagtc ctgttggcca cgtgggctgg gggcaggata gacca       175

<210> SEQ ID NO 257
<211> LENGTH: 19
<212> TYPE: DNA
<213> ORGANISM: Homo sapiens

<400> SEQUENCE: 257
accagcacag aaccgacac                                             19

<210> SEQ ID NO 258
<211> LENGTH: 18
<212> TYPE: DNA
<213> ORGANISM: Homo sapiens

<400> SEQUENCE: 258
aacaggactg gcgcttgg                                              18

<210> SEQ ID NO 259
<211> LENGTH: 182
<212> TYPE: DNA
<213> ORGANISM: Homo sapiens

<400> SEQUENCE: 259
ggctggttct gcccttggga ggtggttcct ttggctggac cagaatgtct gaagatgatc   60
aggagagggc caagggttgg ggggtgcccc atgtgcaccc tgagaattgc accaggcaca  120
gtgagcaact tcagccctcc ttgtgcagag ctgcagcgta cagtgccagc cctcgctggc  180
cc                                                               182

<210> SEQ ID NO 260
<211> LENGTH: 20
<212> TYPE: DNA
<213> ORGANISM: Homo sapiens

<400> SEQUENCE: 260
```

```
cttgggaggt ggttcctttg                                              20

<210> SEQ ID NO 261
<211> LENGTH: 18
<212> TYPE: DNA
<213> ORGANISM: Homo sapiens

<400> SEQUENCE: 261
ctgcacaagg agggctga                                                18

<210> SEQ ID NO 262
<211> LENGTH: 155
<212> TYPE: DNA
<213> ORGANISM: Homo sapiens

<400> SEQUENCE: 262
gttctcactt tactgagaaa cctggcagct tctcaggcca ccgcccaggt cacctgctca   60
ccagcaacgt gaaccacagg aactgaggct gtgcggagg cggctctgct ctgtgctggg  120 ccccctcct cctcactcac cctcttcagt caaag                              155

<210> SEQ ID NO 263
<211> LENGTH: 20
<212> TYPE: DNA
<213> ORGANISM: Homo sapiens

<400> SEQUENCE: 263
tactgagaaa cctggcagct                                              20

<210> SEQ ID NO 264
<211> LENGTH: 20
<212> TYPE: DNA
<213> ORGANISM: Homo sapiens

<400> SEQUENCE: 264
ctttgactga agagggtgag                                              20

<210> SEQ ID NO 265
<211> LENGTH: 180
<212> TYPE: DNA
<213> ORGANISM: Homo sapiens

<400> SEQUENCE: 265
ttagtattat tattttcata tatatttttt ataataatca tatattcaat tttatcatca   60 agaaaaagt tttaaaattc aaaatccttt catgtgcact gttttaaact taggtagaag  120
aaaaaaagtc actgaaaatc caagatgtaa taaacaggcc caacaaggc caacaaactt   180

<210> SEQ ID NO 266
<211> LENGTH: 20
<212> TYPE: DNA
<213> ORGANISM: Homo sapiens

<400> SEQUENCE: 266
ttcaatttta tcatcaagaa                                              20

<210> SEQ ID NO 267
<211> LENGTH: 20
<212> TYPE: DNA
<213> ORGANISM: Homo sapiens

<400> SEQUENCE: 267
ttgggcctgt ttattacatc                                              20
```

<210> SEQ ID NO 268
<211> LENGTH: 196
<212> TYPE: DNA
<213> ORGANISM: Homo sapiens

<400> SEQUENCE: 268
agggaacatg gccttgccca cacagatttc agacatctgg ctccagaact gtgggaggac      60
acatttctgt tgtttagaac tgcatgtttt ttatactttg ttatggctgc cctaggcaac     120
taatacagat attattttcc acttctgaac ttagcaaaat attttaaaa tgaaaattct      180 taaatgttgg cacagt                                                      196

<210> SEQ ID NO 269
<211> LENGTH: 20
<212> TYPE: DNA
<213> ORGANISM: Homo sapiens

<400> SEQUENCE: 269
ttgcccacac agatttcaga                                                   20

<210> SEQ ID NO 270
<211> LENGTH: 22
<212> TYPE: DNA
<213> ORGANISM: Homo sapiens

<400> SEQUENCE: 270
tgctaagttc agaagtggaa aa                                                22

<210> SEQ ID NO 271
<211> LENGTH: 120
<212> TYPE: DNA
<213> ORGANISM: Homo sapiens

<400> SEQUENCE: 271
ctggataaag gatgctacac gtccctggtg ggacagagca ggacggcagg ggatttcatt       60
acgccactca gaatggcagg caattgaaaa aacttataaa ttgtttattt ccagaatttt      120

<210> SEQ ID NO 272
<211> LENGTH: 20
<212> TYPE: DNA
<213> ORGANISM: Homo sapiens

<400> SEQUENCE: 272
ggataaagga tgctacacgt                                                   20

<210> SEQ ID NO 273
<211> LENGTH: 20
<212> TYPE: DNA
<213> ORGANISM: Homo sapiens

<400> SEQUENCE: 273
aaaattctgg aaataaacaa                                                   20

<210> SEQ ID NO 274
<211> LENGTH: 224
<212> TYPE: DNA
<213> ORGANISM: Homo sapiens

<400> SEQUENCE: 274
tgtcagtggt gtaatccgac tgtgaaagat cagtctaaca aaacagcggg gagagagagg       60
gctgaatcag agcaactagg tccaaagccg agggaaccac caacagatcc cctggtgacc     120

| | |
|---|---|
| caacaagaaa tgctcacagt ctggacccag tcagagtctg caggacacag cagacattct | 180 |
| ggaagttaca acagccagga gcaagaggac gcatggcctg actg | 224 |

<210> SEQ ID NO 275
<211> LENGTH: 20
<212> TYPE: DNA
<213> ORGANISM: Homo sapiens

<400> SEQUENCE: 275

| | |
|---|---|
| gggagagaga gggctgaatc | 20 |

<210> SEQ ID NO 276
<211> LENGTH: 21
<212> TYPE: DNA
<213> ORGANISM: Homo sapiens

<400> SEQUENCE: 276

| | |
|---|---|
| gctcctggct gttgtaactt c | 21 |

<210> SEQ ID NO 277
<211> LENGTH: 174
<212> TYPE: DNA
<213> ORGANISM: Homo sapiens

<400> SEQUENCE: 277

| | |
|---|---|
| cgccagagca ccccttctca gaacagaaag cgtctctaca aagtgatccg gaagtgagtg | 60 |
| tgtgagggcg ctgcgtcctc cctgctcccc ttggagttgc cctttcttgc tcagatctgg | 120 |
| gtgccttggc cttgtcctgg gcccttccgc agcccccggg gtgatccccg ctag | 174 |

<210> SEQ ID NO 278
<211> LENGTH: 19
<212> TYPE: DNA
<213> ORGANISM: Homo sapiens

<400> SEQUENCE: 278

| | |
|---|---|
| ccagagcacc ccttctcag | 19 |

<210> SEQ ID NO 279
<211> LENGTH: 18
<212> TYPE: DNA
<213> ORGANISM: Homo sapiens

<400> SEQUENCE: 279

| | |
|---|---|
| ggaagggccc aggacaag | 18 |

<210> SEQ ID NO 280
<211> LENGTH: 201
<212> TYPE: DNA
<213> ORGANISM: Homo sapiens

<400> SEQUENCE: 280

| | |
|---|---|
| tatcttacgg atttgtcaac atcatttgag aagaagtcca taggctcagc agattttat | 60 |
| gccaggtggg ccatggcata aaaatgtgaa gaatgtgctc acttagacaa tacctgtgct | 120 |
| aaaattggaa caatacagag aagattagca aattaaaaca atgttaggaa gtcagtgtgg | 180 |
| tgaggtacgg tgcctcatgc c | 201 |

<210> SEQ ID NO 281
<211> LENGTH: 21
<212> TYPE: DNA
<213> ORGANISM: Homo sapiens

<400> SEQUENCE: 281
cagcagattt ttatgccagg t         21

<210> SEQ ID NO 282
<211> LENGTH: 20
<212> TYPE: DNA
<213> ORGANISM: Homo sapiens

<400> SEQUENCE: 282
caccgtacct caccacactg         20

<210> SEQ ID NO 283
<211> LENGTH: 275
<212> TYPE: DNA
<213> ORGANISM: Homo sapiens

<400> SEQUENCE: 283
aggcagggcc ctccttgcca catgtaaagc tgcacagagc ggtcactata tgtgtttcca         60
tatttgcaat ccaaccacca ccaactgagt gtgcgtcctg atcagccgag cctgcccacg        120
gtggccacag gccctctaca ttctaatctc gagagcctga gcatgtacaa attaaacgaa        180
gcaaaacgac accacccagt tctggccgta ctataggagg tttccaggaa gggtttgtga        240
acataaacat aagctaggta acactccttt ctgaa        275

<210> SEQ ID NO 284
<211> LENGTH: 20
<212> TYPE: DNA
<213> ORGANISM: Homo sapiens

<400> SEQUENCE: 284
aaccaccacc aactgagtgt         20

<210> SEQ ID NO 285
<211> LENGTH: 20
<212> TYPE: DNA
<213> ORGANISM: Homo sapiens

<400> SEQUENCE: 285
cctcctatag tacggccaga         20

<210> SEQ ID NO 286
<211> LENGTH: 230
<212> TYPE: DNA
<213> ORGANISM: Homo sapiens

<400> SEQUENCE: 286
tcagagcatc gcctcagtgg ccatcaatag ctcggggac tggattgctt ttggctgttc         60
aggtttgtcc ccagcctggg tggtagagat ggactcccca ttagggacca gtgctgcccg        120
gctacaggct tacttgacag ccacccactg ggggtgccct cccctccccc agttgtcttc        180
catggggtgc cctctccccc agccgccttt cagaaggggc cctcccctcc        230

<210> SEQ ID NO 287
<211> LENGTH: 20
<212> TYPE: DNA
<213> ORGANISM: Homo sapiens

<400> SEQUENCE: 287
tggattgctt ttggctgttc         20

```
<210> SEQ ID NO 288
<211> LENGTH: 20
<212> TYPE: DNA
<213> ORGANISM: Homo sapiens

<400> SEQUENCE: 288
caccccatgg aagacaactg                                                   20

<210> SEQ ID NO 289
<211> LENGTH: 199
<212> TYPE: DNA
<213> ORGANISM: Homo sapiens

<400> SEQUENCE: 289
ctcatgctta catccttagc tgatcattaa actttgtgac catttcatgc tcactgcttt       60
cttgcccggg agctaatggt gaggaaaggt cactgggaac cagcgcacca acctcagaca      120
tcgattttgt tccagccttt tttcctgggc aggggtggct atcacctgct ggtaggcagc      180
ggcaggccca ctgtcctgc                                                  199

<210> SEQ ID NO 290
<211> LENGTH: 21
<212> TYPE: DNA
<213> ORGANISM: Homo sapiens

<400> SEQUENCE: 290
ttaaactttg tgaccatttc a                                                21

<210> SEQ ID NO 291
<211> LENGTH: 18
<212> TYPE: DNA
<213> ORGANISM: Homo sapiens

<400> SEQUENCE: 291
taccagcagg tgatagcc                                                    18

<210> SEQ ID NO 292
<211> LENGTH: 181
<212> TYPE: DNA
<213> ORGANISM: Homo sapiens

<400> SEQUENCE: 292
tgacagaaaa gtctcagagc agtgccttct gagctcttct acaccaagca ggcagaatgt       60
tcactgctaa tgaggctgga gctggtcccc agcagtggta ggaagcttcc aacaggctca      120
ggctgtgggt gcttgcaggg gcacagtgtg acggccacgg gcctcagagc tctggtgggc      180
t                                                                     181

<210> SEQ ID NO 293
<211> LENGTH: 20
<212> TYPE: DNA
<213> ORGANISM: Homo sapiens

<400> SEQUENCE: 293
gacagaaaag tctcagagca                                                   20

<210> SEQ ID NO 294
<211> LENGTH: 18
<212> TYPE: DNA
<213> ORGANISM: Homo sapiens

<400> SEQUENCE: 294
caagcaccca cagcctga                                                    18
```

<210> SEQ ID NO 295
<211> LENGTH: 187
<212> TYPE: DNA
<213> ORGANISM: Homo sapiens

<400> SEQUENCE: 295

```
acatctttct caaataaaga taacagcgat gtattttcac aaaagcaaga gcttagaaag      60
tactccaccc aggtatccct cttggaaaaa atacttaagg aaatatgaca aatggcaaag     120
tgattgttat ggatggaatg tttgtatcct cccaaaattc acatgttgag accctaattc     180
caatatg                                                                187
```

<210> SEQ ID NO 296
<211> LENGTH: 20
<212> TYPE: DNA
<213> ORGANISM: Homo sapiens

<400> SEQUENCE: 296

```
attttcacaa aagcaagagc                                                   20
```

<210> SEQ ID NO 297
<211> LENGTH: 20
<212> TYPE: DNA
<213> ORGANISM: Homo sapiens

<400> SEQUENCE: 297

```
ttgggaggat acaaacattc                                                   20
```

<210> SEQ ID NO 298
<211> LENGTH: 180
<212> TYPE: DNA
<213> ORGANISM: Homo sapiens

<400> SEQUENCE: 298

```
aggggcattc tacaaaacac ccaaccggtc aaggtcgctg aggccaagga gagattgggc      60
aaccgtcaca aaccagagaa gccgaggaga cctttcagcc aacgccatgt ggggtcctga     120
gcaggaccca ccggaagttg gtgcagctgc ctaaagaccg tcctggctga aagaaacag      180
```

<210> SEQ ID NO 299
<211> LENGTH: 18
<212> TYPE: DNA
<213> ORGANISM: Homo sapiens

<400> SEQUENCE: 299

```
aaggagagat tgggcaac                                                     18
```

<210> SEQ ID NO 300
<211> LENGTH: 19
<212> TYPE: DNA
<213> ORGANISM: Homo sapiens

<400> SEQUENCE: 300

```
gtttcttctc agccaggac                                                    19
```

<210> SEQ ID NO 301
<211> LENGTH: 228
<212> TYPE: DNA
<213> ORGANISM: Homo sapiens

<400> SEQUENCE: 301

```
tggccctgac ctgccagagc tgttggcctc cagctggcgg gtaaaaccca cggccttctc      60
```

```
agaacaggtt tctcaacaca tgagacagaa cacaccagac ttccaagggg aacacctgga      120
tggagctggt tacccagatc gttcaacacc gaggggcagc ggcttgaggg tctttccacg      180
aaggcttgga ttaacaagag gagcasrggt ctctccagga tgggccca                   228
```

<210> SEQ ID NO 302
<211> LENGTH: 20
<212> TYPE: DNA
<213> ORGANISM: Homo sapiens

<400> SEQUENCE: 302

```
catgagacag aacacaccag                                                  20
```

<210> SEQ ID NO 303
<211> LENGTH: 20
<212> TYPE: DNA
<213> ORGANISM: Homo sapiens

<400> SEQUENCE: 303

```
tcttgttaat ccaagccttc                                                  20
```

<210> SEQ ID NO 304
<211> LENGTH: 223
<212> TYPE: DNA
<213> ORGANISM: Homo sapiens

<400> SEQUENCE: 304

```
ccacccagtg tcacgtcacg gccccggcac gccatccacg gaccctggat ggagcccagc      60
tgcctccagg agcgcagttt aactacaaag gagccctggc tgcccgcccc gcccagacgc      120
actgacctgt tgttctctgt ggctgctgat ggcccatccc caaccactgg tgactcttcc      180
ctggggcccc aagctcagcc cctaaccccc tgttgctgga agt                        223
```

<210> SEQ ID NO 305
<211> LENGTH: 18
<212> TYPE: DNA
<213> ORGANISM: Homo sapiens

<400> SEQUENCE: 305

```
cacggaccct ggatggag                                                    18
```

<210> SEQ ID NO 306
<211> LENGTH: 18
<212> TYPE: DNA
<213> ORGANISM: Homo sapiens

<400> SEQUENCE: 306

```
cagggaagag tcaccagt                                                    18
```

<210> SEQ ID NO 307
<211> LENGTH: 186
<212> TYPE: DNA
<213> ORGANISM: Homo sapiens

<400> SEQUENCE: 307

```
cagaggactg ggctgcgggg tcaggaatgg gcacacttcc taactgcagg acactctaag      60
ggctttggtc atgcacacgc agccaagaga aggtgtcgct gacacacagc cttcaggag       120 cggacttgga gacctcgcca aggaccagga ctccccagca ctcacactcc cttaggcgct      180
gaagtc                                                                 186
```

```
<210> SEQ ID NO 308
<211> LENGTH: 20
<212> TYPE: DNA
<213> ORGANISM: Homo sapiens

<400> SEQUENCE: 308
actctaaggg ctttggtcat                                              20

<210> SEQ ID NO 309
<211> LENGTH: 20
<212> TYPE: DNA
<213> ORGANISM: Homo sapiens

<400> SEQUENCE: 309
ctaagggagt gtgagtgctg                                              20

<210> SEQ ID NO 310
<211> LENGTH: 185
<212> TYPE: DNA
<213> ORGANISM: Homo sapiens

<400> SEQUENCE: 310
gaagaggaca acacggggct gtctgcagag cacctgccac gcgccaggct ctgtgtccac   60
aagcacggcg gctgctccca catgacagag ctcgtgcggc agctccagga ctgtctggtg  120
ccagagcccc agctctccgc cagccccagg ccactgtgcg aggccctcag tgaagagggg  180
gccgt                                                             185

<210> SEQ ID NO 311
<211> LENGTH: 18
<212> TYPE: DNA
<213> ORGANISM: Homo sapiens

<400> SEQUENCE: 311
cgccaggctc tgtgtcca                                                18

<210> SEQ ID NO 312
<211> LENGTH: 18
<212> TYPE: DNA
<213> ORGANISM: Homo sapiens

<400> SEQUENCE: 312 ggcccctct tcactgag                                                 18

<210> SEQ ID NO 313
<211> LENGTH: 173
<212> TYPE: DNA
<213> ORGANISM: Homo sapiens

<400> SEQUENCE: 313
tctaaataat gttaatgatc aaatttagtc agatctcaat cttcatatgt tagttgcctt   60
cttaataaat attctgtttt ctttatcgtt ctttatttgt atctccacct tcatttctga  120
ttaaattaag aagttttgtc tcttccattt aataattaat gtatttaata acc         173

<210> SEQ ID NO 314
<211> LENGTH: 22
<212> TYPE: DNA
<213> ORGANISM: Homo sapiens

<400> SEQUENCE: 314
tttagtcaga tctcaatctt ca                                           22
```

```
<210> SEQ ID NO 315
<211> LENGTH: 22
<212> TYPE: DNA
<213> ORGANISM: Homo sapiens

<400> SEQUENCE: 315
aatggaagag acaaaacttc tt                                              22

<210> SEQ ID NO 316
<211> LENGTH: 194
<212> TYPE: DNA
<213> ORGANISM: Homo sapiens

<400> SEQUENCE: 316
cacactccac actggcccca cgcgggtggc gaaggactca gccagagcct ggcaggatcc     60
tggggtgtct atttccaagg aatgttctgg aagaaacata cacacatact tgtttgccag    120
atttacctgt gtggtcttcc agatgagaag cagcctgtgt cactccataa gggagagtgc    180
gtgcagcatt gaga                                                     194

<210> SEQ ID NO 317
<211> LENGTH: 18
<212> TYPE: DNA
<213> ORGANISM: Homo sapiens

<400> SEQUENCE: 317
gaaggactca gccagagc                                                   18

<210> SEQ ID NO 318
<211> LENGTH: 20
<212> TYPE: DNA
<213> ORGANISM: Homo sapiens

<400> SEQUENCE: 318 ctctcccttta tggagtgaca                                                20

<210> SEQ ID NO 319
<211> LENGTH: 225
<212> TYPE: DNA
<213> ORGANISM: Homo sapiens

<400> SEQUENCE: 319
aagaaactcc caaggaacgc attgtcccaa gttgctgcac cagtcagtgt acattcccac     60
aaacagtgca tgagagttcc tgttgcttgt gaaataaatg gtcagcattc agtgttgtca    120
gcttttaaaa ttttctcctt tctagtgggc atgtaatggt ctcacattat agttttaatt    180
tgcattttcc tggtgacatg tgatacggaa ccttcctccc atgct                   225

<210> SEQ ID NO 320
<211> LENGTH: 19
<212> TYPE: DNA
<213> ORGANISM: Homo sapiens

<400> SEQUENCE: 320
accagtcagt gtacattcc                                                  19

<210> SEQ ID NO 321
<211> LENGTH: 19
<212> TYPE: DNA
<213> ORGANISM: Homo sapiens

<400> SEQUENCE: 321
ggaaaatgca aattaaaac                                                  19
```

<210> SEQ ID NO 322
<211> LENGTH: 170
<212> TYPE: DNA
<213> ORGANISM: Homo sapiens

<400> SEQUENCE: 322
gtgcaattta attacaaacg cttaaatggg gaggtcaggg gcagagggat gatgtcacaa    60
acacacccac gtgtgcttgg tgcaaaacag taaaacaaac agcaagaagg tccatgaagg   120
aaagatcgcc tctgtcagtg ggagtaatga gagtggctga tggacaggtg              170

<210> SEQ ID NO 323
<211> LENGTH: 20
<212> TYPE: DNA
<213> ORGANISM: Homo sapiens

<400> SEQUENCE: 323
cgcttaaatg gggaggtcag                                                20

<210> SEQ ID NO 324
<211> LENGTH: 20
<212> TYPE: DNA
<213> ORGANISM: Homo sapiens

<400> SEQUENCE: 324
cctgtccatc agccactctc                                                20

<210> SEQ ID NO 325
<211> LENGTH: 189
<212> TYPE: DNA
<213> ORGANISM: Homo sapiens

<400> SEQUENCE: 325
acgccaagca ggagatgcca gacacagagt ccatcctgag agagtctgtt cctgtccaag    60
ctcagaaaca caggaagcca cctgtgctgt agcagcacac ggagatgcat cctttctggt   120
ccaccccacg gccctcattg cagtcaggga tcctctccca gaaagtccct gctgccagcc   180
cctgcccctt                                                           189

<210> SEQ ID NO 326
<211> LENGTH: 20
<212> TYPE: DNA
<213> ORGANISM: Homo sapiens

<400> SEQUENCE: 326
agcaggagat gccagacaca                                                20

<210> SEQ ID NO 327
<211> LENGTH: 20
<212> TYPE: DNA
<213> ORGANISM: Homo sapiens

<400> SEQUENCE: 327
ggtggaccag aaaggatgca                                                20

<210> SEQ ID NO 328
<211> LENGTH: 170
<212> TYPE: DNA
<213> ORGANISM: Homo sapiens

<400> SEQUENCE: 328
catgagaaag actttgttcc catgagaaca acaagagaaa ctcaaacaaa attaaaattg    60

```
tactttttcta aaagaccggg gtgggggtcg tggtcaggca gcagcatgaa gaaagccttg    120
agaactgaat tccagaaaga aacaagcata ggcaagaaag agagatgaca               170

<210> SEQ ID NO 329
<211> LENGTH: 22
<212> TYPE: DNA
<213> ORGANISM: Homo sapiens

<400> SEQUENCE: 329
cccatgagaa caacaagaga aa                                              22

<210> SEQ ID NO 330
<211> LENGTH: 20
<212> TYPE: DNA
<213> ORGANISM: Homo sapiens

<400> SEQUENCE: 330
ctctttcttg cctatgcttg                                                 20

<210> SEQ ID NO 331
<211> LENGTH: 167
<212> TYPE: DNA
<213> ORGANISM: Homo sapiens

<400> SEQUENCE: 331
aagatttaga acagctgaag cagcgagaaa aaacccagca tgagtcagaa ctggagcaac     60
tgaggattta ttttgaaaag aagttaaggg atgctgagaa aacttaccaa gaagacctaa    120
ccctgttaca gcagaggctg caggggggcga gggaagatgc tcttctg                 167

<210> SEQ ID NO 332
<211> LENGTH: 21
<212> TYPE: DNA
<213> ORGANISM: Homo sapiens

<400> SEQUENCE: 332
cagctgaagc agcgagaaaa a                                               21

<210> SEQ ID NO 333
<211> LENGTH: 19
<212> TYPE: DNA
<213> ORGANISM: Homo sapiens

<400> SEQUENCE: 333
cccctgcagc ctctgctgt                                                  19

<210> SEQ ID NO 334
<211> LENGTH: 174
<212> TYPE: DNA
<213> ORGANISM: Homo sapiens

<400> SEQUENCE: 334
gggaaactga cttggctttt gcaagggtca ttgcttcctg atgcatgttt aactgtcctg     60 tgttcactttt gttgccgcag gttttttagag gaacgtaaaa gatcaccga gaaattcagt  120 gcggaacaag atgccttcct gcaggaggcc caggagcagc atgcccgtga gctg          174

<210> SEQ ID NO 335
<211> LENGTH: 22
<212> TYPE: DNA
<213> ORGANISM: Homo sapiens

<400> SEQUENCE: 335
```

```
gggaaactga cttggctttt gc                                              22
```

<210> SEQ ID NO 336
<211> LENGTH: 20
<212> TYPE: DNA
<213> ORGANISM: Homo sapiens

<400> SEQUENCE: 336

```
ggcatcttgt tccgcactga                                                 20
```

<210> SEQ ID NO 337
<211> LENGTH: 175
<212> TYPE: DNA
<213> ORGANISM: Homo sapiens

<400> SEQUENCE: 337

```
ccctgcacac tgacctgcat gccctcgtca cctgcactct gcatgctcac catctgacgg     60
actcctgcga cgggcatggg aaggtcgccg ccgccggcag ccttgcgagc actttggatg    120
tgtgcacccg gcatgccagg cccgagtcaa cagactggcc gaccttggcg tcctg         175
```

<210> SEQ ID NO 338
<211> LENGTH: 20
<212> TYPE: DNA
<213> ORGANISM: Homo sapiens

<400> SEQUENCE: 338

```
gccctcgtca cctgcactct                                                 20
```

<210> SEQ ID NO 339
<211> LENGTH: 20
<212> TYPE: DNA
<213> ORGANISM: Homo sapiens

<400> SEQUENCE: 339

```
ccaaggtcgg ccagtctgtt                                                 20
```

<210> SEQ ID NO 340
<211> LENGTH: 155
<212> TYPE: DNA
<213> ORGANISM: Homo sapiens

<400> SEQUENCE: 340

```
tttattgctg agtggtattc cattttatgg gtccattata gtttatttgt ccagacactt     60
catggaaaga catcagtgtt tcctgttttt caatcataaa ttgatgttta attttaaaat    120
tttggaattg tagaagaaat gcaattcttt tttcc                                155
```

<210> SEQ ID NO 341
<211> LENGTH: 22
<212> TYPE: DNA
<213> ORGANISM: Homo sapiens

<400> SEQUENCE: 341

```
tgggtccatt atagtttatt tg                                              22
```

<210> SEQ ID NO 342
<211> LENGTH: 22
<212> TYPE: DNA
<213> ORGANISM: Homo sapiens

<400> SEQUENCE: 342

```
tgcatttctt ctacaattcc aa                                              22
```

<210> SEQ ID NO 343
<211> LENGTH: 208
<212> TYPE: DNA
<213> ORGANISM: Homo sapiens

<400> SEQUENCE: 343
ctttggtgca gaatcatgct gcaggcaagg tgggcccacc tccctggaat ttcatccccc      60
ccgtcagtta aacccatggt ggttttattt tctaggccac ctgatctggg aggaccacct     120
ccaagaaaag cagtcctatc gatgaacggt ctaagttatg gtgttatcag agtggatact     180
gaagaaaagt tgtcagtcct tactgttc                                         208

<210> SEQ ID NO 344
<211> LENGTH: 20
<212> TYPE: DNA
<213> ORGANISM: Homo sapiens

<400> SEQUENCE: 344
ggcccacctc cctggaattt                                                   20

<210> SEQ ID NO 345
<211> LENGTH: 22
<212> TYPE: DNA
<213> ORGANISM: Homo sapiens

<400> SEQUENCE: 345
tccactctga taacaccata ac                                                22

<210> SEQ ID NO 346
<211> LENGTH: 232
<212> TYPE: DNA
<213> ORGANISM: Homo sapiens

<400> SEQUENCE: 346
atcacctggt ttggtgcatc ctcgcagaaa gagagccata cagtgaagtg gaaacacacc      60
caaaagctct gcaatattcc tagaagttct cgaatctcct ccttaacaga gctgcagaag     120
ggaaacacag acaggaagca cctgtttgac tcagacagca gccctaatgc agtgccactc     180
aggagcattc cctcatttga agacccccca attacatgaa attatcaacc cc             232

<210> SEQ ID NO 347
<211> LENGTH: 20
<212> TYPE: DNA
<213> ORGANISM: Homo sapiens

<400> SEQUENCE: 347
acacccaaaa gctctgcaat                                                   20

<210> SEQ ID NO 348
<211> LENGTH: 20
<212> TYPE: DNA
<213> ORGANISM: Homo sapiens

<400> SEQUENCE: 348
caaatgaggg aatgctcctg                                                   20

<210> SEQ ID NO 349
<211> LENGTH: 240
<212> TYPE: DNA
<213> ORGANISM: Homo sapiens

<400> SEQUENCE: 349

```
ggaactgcag gagatccctg ctgccttcca gttcatggga tgatggcctc cacttctgcc      60
cctgtttgct tctcctttca aatcttacat gaaggtatac agtttgaaga agccagtttg     120
actccaatat ctgtgcaatg gaatactgct cattaaaaag gaattaaact attgatacac     180
acaacatggg tgaagatcaa actgtctcct tcccttttgat tcaagggaat ctgagaaatg     240
```

<210> SEQ ID NO 350
<211> LENGTH: 19
<212> TYPE: DNA
<213> ORGANISM: Homo sapiens

<400> SEQUENCE: 350

```
acttctgccc ctgtttgct                                                    19
```

<210> SEQ ID NO 351
<211> LENGTH: 21
<212> TYPE: DNA
<213> ORGANISM: Homo sapiens

<400> SEQUENCE: 351

```
tgatcttcac ccatgttgtg t                                                 21
```

<210> SEQ ID NO 352
<211> LENGTH: 187
<212> TYPE: DNA
<213> ORGANISM: Homo sapiens

<400> SEQUENCE: 352

```
tggagaaagt tgttgcaaac tgcccagaga ccctgggagt cactccagtt ttctgaaacc      60
cagatatttc agtgcctcag gagagacaag tcctgacctt ctctcctcca gctctcccag     120
gagataggca agcccctaac tccctaacta agcccttcag acctgaaatc cattgagtgg     180
cttctttt                                                              187
```

<210> SEQ ID NO 353
<211> LENGTH: 18
<212> TYPE: DNA
<213> ORGANISM: Homo sapiens

<400> SEQUENCE: 353

```
gcaaactgcc cagagacc                                                     18
```

<210> SEQ ID NO 354
<211> LENGTH: 20
<212> TYPE: DNA
<213> ORGANISM: Homo sapiens

<400> SEQUENCE: 354

```
ttagggagtt aggggcttgc                                                   20
```

<210> SEQ ID NO 355
<211> LENGTH: 184
<212> TYPE: DNA
<213> ORGANISM: Homo sapiens

<400> SEQUENCE: 355

```
agggccatgg gatgatgcag gtggagactg gagtgctaca gctgcaagca aatacatttc      60
tgtgctgtga agccacccat ttggtggtac tacgttaaaa cagctctagg aaattaatac     120
agatgttgcc tgtattttg tttctcatat tactactcat tgttttaatg atgactgttt     180
tatt                                                                  184
```

```
<210> SEQ ID NO 356
<211> LENGTH: 20
<212> TYPE: DNA
<213> ORGANISM: Homo sapiens

<400> SEQUENCE: 356
aggtggagac tggagtgcta                                              20

<210> SEQ ID NO 357
<211> LENGTH: 22
<212> TYPE: DNA
<213> ORGANISM: Homo sapiens

<400> SEQUENCE: 357
agaaacaaaa atacaggcaa ca                                           22
```

DETECTING FETAL CHROMOSOMAL ABNORMALITIES USING TANDEM SINGLE NUCLEOTIDE POLYMORPHISMS

RELATED APPLICATION(S)

This application is a continuation of U.S. application Ser. No. 11/713,069, filed Feb. 28, 2007, which claims the benefit of priority of U.S. application Ser. No. 60/777,865, filed Feb. 28, 2006, the entire contents of each of which are incorporated herein by reference.

BACKGROUND

About 6.4 million women become pregnant in the U.S. each year, and about 70% of those women have maternal serum screening and/or an ultrasound test in an attempt to determine risks for common birth defects, such as those resulting from trisomy 13, 18, and 21 (Down Syndrome). Both the sensitivity and specificity of these common non-invasive screening tools are extremely poor. The best current non-invasive tests lead to a false positive rate between 7 and 20%. This high false positive rate has two catastrophic consequences for American families and society. First, it creates a large market for the two invasive diagnostic tests, chorionic villus sampling (CVS) and amniocentesis, which each carry a fetal loss rate of 0.5%-1%. These invasive tests directly result in the loss of thousands of normal fetuses annually. Second, the high false positive rate heightens maternal anxiety and stress in the large and fixed proportion of pregnant American women who receive false positive results. However, prenatal diagnosis are critical in managing a pregnancy with chromosomal abnormalities and localized genetic abnormalities, as the diagnosis can allow for interventional care during delivery and can prevent devastating consequences for the neonate. Thus there is a tremendous need for the development of a sensitive and specific non-invasive prenatal diagnostic test for chromosomal abnormalities.

SUMMARY OF CERTAIN EMBODIMENTS OF THE INVENTION

Accordingly, certain embodiments of the present invention provide a method for determining whether a fetus has at least one chromosomal abnormality, comprising using tandem single nucleotide polymorphisms to compare fetal DNA to maternal DNA so as to determine whether the fetus has at least one chromosomal abnormality.

BRIEF DESCRIPTION OF THE FIGURES

FIG. 3A depicts results from a sample from a maternal buccal swab. FIG. 3B depicts results from a sample from maternal serum. FIG. 3C depicts results from a sample from maternal serum.

DETAILED DESCRIPTION

Figure 1:
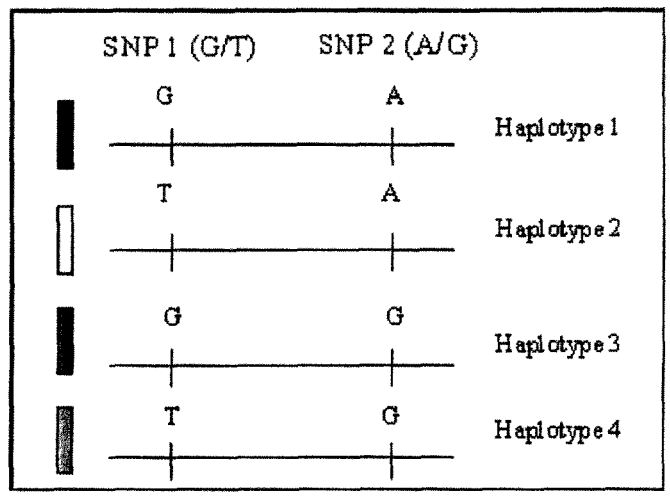
FIG. 1 depicts an example of a tandem SNP.

For years, it has been hoped that the use of fetal cells in maternal blood might be used to assess the genetic status of a developing embryo. Unfortunately, the extremely small amount of fetal cells in maternal blood (about 1 cell per ml) has proven a difficult obstacle to overcome when trying to isolate these cells for widespread clinical testing. However, cell-free fetal DNA is present in circulating maternal serum at higher percentages than fetal cells and has the potential to be assessed for chromosomal or gene defects. Cell-free fetal DNA can range from 1-47% of total DNA in maternal blood. However, a critical limitation that has yet to be successfully overcome is that maternal DNA contamination makes it difficult to differentiate fetal from maternal DNA.

As described herein, this limitation has been overcome by identifying tandem single nucleotide polymorphisms (SNPs) to detect chromosomes, e.g., to detect fetal chromosomal abnormalities. The tandem SNPs are combined with a sensitive DNA separation technology, e.g., high-fidelity PCR and constant denaturant capillary electrophoresis (CDCE), to detect fetal chromosomal abnormalities, e.g., through the simple sampling and comparison of maternal DNA to fetal DNA, e.g., from maternal serum and maternal buccal swabs. This approach substantially eliminates false positives and significantly reduces false negatives.

Accordingly, certain embodiments of the present invention provide a method for determining whether a fetus has at least one chromosomal abnormality, comprising using tandem single nucleotide polymorphisms to compare fetal DNA to maternal DNA so as to determine whether the fetus has at least one chromosomal abnormality.

In certain embodiments of the invention, fetal DNA is obtained from maternal blood. In certain embodiments of the invention, fetal DNA is cell-free fetal DNA. In certain embodiments of the invention, maternal DNA is obtained from a biological sample, e.g., maternal blood. In certain embodiments of the invention, maternal DNA is obtained from a buccal swab. In certain embodiments of the invention, maternal DNA is obtained from a biological sample that does not comprise fetal DNA.

In certain embodiments of the invention, fetal DNA is obtained from maternal blood, maternal urine, maternal sweat, maternal cells, or cell free DNA from the mother.

In certain embodiments, the biological sample is biological fluid. In certain embodiments, the biological sample is a maternal biological sample. In certain embodiments, samples may be whole blood, bone marrow, blood spots, blood serum, blood plasma, buffy coat preparations, saliva, cerebrospinal fluid, buccal swabs, solid tissues such as skin and hair, body waste products, such as feces and urine. In other embodiments, samples may be lysates, homogenates, or partially purified samples of biological materials. In other instances, biological materials can include crude or partially purified mixtures of nucleic acids. In certain embodiments, the biological sample is serum, urine, sweat, cells, or cell free DNA.

In certain embodiments of the invention, the comparison step comprises using high-fidelity PCR and constant denaturant capillary electrophoresis to compare the fetal DNA to maternal DNA. In certain embodiments of the invention, the comparison step comprises using at least about 96 tandem single nucleotide polymorphisms.

In certain embodiments of the invention, the method further comprises the step of converting the nucleic acid molecules to a homoduplex state, as opposed to being in heteroduplex form. This can be accomplished, e.g., by using an excess of primers and can aid in the tandem SNP analysis.

In certain embodiments of the invention, methods such as mutation detection technologies can be used to analyze the tandem SNPs. In certain embodiments of the invention, methods such as denaturing HPLC, denaturing capillary electrophoresis, cycling temperature capillary electrophoresis, allele-specific PCRs, quantitative real time PCR approaches such as TaqMan® PCR system, polony PCR approaches, and microarray approaches can be used to analyze the tandem SNPs.

In certain embodiments of the invention, the single nucleotide polymorphisms in each tandem single nucleotide polymorphism are each at most about 250 basepairs apart. In certain embodiments of the invention, the single nucleotide polymorphisms in each tandem single nucleotide polymorphism are each at most about 200 basepairs apart. In certain embodiments of the invention, the single nucleotide polymorphisms in each tandem single nucleotide polymorphism are each at most about 150 basepairs apart. In certain embodiments of the invention, the single nucleotide polymorphisms in each tandem single nucleotide polymorphism are each at most about 100 basepairs apart. In certain embodiments of the invention, the single nucleotide polymorphisms in each tandem single nucleotide polymorphism are each at most about 50 basepairs apart.

In certain embodiments of the invention, at least one tandem single nucleotide polymorphism is located on the p arm of chromosome 21. In certain embodiments of the invention, at least one tandem single nucleotide polymorphism is located on the q arm of chromosome 21.

In certain embodiments of the invention, the chromosomal abnormality is chromosomal aneuploidy. In certain embodiments of the invention, the chromosomal abnormality is trisomy 13, 18 or 21. In certain embodiments of the invention, the chromosomal abnormality is trisomy 21.

In certain embodiments of the invention, the chromosomal abnormality is an insertion mutation (e.g., a large insertion (≥3 megabasepair) or small insertion (<3 megabasepair). In certain embodiments of the invention, the chromosomal abnormality is a deletion mutation (e.g., a large deletion (≥3 megabasepair) or small deletion (<3 megabasepair)). The deleted region could include a deleted gene.

In certain embodiments of the invention, the methods can be used to detect copy number polymorphisms and/or copy number variants in the genome. In certain embodiments of the invention, the methods can be used to detect chromosome 22q11 deletion syndrome, which is associated with cardiac defects.

Chromosomal abnormalities include deletions associated with genetic syndromes and disorders such as the 22q11 deletion syndrome on chromosome 22, which is associated with cardiac defects. Other examples of chromosomal abnormalities include the 11q deletion syndrome on chromosome 11 and 8p deletion syndrome on chromosome 8, both of which are also associated with cardiac defects.

In certain embodiments of the invention, the fetus is a male fetus. In certain embodiments of the invention, the fetus is a female fetus. In certain embodiments of the invention, the fetus is a mammal. In certain embodiments of the invention, the fetus is a human. In certain embodiments of the invention, the fetus is a non-human mammal. In certain embodiments of the invention, the fetus has been determined to be at an elevated risk for having a chromosomal abnormality.

In certain embodiments of the invention, the method further comprises using tandem single nucleotide polymorphisms to compare paternal DNA to the fetal and/or maternal DNA.

In certain embodiments of the invention, the fetal DNA is subjected to an enrichment step. In certain embodiments of the invention, the fetal DNA is not subjected to an enrichment step.

Certain embodiments of the present invention provide a method for identifying chromosomes, comprising comparing tandem single nucleotide polymorphisms on the chromosomes so as to identify the chromosomes. Thus, the methods of the present invention are not limited to maternal-fetal analysis, but can also be applied to other situations, e.g., forensic analysis of blood samples.

In certain embodiments of the invention, the methods further comprises, prior to the comparison step, determining a set of tandem single nucleotide polymorphisms for a specific chromosome.

Certain embodiments of the present invention provide a system comprising packaging material and primers that specifically hybridize to each of the single nucleotide polymorphisms of at least one of the tandem single nucleotide polymorphisms identified herein.

Certain embodiments of the present invention provide a system comprising packaging material and primers that specifically hybridize flanking sequences of at least one of the tandem single nucleotide polymorphisms of the invention.

Certain embodiments of the present invention provide a system comprising packaging material and at least one oligonucleotide that specifically hybridizes to at least one of the tandem single nucleotide polymorphisms of the invention.

Certain embodiments of the present invention provide the use of high-fidelity PCR (HiFi-PCR) to amplify SNPs or tandem SNPs for the purpose of, e.g., determining chromosomal abnormalities.

Certain embodiments of the present invention provide the use of HiFi-PCR to amplify nucleic acids, e.g., DNA, isolated, e.g., from a maternal biological sample to analyze fetal DNA for chromosomal abnormalities.

In certain embodiments, HiFi-PCR is used to detect aneuploidy and large (≥3 megabasepairs) or small (<3 megabasepairs) deletions and/or insertions.

In certain embodiments, the maternal biological sample is serum, urine, sweat, cells, or cell free DNA.

Certain embodiments of the present invention provide an isolated nucleic acid sequence comprising at least one of SEQ ID NOs 1-357.

Certain embodiments of the present invention provide an isolated nucleic acid sequence of the invention (e.g., a nucleic acid sequence comprising a tandem SNP or a primer; e.g., at least one of SEQ ID NOs 1-357) for use in medical treatment or diagnosis.

In certain embodiments, the nucleic acid sequences may be, e.g., isolated nucleic acid sequences and may be, e.g., about 1000 or fewer, e.g., about 900 or fewer, e.g., about 800 or fewer, e.g., about 700 or fewer, e.g., about 600 or fewer, e.g., about 500 or fewer, e.g., about 400 or fewer, e.g., about 300 or fewer, e.g., about 250 or fewer, e.g., about 200 or fewer, e.g., about 150 or fewer, e.g., about 100 or fewer, or e.g., about 50 or fewer nucleic acids in length.

Thus, short haplotypes are used to detect fetal chromosomal abnormalities in maternal serum, e.g., for the most common of these defects, trisomy 21. To demonstrate this method, tandem SNPs for chromosome 21 are identified, heterozygosity of the tandem SNPs determined, the ability to detect fetal DNA from maternal serum demonstrated, and the ability to detect fetal chromosomal abnormalities in maternal serum demonstrated. 118 tandem SNPs have already been identified. These tandem SNPs are useful in the diagnosis of chromosomal abnormalities, for example, of trisomy 21. Thus, certain embodiments of the invention provide the specific tandem SNPs, or combinations thereof, as well as their use in diagnostic and therapeutic applications.

The output of these experiments, e.g., assays based on a set of tandem SNPs for chromosome 21, can be used in the clinic as an alternative to invasive diagnostic tests like amniocentesis and CVS, using, e.g., CDCE or other techniques capable of detecting the tandem SNPs. These diagnostics are sensitive and specific. The tandem SNP assay is particularly suited for fetal DNA analysis because fetal DNA present in maternal serum is generally present as short fragments (e.g., an average of 300 basepairs or fewer).

Thus, certain embodiments of the present invention are directed to each of these tandem SNPs individually, and certain embodiments are directed to combinations of any and/or all of the tandem SNPs. Certain embodiments of the invention are directed to methods of using the tandem SNPs for diagnosing chromosomal abnormalities. Certain embodiments of the invention are directed to compilations of the tandem SNPs (e.g., reference tables) that are useful for diagnosing chromosomal abnormalities. Certain embodiments of the invention are also directed to primers for each of these tandem SNPs individually, and certain embodiments are directed to combinations of primers for any and/or all of the tandem SNPs. Certain embodiments of the invention provide isolated nucleic acid sequences that comprise at least one of the tandem SNPs and compositions that comprise the isolated nucleic acid sequences.

Prenatal Screening

An increasing number of fetal medical conditions can be successfully managed during the neonatal period if an early diagnosis is made. A variety of prenatal screening tools are available for chromosomal and birth defects. The two most commonly utilized non-invasive tools are ultrasound and measurements of maternal serum markers. Both of these "tests" have inadequate sensitivity and specificity for screening the most common of the defects, Down Syndrome (trisomy 21).

An ultrasound screening called the nuchal translucency test is becoming more common. However, this test has an overall sensitivity of 77% for trisomy 21 with a false positive rate of 6% (Malone et al., Obstet Gynecol, 2003. 102(5 Pt 1): p. 1066-79). The most advanced serum marker test is the "quad" screen, which measures the levels of alpha-fetoprotein (AFP), human chorionic gonadotropin (hCG), unconjugated estriol (E3), and inhibin-A. The biological reason for these markers to be elevated or reduced in a percentage of mothers carrying children with trisomy 21 is not understood. Further, the test is only capable of assigning risk categories (i.e., 1 in 250, 1 in 100, 1 in 10), and not in making specific diagnoses. The quad screen is associated with a false positive rate of 7% and a sensitivity of less than 80%, rates which do not approach those achieved by invasive prenatal diagnostic tests (Wald et al., Lancet, 2003. 361(9360): p. 835-6).

Because of the inadequate sensitivity and specificity of currently available non-invasive tools, amniocentesis and chorionic villus sampling (CVS), both invasive procedures, remain the standard for the definitive detection of fetal chromosomal abnormalities. Both of these procedures carry a 0.5%-1% fetal loss rate, which translate into the death of thousands of normal fetuses annually. To solve this problem and meet the overwhelming need for an accurate non-invasive test, several strategies have been previously proposed by other investigators. However, those studies have been limited by their ability to detect and differentiate fetal DNA from maternal DNA.

A PCR-based approach for detecting aneuploidy relies on a method called quantitative fluorescent polymerase chain reaction (QF-PCR) of short tandem repeats (STRs). However, polymerase errors are frequently made in the repeat sequences, generating a high background "noise" for each STR assay. These PCR errors (stutters) make peak area measurements difficult and thus the detection and quantification of low frequency fetal DNA in maternal serum not possible (Dhallan et al., JAMA, 2004. 291(9): p. 1114-9).

In 1994, a technology called constant denaturant capillary electrophoresis (CDCE) combined with high-fidelity PCR (HiFi-PCR) was developed to allow researchers to detect and quantify low frequency somatic mutations present in heterogeneous cell populations (Khrapko et al., Nucleic Acids Res, 1994. 22(3): p. 364-9). Compared to other DNA separation methods, CDCE permits the highest resolution separation of DNA sequences differing by even a single base pair. The separation is based on differences in the melting temperature and the resulting electrophoretic mobility differences as the DNA molecules migrate through a linear polyacrylamide matrix under partially denaturing conditions (Khrapko et al., 1994). CDCE coupled with HiFi-PCR has been demonstrated to detect mutations in ~100 bp sequences with a sensitivity of at least $2 \times 10^{-6}$ in human cells and tissues (Li-Sucholeiki et al., Nucleic Acids Res, 2000. 28(9): p. E44). As described herein, this technology can be applied to single nucleotide polymorphisms (SNPs), natural single basepair variations present in the genome, to separate alleles. CDCE is used in the present invention to screen tandem SNPs to increase the informativeness (or heterozygosity) of each CDCE assay by increasing the number of possible alleles (or haplotypes) available. Through the use of tandem SNPs, a highly specific and sensitive assay for detecting fetal chromosomal abnormalities by simply comparing maternal serum to maternal buccal swabs has been created.

High-Fidelity PCR is an amplification method resulting in an error rate (in per basepair doubling) equal to or better than standard PCR. For example, Taq polymerase has an error rate of $\sim 10^{-4}$ per basepair doubling. As an example, *Pyrococcus furiosus* (Pfu) is a high-fidelity polymerase. The published error rate for Pfu is $1.3 \times 10^{-6}$ per basepair doubling (Cline et al, Nucleic Acids Res. 1996 Sep. 15; 24(18): 3546-3551).

Methods for improving PCR fidelity include, among others: A) using a high-fidelity polymerase enzyme; and B) the addition of chemical reagents (e.g., betaine) that can lower temperatures required during the PCR process. The prolonged heating of DNA and nucleotides during PCR can lead to damaged products, such as deaminated cytosines (uracils) and thus lead to misincorporation errors and miscopying errors during PCR (Andre, Kim, Khrapko, Thilly. Genome Res. 1997 7: 843-852. Zheng, Khrapko, Coller, Thilly, Copeland. Mutat Res. 2006 Jul. 25; 599(1-2):11-20). Examples of high-fidelity enzymes include Pfu and its derivations, or other enzymes with similar proofreading 3'→5' exonucleases.

In certain embodiments of the invention, amplification, e.g., HiFi-PCR, is performed with primers being in molar excess (e.g., $10^{12}$ copies/µl of primer vs $10^6$ or less of the template) so that it is more likely that primers will anneal with template DNA than with each other (see, e.g., Li-Sucholeiki X C, Thilly W G. Nucleic Acids Res. 2000 May 1; 28(9):E44; Thompson J R, Marcelino L, Polz M. Nucleic Acids Res. 2002 May 1; 30(9): 2083-2088.). This can significantly reduce the creation of heteroduplexes.

A "single nucleotide polymorphism (SNP)" is a single basepair variation in a nucleic acid sequence. A "tandem SNP" is a pair of SNPs that are located in a nucleic acid sequence, e.g. on a chromosome, in a manner that allows for the detection of both of the SNPs. The distance between SNPs generally is about 250 basepairs or fewer, e.g., about 200 basepairs or fewer, e.g., about 150 basepairs or fewer, e.g., about 100 basepairs or fewer, e.g., about 50 basepairs or fewer. The tandem SNPs can be detected by a variety of means that are capable of detecting the tandem SNPs. In one embodiment of the invention, constant denaturant capillary electrophoresis (CDCE) can be combined with high-fidelity PCR (HiFi-PCR) to detect the tandem SNP. In another embodiment, hybridization on a microarray is used. In another embodiment, high-fidelity PCR is used and another method capable of detecting SNPs present at low frequencies is used (e.g., denaturing HPLC, denaturing capillary electrophoresis, cycling temperature capillary electrophoresis, allele-specific PCRs, quantitative real time PCR approaches such as TaqMan® PCR system, polony sequencing approaches, microarray approaches, and mass spectrometry). In another embodiment, high-throughput sequencing approaches, e.g., at a single molecule level, are used.

The term "nucleic acid" refers to deoxyribonucleotides or ribonucleotides and polymers thereof in either single- or double-stranded form, made of monomers (nucleotides) containing a sugar, phosphate and a base that is either a purine or pyrimidine. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues.

The term "nucleotide sequence" refers to a polymer of DNA or RNA which can be single-stranded or double-stranded, optionally containing synthetic, non-natural or altered nucleotide bases capable of incorporation into DNA or RNA polymers. The terms "nucleic acid," "nucleic acid molecule," or "polynucleotide" are used interchangeably.

Certain embodiments of the invention encompass isolated or substantially purified nucleic acid compositions. In the context of the present invention, an "isolated" or "purified" DNA molecule or RNA molecule is a DNA molecule or RNA molecule that exists apart from its native environment and is therefore not a product of nature. An isolated DNA molecule or RNA molecule may exist in a purified form or may exist in a non-native environment such as, for example, a transgenic host cell. For example, an "isolated" or "purified" nucleic acid molecule is substantially free of other cellular material or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived.

The following terms are used to describe the sequence relationships between two or more nucleic acids or polynucleotides: (a) "reference sequence," (b) "comparison window," (c) "sequence identity," (d) "percentage of sequence identity," and (e) "substantial identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well-known in the art. Thus, the determination of percent identity between any two sequences can be accomplished using a mathematical algorithm. Non-limiting examples of such mathematical algorithms are the algorithm of Myers and Miller (Myers and Miller, CABIOS, 4, 11 (1988)); the local homology algorithm of Smith et al. (Smith et al., Adv. Appl. Math., 2, 482 (1981)); the homology alignment algorithm of Needleman and Wunsch (Needleman and Wunsch, J M B, 48, 443 (1970)); the search-for-similarity-method of Pearson and Lipman (Pearson and Lipman, Proc. Natl. Acad. Sci. USA, 85, 2444 (1988)); the algorithm of Karlin and Altschul (Karlin and Altschul, Proc. Natl. Acad. Sci. USA, 87, 2264 (1990)), modified as in Karlin and Altschul (Karlin and Altschul, Proc. Natl. Acad. Sci. USA 90, 5873 (1993)).

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (Higgins et al., CABIOS, 5, 151 (1989)); Corpet et al. (Corpet et al., Nucl. Acids Res., 16, 10881 (1988)); Huang et al. (Huang et al., CABIOS, 8, 155 (1992)); and Pearson et al. (Pearson et al., Meth. Mol. Biol., 24, 307 (1994)). The ALIGN program is based on the algorithm of Myers and Miller, supra. The BLAST programs of Altschul et al. (Altschul et al., J M B, 215, 403 (1990)) are based on the algorithm of Karlin and Altschul supra.

Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, less than about 0.01, or even less than about 0.001.

To obtain gapped alignments for comparison purposes, Gapped BLAST (in BLAST 2.0) can be utilized. Alternatively, PSI-BLAST (in BLAST 2.0) can be used to perform an iterated search that detects distant relationships between molecules. When utilizing BLAST, Gapped BLAST, PSI-BLAST, the default parameters of the respective programs (e.g., BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. Alignment may also be performed manually by inspection.

For purposes of the present invention, comparison of nucleotide sequences for determination of percent sequence identity to the promoter sequences disclosed herein may be made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the program.

(c) As used herein, "sequence identity" or "identity" in the context of two nucleic acid or polypeptide sequences makes reference to a specified percentage of residues in the two sequences that are the same when aligned for maximum correspondence over a specified comparison window, as measured by sequence comparison algorithms or by visual inspection. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, or 94%, or even at least 95%, 96%, 97%, 98%, or 99% sequence identity, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 70%, 80%, 90%, or even at least 95%.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, or 94%, or even 95%, 96%, 97%, 98% or 99%, sequence identity to the reference sequence over a specified comparison window. In certain embodiments, optimal alignment is conducted using the homology alignment algorithm of Needleman and Wunsch (Needleman and Wunsch, J M B, 48, 443 (1970)). An indication that two peptide sequences are substantially identical is that one peptide is immunologically reactive with antibodies raised against the second peptide. Thus, a peptide is substantially identical to a second peptide, for example, where the two peptides differ only by a conservative substitution. Thus, certain embodiments of the invention provide nucleic acid molecules that are substantially identical to the nucleic acid molecules described herein.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As noted above, another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. The thermal melting point (Tm) is the temperature (under defined ionic strength and pH) at which 50% of the target sequence hybridizes to a perfectly matched probe. Specificity is typically the function of post-hybridization washes, the critical factors being the ionic strength and temperature of the final wash solution. For DNA-DNA hybrids, the $T_m$ can be approximated from the equation of Meinkoth and Wahl (1984); $T_m 81.5°$ C.+16.6 (log M)+0.41 (% GC)–0.61 (% form)–500/L; where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the $T_m$ for the specific sequence and its complement at a defined ionic strength and pH. However, severely stringent conditions can utilize a hybridization and/or wash at 1, 2, 3, or 4° C. lower than the $T_m$; moderately stringent conditions can utilize a hybridization and/or wash at 6, 7, 8, 9, or 10° C. lower than the $T_m$; low stringency conditions can utilize a hybridization and/or wash at 11, 12, 13, 14, 15, or 20° C. lower than the $T_m$. Using the equation, hybridization and wash compositions, and desired temperature, those of ordinary skill will understand that variations in the stringency of hybridization and/or wash solutions are inherently described. If the desired degree of mismatching results in a temperature of less than 45° C. (aqueous solution) or 32° C. (formamide solution), the SSC concentration is increased so that a higher temperature can be used. Generally, highly stringent hybridization and wash conditions are selected to be about 5° C. lower than the $T_m$ for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes. Often, a high stringency wash is preceded by a low stringency wash to remove background probe signal. An example medium stringency wash for a duplex of, e.g., more than 100 nucleotides, is 1×SSC at 45° C. for 15 minutes. For short nucleotide sequences (e.g., about 10 to 50 nucleotides), stringent conditions typically involve salt concentrations of less than about 1.5 M, less than about 0.01 to 1.0 M, Na ion concentration (or other salts) at pH 7.0 to 8.3, and the temperature is typically at least about 30° C. and at least about 60° C. for long probes (e.g., >50 nucleotides). Stringent conditions may also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

Very stringent conditions are selected to be equal to the $T_m$ for a particular probe. An example of stringent conditions for hybridization of complementary nucleic acids that have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

In addition to the chemical optimization of stringency conditions, analytical models and algorithms can be applied to hybridization data-sets (e.g. microarray data) to improve stringency.

The term "treatment" or "treating," to the extent it relates to a disease or condition includes preventing the disease or condition from occurring, inhibiting the disease or condition, eliminating the disease or condition, and/or relieving one or more symptoms of the disease or condition.

The invention will now be illustrated by the following non-limiting Examples.

Example 1

Tandem SNPs for Chromosome 21

96 allelic markers on chromosome 21 are selected by examining tandem SNPs. These tandem SNPs will cover both q and p arms of the chromosome. Using heterozygosity data available through dbSNP, DCC Genotype Database and through the HapMap Project, SNPs that appear to be promising for high heterozygosity (≥25%) are selected. Because all four possibilities may not exist in nature due to haplotype blocks in regions of low recombination, those that suggest less than three haplotypes are screened out. FIG. 1 depicts an example of tandem SNPs (SNP 1=rs2839416, average estimated heterozygosity 0.444 and SNP2=rs2839417, average estimated heterozygosity 0.414).

Target sequences covering tandem SNPs are designed using Vector NTI and WinMelt software. As an example, the melting map of a CDCE target covering two tandem SNPs (dbSNP rs2839416 and rs2839417) on chromosome 21 was calculated using WinMelt according to the algorithm of Lerman and Silverstein (Lerman et al., Methods Enzymol, 1987. 155: p. 482-501) and is depicted in FIG. 2.

Figure 2:
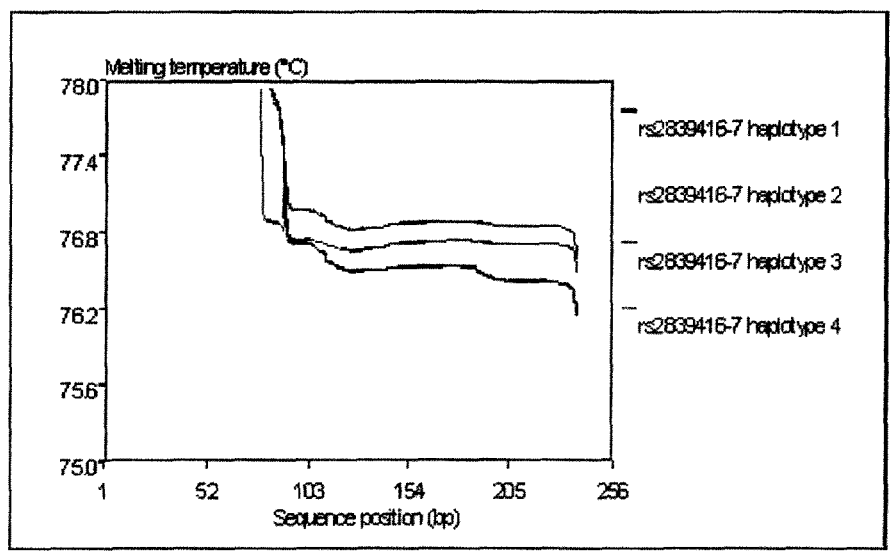
FIG. 2 depicts a DNA melting map of a constant denaturant capillary electrophoresis target sequence covering a tandem SNP.

FIG. 2 depicts a DNA melting map of a CDCE target sequence covering tandem SNPs. All four haplotypes can be theoretically separated according to DNA melting temperature. The black line indicates haplotype 1 (G,A). The yellow line indicates haplotype 2 (T,A). The red line indicates haplotype 3 (G,G). The green line indicates haplotype 4 (T,G).

HiFi PCR optimization for each target sequence is performed using Pfu polymerase. One of primers flanking the target sequence is ~20 bases in length and labeled 5' with a fluorescein molecule. The other primer is about 74 bases including a ~20-base target specific sequence and the 54-base clamp sequence. A standard HiFi PCR condition is applied to all target sequences, varying only annealing temperatures. These PCR amplicons are subjected to CDCE electrophoretic separation. The resulting electropherogram are analyzed for yield and purity of the PCR products. The purity is evaluated by comparing the peak area of the desired products to that of the byproducts and nonspecific amplification. Target sequences that can be amplified with a high PCR efficiency (≥45% per cycle) and low levels of byproducts and nonspecific amplification (≤0.1% of the desired products) are immediately be subjected to CDCE optimization. For those target sequences that do not have acceptable PCR products in the first stage, increasing amounts of $Mg^{+2}$ concentrations (up to about 7 mM) in combination with different annealing temperatures are tested. For the remaining target sequences that still do not work, primer positions are changed and the entire optimization process is repeated.

For CDCE optimization, the relevant haplotypes are created for the targets. The optimal separation condition for each haplotype should provide the greatest resolution among the observed peaks. Initial optimization is done around the theoretical melting temperature ($T_m$) in a 2° C. temperature range in increments of 0.2° C. which covers ($T_m$−1° C.±a predetermined offset) to ($T_m$+1° C.±a predetermined offset).

Electropherogram and peak measurements are transferred to a spreadsheet for analysis. To ensure the quality of the data, minimum and maximum peak heights are used. Individual markers are failed if electrophoretic spikes occur. Peak areas are used to calculate allele ratios. A check for allelic preferential amplification is performed on all 96 tandem SNPs.

Results

In the fall of 2005, the International HapMap Project publicly released genotypes and frequencies from 270 people of four ethnic populations. Chromosome 21 haplotype data from approximately 40,000 SNPs genotyped across four populations, including U.S. residents with northern and western European ancestry, residents of Ibadan, Nigeria, of Tokyo, Japan, and of Beijing, China, were downloaded (2005-10-24: HapMap Public Release #19) and converted to the + orientation. Tandem SNP candidates fell within 100 basepairs from each other and at least three haplotypes existed in all four ethnic populations. CDCE target sequences and primers are designed for the tandem SNPs identified through the HapMap Project. The neighboring sequences for each of the tandem SNPs are imported into a software program, e.g., Sequencher (Gene Codes, Ann Arbor, Mich.) and/or Vector NTI (Invitrogen, Carlsbad, Calif.) for sequence alignment and primer design, and into Winmelt (Medprobe, Oslo, Norway) or Poland software (available on the world wide web at biophys.uniduesseldorf.de/local/POLAND/poland.html) where the algorithm for computing DNA melting temperatures given the Gotoh-Tagashira values for the enthalpy of melting DNA sequences are used to calculate melting temperatures of target sequences. CDCE candidates generally have a high melting region adjacent to a low melting region, lie in a low melting region, melting temperatures of the low melting region fall below 80° C., and no "valleys" occur between the high melting region and the low melting region.

All of the 40,000 genotypes on chromosome 21 have been analyzed for tandem SNP/CDCE marker suitability. 118 tandem SNPs/CDCE targets meeting our requirements have been identified (see Table 1 for the first 42 identified and Table 2 for all 118).

Primer sequences for these 118 tandem SNP/CDCE targets have been designed. These will be optimized as described herein using HiFi PCR and CDCE. These optimizations are described herein and include the creation of relevant haplotypes for all targets, a check for allelic preferential amplification during HiFi PCR, and obtaining the greatest resolution among peaks during CDCE. Haplotypes may be separated as homoduplex peaks. However, if certain targets cannot be separated out as homoduplexes, maternal DNA can be separated from fetal DNA as heteroduplexes.

TABLE 1

| Tandem SNP #/Observed haplotypes | dbSNP Name | | Chromosome | Chromosome Position | bp dif |
|---|---|---|---|---|---|
| 1 CC/CT/AC | rs10482852 rs2822567 | A/C C/T | Chr21 Chr21 | 14613855 14613941 | 86 |
| 2 AA/AG/CG/CA | rs2822654 rs1882882 | A/C A/G | Chr21 Chr21 | 14687773 14687786 | 13 |
| 3 AG/GG/AA/GA | rs2822785 rs2822786 | A/G A/G | Chr21 Chr21 | 14876399 14876464 | 65 |
| 4 GC/AC/GT | rs2822786 rs2822787 | A/G C/T | Chr21 Chr21 | 14876464 14876531 | 67 |
| 5 AA/GT/GA | rs2822816 rs2822817 | A/G A/T | Chr21 Chr21 | 14948471 14948568 | 97 |
| 6 CA/CG/TG | rs2822878 rs2822879 | C/T A/G | Chr21 Chr21 | 15033311 15033401 | 90 |
| 7 AT/GT/AC | rs2223163 rs2822963 | A/G C/T | Chr21 Chr21 | 15149849 15149921 | 72 |
| 8 GG/AG/GT/AT | rs1297213 rs1297214 | A/G G/T | Chr21 Chr21 | 15253641 15253724 | 83 |
| 9 CT/CC/TT | rs2142450 rs10482863 | C/T C/T | Chr21 Chr21 | 15257273 15257340 | 67 |
| 10 TC/CC/TT | rs10482863 rs1041403 | C/T C/T | Chr21 Chr21 | 15257340 15257386 | 46 |
| 11 TA/CA/TG | rs2823333 rs2823334 | C/T A/G | Chr21 Chr21 | 15825896 15825985 | 89 |
| 12 GG/AC/GC | rs2823335 rs992557 | A/G C/G | Chr21 Chr21 | 15826379 15826457 | 78 |
| 13 AA/GG/AG | rs2823348 rs2823349 | A/G A/G | Chr21 Chr21 | 15833575 15833601 | 26 |
| 14 AT/AC/CT/CC | rs2823502 rs2823503 | A/C C/T | Chr21 Chr21 | 16124651 16124683 | 32 |
| 15 CC/CA/TC/TA | rs960391 rs13049140 | C/T A/C | Chr21 Chr21 | 17034864 17034893 | 29 |
| 16 CA/TA/TG | rs2824078 rs10482886 | C/T A/G | Chr21 Chr21 | 17134418 17134448 | 30 |
| 17 CT/CC/TC | rs1999288 rs208897 | C/T C/T | Chr21 Chr21 | 17696177 17696269 | 92 |
| 18 GG/GA/AA/AG | rs2824310 rs6517774 | A/G A/G | Chr21 Chr21 | 17744045 17744144 | 99 |
| 19 GG/AA/AG/GA | rs728015 rs728014 | A/G A/G | Chr21 Chr21 | 17968624 17968657 | 33 |

TABLE 1-continued

| Tandem SNP #/Observed haplotypes | dbSNP Name | Chromosome | Chromosome Position | bp dif |
|---|---|---|---|---|
| 20 GG/CG/CC/GC | rs1047978 rs2824495 | C/G Chr21 C/G Chr21 | 18091026 18091089 | 63 |
| 21 GT/GC/AT/AC | rs157058 rs150141 | A/G Chr21 C/T Chr21 | 18355312 18355365 | 53 |
| 22 GG/GT/AG/AT | rs2824733 rs2824734 | A/G Chr21 G/T Chr21 | 18610953 18611032 | 79 |
| 23 AA/GT/GA/AT | rs963638 rs963639 | A/G Chr21 A/T Chr21 | 19009158 19009214 | 56 |
| 24 AC/TA/TC/AA | rs2187166 rs2156203 | A/T Chr21 A/C Chr21 | 19081111 19081210 | 99 |
| 25 CT/TC/CC/TT | rs2825470 rs2825471 | C/T Chr21 C/T Chr21 | 19567109 19567169 | 60 |
| 26 TT/GC/GT | rs2407581 rs2825926 | G/T Chr21 C/T Chr21 | 20272611 20272639 | 28 |
| 27 GT/AT/GC/AC | rs377685 rs420778 | A/G Chr21 C/T Chr21 | 20272988 20273021 | 33 |
| 28 AG/CT/CG | rs2826058 rs2826059 | A/C Chr21 G/T Chr21 | 20464969 20465061 | 92 |
| 29 CT/CC/TT | rs2826072 rs2826073 | C/T Chr21 C/T Chr21 | 20487958 20488053 | 95 |
| 30 CC/TC/TT | rs2032203 rs2826152 | C/T Chr21 C/T Chr21 | 20598845 20598943 | 98 |
| 31 CA/TA/CG/TG | rs1735808 rs1786400 | C/T Chr21 A/G Chr21 | 20766284 20766329 | 45 |
| 32 TG/CA/CG/GA | rs2014509 rs2014519 | C/T Chr21 A/G Chr21 | 21113081 21113160 | 79 |
| 33 GA/AA/GG | rs2155798 rs2155799 | A/G Chr21 A/G Chr21 | 21471022 21471097 | 75 |
| 34 GA/GG/CA | rs1475881 rs7275487 | C/G Chr21 A/G Chr21 | 21748820 21748916 | 96 |
| 35 CG/GG/GC/CC | rs2522558 rs12627388 | C/G Chr21 C/G Chr21 | 21916691 21916714 | 23 |
| 36 GC/GT/CC/CT | rs12627388 rs2522559 | C/G Chr21 C/T Chr21 | 21916714 21916762 | 48 |
| 37 AC/GC/GT | rs1735934 rs2826958 | A/G Chr21 C/T Chr21 | 21995555 21995633 | 78 |
| 38 AC/GT/AT/GC | rs994676 rs2826982 | A/G Chr21 C/T Chr21 | 22043945 22043979 | 34 |
| 39 AA/GC/AC | rs1735976 rs2827016 | A/G Chr21 A/C Chr21 | 22054777 22054808 | 31 |
| 40 AA/GA/AG/GG | rs1013069 rs2827307 | A/G Chr21 A/G Chr21 | 22545627 22545694 | 67 |
| 41 AT/GT/AC/GC | rs244260 rs244261 | A/G Chr21 C/T Chr21 | 23311737 23311825 | 88 |
| 42 CG/CC/AG/AC | rs2051265 rs198061 | A/C Chr21 C/G Chr21 | 23334109 23334156 | 47 |

Example 2

Determining Heterozygosity of the Tandem SNPs

As a complement to Example 1, genomic DNA samples from 300 anonymous subjects have been obtained from healthy young adults who are less than 35 years old. The samples are anonymous as the only data obtained were the geographic location of the Red Cross blood donor center, donor gender, and whether or not the donor was 35 and under. These samples were spot-checked to look for the haplotypes seen in the HapMap project.

Example 3

Detecting Fetal DNA from Maternal Serum

A cohort of patients who have been confirmed to have trisomy 21 by traditional karyotype analysis are examined. Tandem SNPs are used to demonstrate detection of trisomy in patients. DNA from 20 patients who have been characterized by traditional karyotype analysis to have trisomy 21 are analyzed with the tandem SNP panel.

Biological samples, including a buccal (cheek) swab and a blood sample are collected from a cohort of pregnant women. Maternal buccal swab samples are compared to maternal serum to demonstrate that a third (paternal) peak is observed in several of the tandem SNP assays. Approximately 20 maternal buccal swab to maternal serum comparisons are made. To control for experimental artifacts, genomic DNA samples from maternal buccal swabs are utilized for each target sequence. The buccal samples are subjected to the process in parallel with the maternal blood sample. Any artifacts generated by the CDCE/HiFi-PCR procedure (including nonspecific PCR amplification and polymerase-induced mutations) are revealed as background peaks in the buccal swab samples.

Example 4

Detecting Fetal Chromosomal Abnormalities

Figure 3:
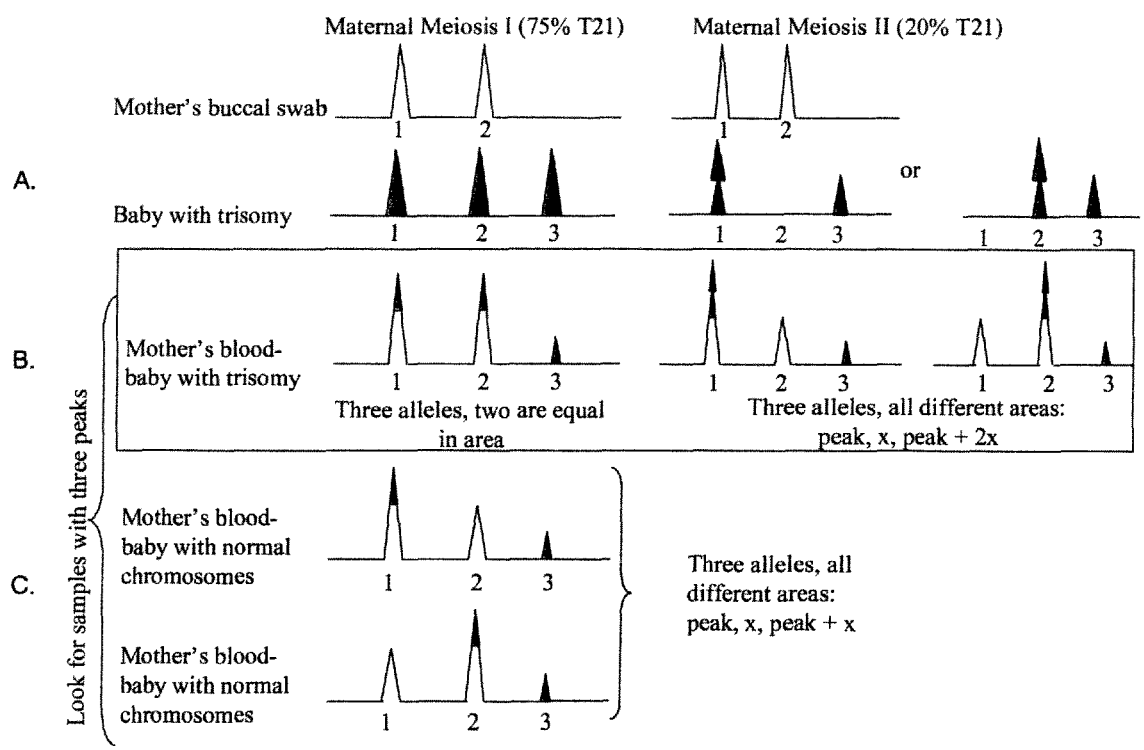
FIG. 3 depicts an example of a constant denaturant capillary electrophoresis electropherogram output.

A blinded study is performed where the goal is to detect 20 known trisomy 21 fetuses by assaying maternal serum from 40 patients (previously determined by amniocentesis or CVS) (see FIG. 3).

FIG. 3 depicts an example of a CDCE electropherogram output with the peaks at full scale. FIG. 3A depicts a sample from maternal buccal swab. Markers exhibiting two alleles are pursued. A baby with trisomy is expected to show either three alleles, evident by three peaks in a 1:1:1 ratio or two alleles in a 2:1 ratio. FIG. 3B depicts a sample from maternal serum. Markers exhibiting three alleles are informative. Maternal serum from a woman carrying a baby with trisomy is expected to exhibit three alleles, evident by two equal peaks with a third smaller peak if the trisomy occurred during meiosis I (75% of T21 cases) or three alleles with different areas if the trisomy occurred during meiosis II (20% of T21 cases) where areas are: peak, x, and peak+2x. FIG. 3C depicts analysis of a sample from maternal serum. Markers exhibiting three alleles are informative. Maternal serum from a woman with a normal baby with three alleles has three different areas where areas are: peak, x, and peak+x.

Interpretation of Results

For the case of the minimum heterozygosity, where both SNP1 and SNP2 are heterozygous at their respective loci at a rate of 25%, if 96 tandem SNPs are assayed, an average of 43 markers (44.5%) are expected to be heterozygous (two haplotypes) in the mother. The mother's expected heterozygosity is calculated using the following formula:

$$H = 1 - \Sigma p_i^2$$

for i=1 to k alleles where $p_i$=estimated allele frequency.

The allele frequencies at each SNP loci are expected to be 85% and 15% for the majority and minority alleles, respectively, assuming Hardy-Weinberg equilibrium. The desired third haplotype is expected to be present at an average of 6.4 markers (15%) of per maternal-fetal sample tested. Because most loci have a heterozygosity value greater than 25%, for every maternal-fetal sample tested using the panel of 96 tandem SNP assays, greater than about 6.4 markers are most informative. Thus, while a panel of 96 tandem SNPs may be used, 6 or 7 of those tandem SNPs may be informative for any one specific maternal-fetal sample tested, and a 'positive' result from any one of those tandem SNPs is informative.

Finally, in order to diagnose a trisomy, a "positive" tandem SNPs should be identified on both the p and the q arm of chromosome 21. Because of the comparative nature of the basic approach, the tandem SNP assay is predicted to have a detection rate of 95% (those that occur during maternal meiosis) for trisomy 21. If paternal samples are available, non-disjunctions that occur during paternal meiosis can also be detected. Thus, detection rates would be higher (about ~99%) with a 0% false positive rate.

Example 5

Tandem SNPs and Primers

Table 2 provides exemplary tandem SNPs of the invention and primers that can be used in the methods of the invention to detect the tandem SNPs. Certain embodiments of the present invention provide primers that can be used to amplify at least one of the SNPs. Certain embodiments of the present invention provide nucleic acid sequences that comprise at least one of the SNPs, e.g., at least one of the tandem SNPs.

TABLE 2

1) Whole sequence ::: rs432114-rs365433 CC/CT/GC/GT

AACAAATCTTCATCTTGGAATAGCCTGTGAGAATGCCTAATCATCTACGAATgTTACTTT

GGCACCATCTACTGGACAgATTAAATAACAACCAACTCACTGTGGATTAGACCTACTTCT

ATTTCAG (SEQ ID NO: 1)

| OLIGO | start | len | tm | gc % | any | 3' | seq (SEQ ID NOs: 2, 3) |
|---|---|---|---|---|---|---|---|
| LEFT PRIMER | 20 | 20 | 55.08 | 45.00 | 3.00 | 2.00 | ATAGCCTGTGAGAATGCCTA |
| RIGHT PRIMER | 107 | 20 | 55.30 | 45.00 | 5.00 | 0.00 | ATCCACAGTGAGTTGGTTGT |

SEQUENCE SIZE: 127
INCLUDED REGION SIZE: 127

PRODUCT SIZE: 88, PAIR ANY COMPL: 5.00, PAIR 3' COMPL: 1.00

```
  1 AACAAATCTTCATCTTGGAATAGCCTGTGAGAATGCCTAATCATCTACGAATgTTACTTT
                       >>>>>>>>>>>>>>>>>>>>

61 GGCACCATCTACTGGACAgATTAAATAACAACCAACTCACTGTGGATTAGACCTACTTCT
                                           <<<<<<<<<<<<<<<<<<<<

121 ATTTCAG
```

2) Whole sequence ::: rs7277033-rs2110153 CC/CT/TC/TT

PCR did not work
TTCCTGGAAAACAAAAGTATTTCTTTCATAGCCCAGCTAGCAtGATAAATCAGCgAGTCA

GAATTCTAGCTTTGTTGTAAGGTT (SEQ ID NO: 4)

| OLIGO | start | len | tm | gc % | any | 3' | seq (SEQ ID NOs: 5, 6) |
|---|---|---|---|---|---|---|---|
| LEFT PRIMER | 2 | 20 | 51.63 | 30.00 | 5.00 | 3.00 | TCCTGGAAAACAAAAGTATT |
| RIGHT PRIMER | 84 | 21 | 51.36 | 33.33 | 4.00 | 0.00 | AACCTTACAACAAAGCTAGAA |

SEQUENCE SIZE: 84
INCLUDED REGION SIZE: 84

PRODUCT SIZE: 83, PAIR ANY COMPL: 3.00, PAIR 3' COMPL: 2.00

```
  1 TTCCTGGAAAACAAAAGTATTTCTTTCATAGCCCAGCTAGCAtGATAAATCAGCgAGTCA
     >>>>>>>>>>>>>>>>>>>>

61 GAATTCTAGCTTTGTTGTAAGGTT
       <<<<<<<<<<<<<<<<<<<<<
```

3) Whole sequence ::: rs2822654-rs1882882 AA/AG/CA/CG

CACTAAGCCTTGGGGATCCAGCTGCTTaAGGACTAAGACCgTATCTAGCTCCTTTTAGTA

TTTCCACAGCA (SEQ ID NO: 7)

TABLE 2-continued

```
OLIGO          start   len   tm     gc %    any    3'    seq (SEQ ID NOs: 8, 9)

LEFT PRIMER     2      20    60.46  55.00   6.00   2.00  ACTAAGCCTTGGGGATCCAG
RIGHT PRIMER   71      21    54.78  38.10   3.00   0.00  TGCTGTGGAAATACTAAAAGG

SEQUENCE SIZE: 71
INCLUDED REGION SIZE: 71

PRODUCT SIZE: 70, PAIR ANY COMPL: 4.00, PAIR 3' COMPL: 0.00

1 CACTAAGCCTTGGGGATCCAGCTGCTTaAGGACTAAGACCgTATCTAGCTCCTTTTAGTA
       >>>>>>>>>>>>>>>>>>>>                            <<<<<<<<<<

61 TTTCCACAGCA
       <<<<<<<<<<
```

4) Whole sequence ::: rs368657-rs376635 AA/AG/GA/GG

TCCTCCAGAGGTAATCCTGTGATCAGCACTAACaCCACATACCAGCCCTTTCATCAGCTT

GTTGGAGAAGCATCTTTACTTCCCgCCAAGCAGTGACCTagataccatctcacaccagtt agaatcaggatcattaaaaagtcaagaaaaaacag (SEQ ID NO: 10)

```
OLIGO          start   len   tm     gc %    any    3'    seq (SEQ ID NOs: 11, 12)

LEFT PRIMER     3      20    55.20  50.00   5.00   3.00  CTCCAGAGGTAATCCTGTGA
RIGHT PRIMER  117      21    55.10  47.62   5.00   2.00  tggtgtgagatggtatctAGG

SEQUENCE SIZE: 155
INCLUDED REGION SIZE: 155

PRODUCT SIZE: 115, PAIR ANY COMPL: 3.00, PAIR 3' COMPL: 2.00

1 TCCTCCAGAGGTAATCCTGTGATCAGCACTAACaCCACATACCAGCCCTTTCATCAGCTT
         >>>>>>>>>>>>>>>>>>>>

61 GTTGGAGAAGCATCTTTACTTCCCgCCAAGCAGTGACCTagataccatctcacaccagtt
                                                 <<<<<<<<<<<<<<<<<<<<<

121 agaatcaggatcattaaaaagtcaagaaaaaacag
```

5) Whole sequence ::: rs2822731-rs2822732 AA/AG/GA/GG

TCCAAGTATAATCCATGAATCTTGTTTAAATATAGATCAAaTAAACCACTATACCAAAAA

CATCAAAAGACAACTGGGTAAATTTTTTAAATGACTAGCTATTTGATGTTAAgGAAGTAA

TGTTACTCTCTTATATACAATTTGAA (SEQ ID NO: 13)

```
OLIGO          start   len   tm     gc %    any    3'    seq (SEQ ID NOs: 14, 15)

LEFT PRIMER     6      22    50.35  27.27   6.00   3.00  GTATAATCCATGAATCTTGTTT
RIGHT PRIMER  146      22    45.69  22.73   6.00   1.00  TTCAAATTGTATATAAGAGAGT

SEQUENCE SIZE: 146
INCLUDED REGION SIZE: 146

PRODUCT SIZE: 141, PAIR ANY COMPL: 4.00, PAIR 3' COMPL: 2.00

1 TCCAAGTATAATCCATGAATCTTGTTTAAATATAGATCAAaTAAACCACTATACCAAAAA
          >>>>>>>>>>>>>>>>>>>>>>

61 CATCAAAAGACAACTGGGTAAATTTTTTAAATGACTAGCTATTTGATGTTAAgGAAGTAA

121 TGTTACTCTCTTATATACAATTTGAA
         <<<<<<<<<<<<<<<<<<<<<<
```

6) Whole sequence ::: rs6516899-rs455221 CC/CT/TC/TT

ATGGAACCGAAACTTCAAGTAGTTTCATAcGTATCACATTGACAGTTTTCTCTAAGTTTT

CtGGTCTTATGACTCGTTGTTTCATTATTAAAACTGTGCCAGTGTATGCATAGGGCTTAG

AAATTTTTTAAT (SEQ ID NO: 16)

```
OLIGO          start   len   tm     gc %    any    3'    seq (SEQ ID NOs: 17, 18)

LEFT PRIMER     1      18    53.87  38.89   4.00   3.00  ATGGAACCGAAACTTCAA
RIGHT PRIMER   91      22    52.84  27.27   5.00   1.00  TTAATAATGAAACAACGAGTCA
```

TABLE 2-continued

```
SEQUENCE SIZE: 132
INCLUDED REGION SIZE: 132

PRODUCT SIZE: 91, PAIR ANY COMPL: 4.00, PAIR 3' COMPL: 0.00

1 ATGGAACCGAAACTTCAAGTAGTTTCATAcGTATCACATTGACAGTTTTCTCTAAGTTTT
    >>>>>>>>>>>>>>>>>>>

61 CtGGTCTTATGACTCGTTGTTTCATTATTAAAACTGTGCCAGTGTATGCATAGGGCTTAG
              <<<<<<<<<<<<<<<<<<

121 AAATTTTTTAAT
```

7) Whole sequence ::: rs7275381-rs12627144 GA/GG/TA/TG acaggatccttcctgaagacaccaccttggggagggtgaagGataaagaatttgatcaga aatcaagggtggtgagatacatgttaaggatgaataaactggccttttaggattcttgct aaaAttagacaatgcagaggcaaccacagagtccaag (SEQ ID NO: 19)

| OLIGO | start | len | tm | gc % | any | 3' | seq (SEQ ID NOs: 20, 21) |
|---|---|---|---|---|---|---|---|
| LEFT PRIMER | 10 | 19 | 55.53 | 47.37 | 4.00 | 0.00 | ttcctgaagacaccacctt |
| RIGHT PRIMER | 157 | 18 | 54.94 | 55.56 | 3.00 | 2.00 | cttggactctgtggttgc |

```
SEQUENCE SIZE: 157
INCLUDED REGION SIZE: 157

PRODUCT SIZE: 148, PAIR ANY COMPL: 5.00, PAIR 3' COMPL: 1.00

1 acaggatccttcctgaagacaccaccttggggagggtgaagGataaagaatttgatcaga
              >>>>>>>>>>>>>>>>>>>

61 aatcaagggtggtgagatacatgttaaggatgaataaactggccttttaggattcttgct 121 aaaAttagacaatgcagaggcaaccacagagtccaag
                      <<<<<<<<<<<<<<<<<<
```

8) Whole sequence ::: rs1999288-rs208897 CC/CT/TC

AATTTCCATTAAATCTTGTTCGTTGCTTTACTGAGGCACTGAAGTTACCAATGTTcCACT

GGTTGACCTGCGGGGCTATCTCTAGGTTATGTTACTCCAGAAAATGAATTGTGTATAAAA

GAGGCCTTGGAGGAAGGCGTTTTATTCaCATCAGTTGTTTTGCACATTGCTTA (SEQ ID NO: 22)

| OLIGO | start | len | tm | gc % | any | 3' | seq (SEQ ID NOs: 23, 24) |
|---|---|---|---|---|---|---|---|
| LEFT PRIMER | 30 | 20 | 54.40 | 50.00 | 4.00 | 2.00 | ACTGAGGCACTGAAGTTACC |
| RIGHT PRIMER | 173 | 20 | 54.96 | 35.00 | 4.00 | 0.00 | TAAGCAATGTGCAAAACAAC |

```
SEQUENCE SIZE: 173
INCLUDED REGION SIZE: 173

PRODUCT SIZE: 144, PAIR ANY COMPL: 4.00, PAIR 3' COMPL: 0.00

1 AATTTCCATTAAATCTTGTTCGTTGCTTTACTGAGGCACTGAAGTTACCAATGTTcCACT
                                 >>>>>>>>>>>>>>>>>>>>

61 GGTTGACCTGCGGGGCTATCTCTAGGTTATGTTACTCCAGAAAATGAATTGTGTATAAAA

121 GAGGCCTTGGAGGAAGGCGTTTTATTCaCATCAGTTGTTTTGCACATTGCTTA
                            <<<<<<<<<<<<<<<<<<<<
```

9) Whole sequence ::: rs1475881-rs7275487 CA/CG/GA/GG

PCR did not work
TCGGTTTCAGCAGGAAAGTTATTTTTAATAACTTCCCTGTATTTcTTGGTTTCAGTTATTAATTAACTCATTAATGCTAAA CTTTGTGATCCTAGGTTAAAAAACATATTCAAGATAGCTTCAGAATGTTTGGTATACAAgTAGGTCTGGCTAAATATAAGT

GTTAGCTTT CTCAAGCATC TAAATGCTGG (SEQ ID NO: 25)

| OLIGO | start | len | tm | gc % | any | 3' | seq (SEQ ID NOs: 26, 27) |
|---|---|---|---|---|---|---|---|
| LEFT PRIMER | 10 | 20 | 48.49 | 25.00 | 5.00 | 3.00 | GCAGGAAAGTTATTTTTAAT |
| RIGHT PRIMER | 179 | 21 | 54.70 | 38.10 | 4.00 | 1.00 | TGCTTGAGAAAGCTAACACTT |

TABLE 2-continued

```
SEQUENCE SIZE: 191
INCLUDED REGION SIZE: 191

PRODUCT SIZE: 170, PAIR ANY COMPL: 5.00, PAIR 3' COMPL: 2.00

1 TCGGTTTCAGCAGGAAAGTTATTTTTAATAACTTCCCTGTATTTCTTGGTTTCAGTTATT
              >>>>>>>>>>>>>>>>>>>>

61 AATTAACTCATTAATGCTAAACTTTGTGATCCTAGGTTAAAAAACATATTCAAGATAGCT

121 TCAGAATGTTTGGTATACAAgTAGGTCTGGCTAAATATAAGTGTTAGCTTTCTCAAGCAT
                          <<<<<<<<<<<<<<<<<<<<

181 CTAAATGCTGG

ALTERNATIVE:: (LESS THAN 5 bp APART)
AAGTTATTTTTAATAACTTCCCTGTATTTcTTGGTTTCAGTTATTAATTAACTCATTAAT

GCTAAACTTTGTGATCCTAGGTTAAAAAACATATTCAAGATAGCTTCAGAATGTTTGGTA

TACAAgTAGGTCTGGCTAAATATAAGTGTTAGCTTTCTCAAGCATC (SEQ ID NO: 28)

OLIGO           start    len    tm      gc %    any    3'    seq (SEQ ID NOs: 29, 30)

LEFT PRIMER       6       20   47.68   25.00   6.00   0.00  ATTTTTAATAACTTCCCTGT
RIGHT PRIMER    148       20   49.30   40.00   4.00   0.00  CACTTATATTTAGCCAGACC

SEQUENCE SIZE: 166
INCLUDED REGION SIZE: 166

PRODUCT SIZE: 143, PAIR ANY COMPL: 4.00, PAIR 3' COMPL: 1.00

1 AAGTTATTTTTAATAACTTCCCTGTATTTcTTGGTTTCAGTTATTAATTAACTCATTAAT
          >>>>>>>>>>>>>>>>>>>>

61 GCTAAACTTTGTGATCCTAGGTTAAAAAACATATTCAAGATAGCTTCAGAATGTTTGGTA

121 TACAAgTAGGTCTGGCTAAATATAAGTGTTAGCTTTCTCAAGCATC
                <<<<<<<<<<<<<<<<<<<<

10) Whole sequence ::: rs1735976-rs2827016 AA/AC/GA/GC

ATTCATTGTGTAGAAAGTGCCTGACTCAGTGTTTGGAAATTGTCTGACTTTTCCTCATAT aTAGTGTGGTTTCATGTTATTGTATATAAGAaCTGACATGAACTCTGTTTACAATAATCT

CCCAGTGCCATAAAGACCATAATAAATAATAT (SEQ ID NO: 31)

OLIGO           start    len    tm      gc %    any    3'    seq (SEQ ID NOs: 32, 33)

LEFT PRIMER      27       20   54.11   40.00   4.00   1.00  CAGTGTTTGGAAATTGTCTG
RIGHT PRIMER    129       20   55.17   45.00   3.00   2.00  GGCACTGGGAGATTATTGTA

SEQUENCE SIZE: 152
INCLUDED REGION SIZE: 152

PRODUCT SIZE: 103, PAIR ANY COMPL: 5.00, PAIR 3' COMPL: 1.00

1 ATTCATTGTGTAGAAAGTGCCTGACTCAGTGTTTGGAAATTGTCTGACTTTTCCTCATAT
                                 >>>>>>>>>>>>>>>>>>>>

61 aTAGTGTGGTTTCATGTTATTGTATATAAGAaCTGACATGAACTCTGTTTACAATAATCT
                                              <<<<<<<<<<

121 CCCAGTGCCATAAAGACCATAATAAATAATAT
         <<<<<<<<

2nd group of primers
11) Whole sequence ::: rs447349-rs2824097 CT/TC/TT (156 long)

CACTGGGTCCTGTTGTTAAGTACACATAATACCACaCAGGAGAAAATCAGGCTAATTGTA

AATGGGCAACCTACTTAATTGTTTCATTAAAAAGCATACAGATTACATTTACACTAtAGC

TAGTCTTGTTTGTTTTTTTATTTTGCAAAAGTAATTACGGCCC (SEQ ID NO: 34)

OLIGO           start    len    tm      ac %    any    3'    seq (SEQ ID NOs: 35, 36)

LEFT PRIMER       8       20   47.79   35.00   6.00   2.00  TCCTGTTGTTAAGTACACAT
RIGHT PRIMER    163       18   53.29   44.44   8.00   2.00  GGGCCGTAATTACTTTTG
```

TABLE 2-continued

```
SEQUENCE SIZE: 163
INCLUDED REGION SIZE: 163

PRODUCT SIZE: 156, PAIR ANY COMPL: 5.00, PAIR 3' COMPL: 1.00

1 CACTGGGTCCTGTTGTTAAGTACACATAATACCACaCAGGAGAAAATCAGGCTAATTGTA
        >>>>>>>>>>>>>>>>>>>>

61 AATGGGCAACCTACTTAATTGTTTCATTAAAAAGCATACAGATTACATTTACACTAtAGC

121 TAGTCTTGTTTGTTTTTTTATTTTGCAAAAGTAATTACGGCCC
           <<<<<<<<<<<<<<<<<
```

12) Whole sequence ::: rs418989-rs13047336 AC/AT/CC

CTACTCAGTAGGCACTTTGTGTCTAGAAACTTCTGTGTCAACgGTTTTCCCTCTCTCTGG

AATTCaTCAGGACAGAAGTGATTGGTGTGGTGGAAGAGGGTTGTGSTA (SEQ ID NO: 37)

| OLIGO | start | len | tm | gc % | any | 3' | seq (SEQ ID NOs: 38, 39) |
|---|---|---|---|---|---|---|---|
| LEFT PRIMER | 3 | 21 | 54.50 | 47.62 | 5.00 | 3.00 | ACTCAGTAGGCACTTTGTGTC |
| RIGHT PRIMER | 97 | 18 | 54.95 | 50.00 | 2.00 | 0.00 | TCTTCCACCACACCAATC |

```
SEQUENCE SIZE: 108
INCLUDED REGION SIZE: 108

PRODUCT SIZE: 95, PAIR ANY COMPL: 5.00, PAIR 3' COMPL: 2.00

1 CTACTCAGTAGGCACTTTGTGTCTAGAAACTTCTGTGTCAACgGTTTTCCCTCTCTCTGG
        >>>>>>>>>>>>>>>>>>>>

61 AATTCaTCAGGACAGAAGTGATTGGTGTGGTGGAAGAGGGTTGTGSTA
              <<<<<<<<<<<<<<<<<<
```

13) Whole sequence ::: rs987980-rs987981 AG/GG/GT

TGGCTTTTCAAAGGTAAAATTTACTaAGTGTATTAATATTTTACCAATTTCCAGCCAGGA

GAGTATGAATGTTGCATTATTACATTGCTTTGAAACAAAGCATTAgTCTTAATTCAGAAG

TTTAAATTCAGATGTTAACGTTGC (SEQ ID NO: 40)

| OLIGO | start | len | tm | gc % | any | 3' | seq (SEQ ID NOs: 41, 42) |
|---|---|---|---|---|---|---|---|
| LEFT PRIMER | 1 | 19 | 53.67 | 31.58 | 6.00 | 2.00 | TGGCTTTTCAAAGGTAAAA |
| RIGHT PRIMER | 144 | 21 | 54.59 | 33.33 | 6.00 | 3.00 | GCAACGTTAACATCTGAATTT |

```
SEQUENCE SIZE: 144
INCLUDED REGION SIZE: 144

PRODUCT SIZE: 144, PAIR ANY COMPL: 6.00, PAIR 3' COMPL: 3.00

1 TGGCTTTTCAAAGGTAAAATTTACTaAGTGTATTAATATTTTACCAATTTCCAGCCAGGA
        >>>>>>>>>>>>>>>>>>>

61 GAGTATGAATGTTGCATTATTACATTGCTTTGAAACAAAGCATTAgTCTTAATTCAGAAG

121 TTTAAATTCAGATGTTAACGTTGC
         <<<<<<<<<<<<<<<<<<<<<
```

14) Whole sequence ::: rs4143392-rs4143391 CA/CG/GA/GG

TAAGTATTGAAGAAAGGAGAATTTAAATTACTTCATATACctgataaaggaaaacatata

CAAGGCAAATAAACATCTTAGATCATGACATATAAAATAATAGATTATTA (SEQ ID NO: 43)

| OLIGO | start | len | tm | gc % | any | 3' | seq (SEQ ID NOs: 44, 45) |
|---|---|---|---|---|---|---|---|
| LEFT PRIMER | 7 | 20 | 49.56 | 25.00 | 4.00 | 4.00 | TTGAAGAAAGGAGAATTTAA |
| RIGHT PRIMER | 98 | 22 | 45.86 | 22.73 | 6.00 | 3.00 | ATTTTATATGTCATGATCTAAG |

```
SEQUENCE SIZE: 110
INCLUDED REGION SIZE: 110

PRODUCT SIZE: 92, PAIR ANY COMPL: 4.00, PAIR 3' COMPL: 1.00

1 TAAGTATTGAAGAAAGGAGAATTTAAATTACTTCATATACctgataaaggaaaacatata
            >>>>>>>>>>>>>>>>>>>>
```

TABLE 2-continued

```
 61 CAAGGCAAATAAACATCTTAGATCATGACATATAAAATAATAGATTATTA
       <<<<<<<<<<<<<<<<<<<
```

15) Whole sequence ::: rs1691324-rs13050434 CG/TA/TG
(4 bp apart for right primer)

TGCAGAGATTACAGGTGTGAGCCACCGTGCCCAGCCTCATAACcGTTTCAACTACTTTTT

CACTTGACAAGCAGATGTGAAGTTAACAAAGTCACCCATATTTGAAATAAAGATAGTATA

TTCCTGGGGtAGGCAGAGGCAGTTGAGGATCATGAAATAACTATG (SEQ ID NO: 46)

```
OLIGO         start   len   tm     gc %    any    3'    seq (SEQ ID NOs: 47, 48)

LEFT PRIMER     4      19   49.78  47.37   4.00   4.00  AGAGATTACAGGTGTGAGC
RIGHT PRIMER  153      19   54.61  47.37   4.00   0.00  ATGATCCTCAACTGCCTCT
```

SEQUENCE SIZE: 165
INCLUDED REGION SIZE: 165

PRODUCT SIZE: 150, PAIR ANY COMPL: 4.00, PAIR 3' COMPL: 2.00

```
   1 TGCAGAGATTACAGGTGTGAGCCACCGTGCCCAGCCTCATAACcGTTTCAACTACTTTTT
         >>>>>>>>>>>>>>>>>>>

61 CACTTGACAAGCAGATGTGAAGTTAACAAAGTCACCCATATTTGAAATAAAGATAGTATA

121 TTCCTGGGGtAGGCAGAGGCAGTTGAGGATCATGAAATAACTATG
                   <<<<<<<<<<<<<<<<<<<
```

16) Whole sequence ::: rs11909758-rs9980111 (159 bp long) AG/AT/GT

TGCAATGAAACTCAAAAGAGAAAAGTTAACAGGTGCAAaAGGTAGTTTTATTATAAAAGG

AGGGTAGGCAACAAGAATATGTTTAATTTTTCTTCCTTTTCATGAGTAAGGACAAGAGTg

TCATATATGTGaatattttatttaattttaaGTAGAAATCTGTTTTTAAAATATGGG (SEQ ID NO: 49)

```
OLIGO         start   len   tm     gc %    any    3'    seq (SEQ ID NOs: 50, 51)

LEFT PRIMER     6      20   49.91  30.00   3.00   0.00  TGAAACTCAAAAGAGAAAAG
RIGHT PRIMER  164      20   42.77  20.00   6.00   4.00  ACAGATTTCTACttaaaatt
```

SEQUENCE SIZE: 178
INCLUDED REGION SIZE: 178

PRODUCT SIZE: 159, PAIR ANY COMPL: 6.00, PAIR 3' COMPL: 3.00

```
   1 TGCAATGAAACTCAAAAGAGAAAAGTTAACAGGTGCAAaAGGTAGTTTTATTATAAAAGG
           >>>>>>>>>>>>>>>>>>>>

61 AGGGTAGGCAACAAGAATATGTTTAATTTTTCTTCCTTTTCATGAGTAAGGACAAGAGTg

121 TCATATATGTGaatattttatttaattttaaGTAGAAATCTGTTTTTAAAATATGGG
                       <<<<<<<<<<<<<<<<<<<<
```

17) Whole sequence ::: rs854613-rs854614 AA/AG/TG

CCACCATTCATCAAAACTTTGATACTGGACTCAATTGTGAATTTGaCTTGAAATTTGATA

ATGCTTTTGTTTTACTgTTCTGCTCAGCAAAATAGTACATGT (SEQ ID NO: 52)

```
OLIGO         start   len   tm     gc %    any    3'    seq (SEQ ID NOs: 53, 54)

LEFT PRIMER    12      20   49.40  35.00   6.00   1.00  CAAAACTTTGATACTGGACT
RIGHT PRIMER  102      19   46.05  31.58   6.00   1.00  ACATGTACTATTTTGCTGA
```

SEQUENCE SIZE: 102
INCLUDED REGION SIZE: 102

PRODUCT SIZE: 91, PAIR ANY COMPL: 5.00, PAIR 3' COMPL: 1.00

```
   1 CCACCATTCATCAAAACTTTGATACTGGACTCAATTGTGAATTTGaCTTGAAATTTGATA
                 >>>>>>>>>>>>>>>>>>>>

61 ATGCTTTTGTTTTACTgTTCTGCTCAGCAAAATAGTACATGT
                       <<<<<<<<<<<<<<<<<<<
```

3$^{rd}$ group---order primers from 18-25

TABLE 2-continued

18) Whole sequence ::: rs2826225-rs2826226 AA/GA/GC

GCCTGCATAAAGTGAGGATGGTGTAGTAATTGGGTATCTCCAGTTATAAACACAAaAAGC

ATGATAGAGCTGGGAcTGTGATTGCAGGAAAGCAATAGTCACTCCAAAAGGAGATCCTCA

TGATATGAATACGGAAGAAACAATATTTCCTGCTAATGTAGTAGCC (SEQ ID NO: 55)

| OLIGO | start | len | tm | gc % | any | 3' | seq (SEQ ID NOs: 56, 57) |
|---|---|---|---|---|---|---|---|
| LEFT PRIMER | 2 | 20 | 58.17 | 50.00 | 4.00 | 0.00 | CCTGCATAAAGTGAGGATGG |
| RIGHT PRIMER | 120 | 21 | 59.27 | 47.62 | 6.00 | 0.00 | TGAGGATCTCCTTTTGGAGTG |

SEQUENCE SIZE: 166
INCLUDED REGION SIZE: 166

PRODUCT SIZE: 119, PAIR ANY COMPL: 6.00, PAIR 3' COMPL: 3.00

```
  1 GCCTGCATAAAGTGAGGATGGTGTAGTAATTGGGTATCTCCAGTTATAAACACAAaAAGC
    >>>>>>>>>>>>>>>>>>>>

61 ATGATAGAGCTGGGAcTGTGATTGCAGGAAAGCAATAGTCACTCCAAAAGGAGATCCTCA
                                      <<<<<<<<<<<<<<<<<<<<<

121 TGATATGAATACGGAAGAAACAATATTTCCTGCTAATGTAGTAGCC
```

19) Whole sequence ::: rs2826842-rs232414 CA/CG/TA/TG

GCAAAGGGGTACTCTATGTAATGAAcATgacctggcagtactgacatctcctgagggact gttagaagtgcagactcttgtatcttttctcaagtctatgaaatctagacttcattttaa caagatgacccgatatttacatacacattaaagt (SEQ ID NO: 58)

| OLIGO | start | len | tm | gc % | any | 3' | seq (SEQ ID NOs: 59, 60) |
|---|---|---|---|---|---|---|---|
| LEFT PRIMER | 1 | 20 | 52.04 | 45.00 | 4.00 | 2.00 | GCAAAGGGGTACTCTATGTA |
| RIGHT PRIMER | 135 | 20 | 53.29 | 35.00 | 4.00 | 3.00 | tatcgggtcatcttgttaaa |

SEQUENCE SIZE: 154
INCLUDED REGION SIZE: 154

PRODUCT SIZE: 135, PAIR ANY COMPL: 3.00, PAIR 3' COMPL: 2.00

```
  1 GCAAAGGGGTACTCTATGTAATGAAcATgacctggcagtactgacatctcctgagggact
    >>>>>>>>>>>>>>>>>>>>

61 gttagaagtgcagactcttgtatcttttctcaagtctatgaaatctagacttcattttaa
                                                         <<<<<

121 caagatgacccgatatttacatacacattaaagt
    <<<<<<<<<<<<<<<
```

20) Whole sequence ::: rs1980969-rs1980970 AA/AG/TA/TG

GTATCTAACAAAGCTCTGTCCAAAATTTTGAATTTCTCGTTAAAaGCATCATGATTATAG

AACAGAGGTTACAATCAATTATTCAGTCACACAATCACTCTCATCAGTCATTAAGGTGCg

TACCTGGTGTTCCAGTTATTCAGTGTGGTATAACAAACTACCTGGAACTTAATG (SEQ ID NO: 61)

| OLIGO | start | len | tm | gc % | any | 3' | seq (SEQ ID NOs: 62, 63) |
|---|---|---|---|---|---|---|---|
| LEFT PRIMER | 4 | 22 | 56.88 | 36.36 | 8.00 | 2.00 | TCTAACAAAGCTCTGTCCAAAA |
| RIGHT PRIMER | 148 | 21 | 56.12 | 42.86 | 3.00 | 1.00 | CCACACTGAATAACTGGAACA |

SEQUENCE SIZE: 174
INCLUDED REGION SIZE: 174

PRODUCT SIZE: 145, PAIR ANY COMPL: 4.00, PAIR 3' COMPL: 1.00

```
  1 GTATCTAACAAAGCTCTGTCCAAAATTTTGAATTTCTCGTTAAAaGCATCATGATTATAG
       >>>>>>>>>>>>>>>>>>>>>>

61 AACAGAGGTTACAATCAATTATTCAGTCACACAATCACTCTCATCAGTCATTAAGGTGCg

121 TACCTGGTGTTCCAGTTATTCAGTGTGGTATAACAAACTACCTGGAACTTAATG
            <<<<<<<<<<<<<<<<<<<<<
```

4th group

TABLE 2-continued

21) Whole sequence ::: rs189900-rs2221492

AGAGTGGTTAAGTGACTTGATCAATTCCTCA GGTGGGGATTCAAGCTCTTAAAGCTGTAG

ACTATGTCGTCCAAACAAAcACTGACATGAATATGACTTCCAATAGGCAAGAAAAGAGGC

CTAGGTCgAGATACTGCAAGACATGCAAGCAATCTAGTAATGGCATAAAACCTGCTATCC

GAATTGGCTAAAATTATGTATT (SEQ ID NO: 64)

| OLIGO | start | len | tm | gc % | any | 3' | seq (SEQ ID NOs: 65, 66) |
|---|---|---|---|---|---|---|---|
| LEFT PRIMER | 32 | 20 | 59.13 | 50.00 | 4.00 | 2.00 | GGTGGGGATTCAAGCTCTTA |
| RIGHT PRIMER | 180 | 22 | 59.38 | 40.91 | 5.00 | 3.00 | GGATAGCAGGTTTTATGCCATT |

SEQUENCE SIZE: 202
INCLUDED REGION SIZE: 202

PRODUCT SIZE: 149, PAIR ANY COMPL: 4.00, PAIR 3' COMPL: 1.00

```
  1 AGAGTGGTTAAGTGACTTGATCAATTCCTCAGGTGGGGATTCAAGCTCTTAAAGCTGTAG
                                   >>>>>>>>>>>>>>>>>>>>

61 ACTATGTCGTCCAAACAAAcACTGACATGAATATGACTTCCAATAGGCAAGAAAAGAGGC

121 CTAGGTCgAGATACTGCAAGACATGCAAGCAATCTAGTAATGGCATAAAACCTGCTATCC
                                       <<<<<<<<<<<<<<<<<<<<<<

181 GAATTGGCTAAAATTATGTATT
```

22) Whole sequence ::: rs2827920-rs2827921

TTCTTTCTCACACAATGGGTTCCATTCCCACTACTACTCCATTCAAATTGAAGTGCCTTC aATGATTATTAAAAAACTCTCTTTAAAATAGCTCACGTAACCTTACATCCTTTGACTGAG

GCTCAACTCATGTCAATGCTTCAGTATCAACTTTTC (SEQ ID NO: 67)

| OLIGO | start | len | tm | gc % | any | 3' | seq (SEQ ID NOs: 68, 69) |
|---|---|---|---|---|---|---|---|
| LEFT PRIMER | 14 | 21 | 59.93 | 47.62 | 7.00 | 0.00 | AATGGGTTCCATTCCCACTAC |
| RIGHT PRIMER | 125 | 20 | 58.96 | 50.00 | 7.00 | 1.00 | TGAGCCTCAGTCAAAGGATG |

SEQUENCE SIZE: 156
INCLUDED REGION SIZE: 156

PRODUCT SIZE: 112, PAIR ANY COMPL: 4.00, PAIR 3' COMPL: 1.00

```
  1 TTCTTTCTCACACAATGGGTTCCATTCCCACTACTACTCCATTCAAATTGAAGTGCCTTC
                   >>>>>>>>>>>>>>>>>>>>>

61 aATGATTATTAAAAAACTCTCTTTAAAATAGCTCAcGTAACCTTACATCCTTTGACTGAG
                                         <<<<<<<<<<<<<<<

121 GCTCAACTCATGTCAATGCTTCAGTATCAACTTTTC
       <<<<<
```

23) Whole sequence ::: rs198047-rs2827935

ATTTGTAATAACATTTAGTAAGTATTTATTTGAGGAGTTTGAATTTTGTTCTTGTTTATC

TTGTTCTCTTTCTTcGTAGATTAGTTGGTGTTAACATCAATAGGATAACCCTTTCTTTCA

GCATATGTGAATGAAATaAACCAATTATTGCCACTTTCCAGGTTAACCAGAATATACATA

GATACGAGGACAGTGGACTGTT (SEQ ID NO: 70)

| OLIGO | start | len | tm | gc % | any | 3' | seq (SEQ ID NOs: 71, 72) |
|---|---|---|---|---|---|---|---|
| LEFT PRIMER | 30 | 22 | 56.07 | 31.82 | 4.00 | 1.00 | TTGAGGAGTTTGAATTTTGTTC |
| RIGHT PRIMER | 164 | 20 | 57.22 | 40.00 | 3.00 | 1.00 | AACCTGGAAAGTGGCAATAA |

SEQUENCE SIZE: 202
INCLUDED REGION SIZE: 202

PRODUCT SIZE: 135, PAIR ANY COMPL: 3.00, PAIR 3' COMPL: 2.00

```
  1 ATTTGTAATAACATTTAGTAAGTATTTATTTGAGGAGTTTGAATTTTGTTCTTGTTTATC
                                   >>>>>>>>>>>>>>>>>>>>>>
```

TABLE 2-continued

```
 61 TTGTTCTCTTTCTTcGTAGATTAGTTGGTGTTAACATCAATAGGATAACCCTTTCTTTCA

121 GCATATGTGAATGAAATaAACCAATTATTGCCACTTTCCAGGTTAACCAGAATATACATA
                      <<<<<<<<<<<<<<<<<<<<<<

181 GATACGAGGACAGTGGACTGTT
```

24) Whole sequence ::: rs9978999-rs9979175 tagggcagagagagcaagcaagctctctaccttctcatataagggcactaatcccaccat gaaggcgccactgtcatgacCtgattatgtcacaaagaccccggggcaaatattaccact Gtgaggagtacagttttagcatgtgaattttggaagaacacaaacatttag (SEQ ID NO: 73)

```
OLIGO          start    len    tm      gc %    any    3'    seq (SEQ ID NOs: 74, 75)

LEFT PRIMER     14       21    58.50   52.38   4.00   0.00  gcaagcaagctctctaccttc
RIGHT PRIMER   160       22    59.98   36.36   4.00   2.00  tgttcttccaaaattcacatgc

SEQUENCE SIZE: 171
INCLUDED REGION SIZE: 171

PRODUCT SIZE: 147, PAIR ANY COMPL: 3.00, PAIR 3' COMPL: 0.00

1 tagggcagagagagcaagcaagctctctaccttctcatataagggcactaatcccaccat
                   >>>>>>>>>>>>>>>>>>>>>

61 gaaggcgccactgtcatgacCtgattatgtcacaaagaccccggggcaaatattaccact

121 Gtgaggagtacagttttagcatgtgaattttggaagaacacaaacatttag
                          <<<<<<<<<<<<<<<<<<<<<<
```

25) Whole sequence ::: rs1034346-rs12481852

ATTCTAATTTTAAATATCATTGATGTAGAACATTCTATTTCACTATTCCTTCATTTTATT aTTATGGGAAATTATATACAGTTCTCCAGATTTTTAAAGCCTTGCTAACATGTTTTAAGT

CACACAAATATTCTCCTGTGGGAAAATGACAGTAATTTAGTGTGCAACAATTATATAGAA

CTATTTTTCAAACTT (SEQ ID NO: 76)

```
OLIGO          start    len    tm      gc %    any    3'    seq (SEQ ID NOs: 77, 78)

LEFT PRIMER     37       21    50.04   23.81   2.00   0.00  ATTTCACTATTCCTTCATTTT
RIGHT PRIMER   173       22    50.19   27.27   6.00   3.00  TAATTGTTGCACACTAAATTAC

SEQUENCE SIZE: 195
INCLUDED REGION SIZE: 195

PRODUCT SIZE: 137, PAIR ANY COMPL: 4.00, PAIR 3' COMPL: 2.00

1 ATTCTAATTTTAAATATCATTGATGTAGAACATTCTATTTCACTATTCCTTCATTTTATT
                                           >>>>>>>>>>>>>>>>>>>>>

61 aTTATGGGAAATTATATACAGTTCTCCAGATTTTTAAAGCCTTGCTAACATGTTTTAAGT

121 CACACAAATATTCTcCTGTGGGAAAATGACAGTAATTTAGTGTGCAACAATTATATAGAA
                          <<<<<<<<<<<<<<<<<<<<<<

181 CTATTTTTCAAACTT
```

5$^{th}$ group

26) Whole sequence ::: rs7509629-rs2828358

ACTGTCATGGACTTAAACAATTGTCTTTGAATTGTCTTTTTTCATACTTTTATTTGCATC

TTTcCACTAAAAAGATGgCACAAAGTAATCCAGTTTACATTTTTTACCATGTAATTCCA
TATTACTTTTTCCTGAAA (SEQ ID NO: 79)

```
OLIGO          start    len    tm      gc %    any    3'    seq (SEQ ID NOs: 80, 81)

LEFT PRIMER     1        20    50.46   35.00   4.00   0.00  ACTGTCATGGACTTAAACAA
RIGHT PRIMER  137        22    53.49   27.27   4.00   0.00  TTCAGGAAAAAGTAATATGGAA

SEQUENCE SIZE: 138
INCLUDED REGION SIZE: 138
```

TABLE 2-continued

PRODUCT SIZE: 137, PAIR ANY COMPL: 4.00, PAIR 3' COMPL: 0.00

```
  1 ACTGTCATGGACTTAAACAATTGTCTTTGAATTGTCTTTTTTCATACTTTTATTTGCATC
    >>>>>>>>>>>>>>>>>>>>>

61 TTTcCACTAAAAAGATGgCACAAAGTAATCCTAGTTTACATTTTTTACCATGTAATTCCA
                                                         <<<<<

121 TATTACTTTTTCCTGAAA
    <<<<<<<<<<<<<<<<
```

6<sup>th</sup> group

27) Whole sequence ::: rs4817013-rs7277036 aaagaaaaaaaagccacagaaatcagtcctagagaaaacCgatctatgagctgcctgaAa ataattataaaataactatcataaaaatgcccagtgagatataagaaaacacagacaac (SEQ ID NO: 82)

| OLIGO | start | len | tm | gc % | any | 3' | seq (SEQ ID NOs: 83, 84) |
|---|---|---|---|---|---|---|---|
| LEFT PRIMER | 8 | 21 | 56.10 | 38.10 | 4.00 | 2.00 | aaaaagccacagaaatcagtc |
| RIGHT PRIMER | 107 | 22 | 55.60 | 36.36 | 4.00 | 2.00 | ttcttatatctcactgggcatt |

SEQUENCE SIZE: 119
INCLUDED REGION SIZE: 119

PRODUCT SIZE: 100, PAIR ANY COMPL: 5.00, PAIR 3' COMPL: 1.00

```
  1 aaagaaaaaaaagccacagaaatcagtcctagagaaaacCgatctatgagctgcctgaAa
            >>>>>>>>>>>>>>>>>>>>>

61 ataattataaaataactatcataaaaatgcccagtgagatataagaaaacacagacaac
                        <<<<<<<<<<<<<<<<<<<<<<
```

28) Whole sequence ::: rs9981121-rs2829696

CAAGGTCAGAGAAGTTATCTTGGATGGTAGAAGAGAAGAAAGGAGAAGAAaGGATAAGCA

GAAAATCAAAAAGGGCATAAAAAAATTACTGGgGAAAATAATTCTTAGTCACTCACCATT

TCTTATGTTTGTGAAAACAGAAA (SEQ ID NO: 85)

| OLIGO | start | len | tm | gc % | any | 3' | seq (SEQ ID NOs: 86, 87) |
|---|---|---|---|---|---|---|---|
| LEFT PRIMER | 22 | 22 | 56.24 | 45.45 | 2.00 | 0.00 | GGATGGTAGAAGAGAAGAAAGG |
| RIGHT PRIMER | 134 | 22 | 55.74 | 31.82 | 4.00 | 1.00 | TCACAAACATAAGAAATGGTGA |

SEQUENCE SIZE: 143
INCLUDED REGION SIZE: 143

PRODUCT SIZE: 113, PAIR ANY COMPL: 3.00, PAIR 3' COMPL: 0.00

```
  1 CAAGGTCAGAGAAGTTATCTTGGATGGTAGAAGAGAAGAAAGGAGAAGAAaGGATAAGCA
                          >>>>>>>>>>>>>>>>>>>>>>

61 GAAAATCAAAAAGGGCATAAAAAAATTACTGGgGAAAATAATTCTTAGTCACTCACCATT
                                                         <<<<<<<

121 TCTTATGTTTGTGAAAACAGAAA
    <<<<<<<<<<<<<<<
```

29) Whole sequence ::: rs455921-rs2898102 gaccacaattcacaaatgcaaagatgcavaccaacctaagtggccaCtgactaatgaga ggataaagaagatgtggcatatataTatcagggactactactcagccattacaaggaaca aaataatgtcttttgc (SEQ ID NO: 88)

| OLIGO | start | len | tm | gc % | any | 3' | seq (SEQ ID NOs: 89, 90) |
|---|---|---|---|---|---|---|---|
| LEFT PRIMER | 17 | 20 | 59.85 | 45.00 | 4.00 | 0.00 | tgcaaagatgcagaaccaac |
| RIGHT PRIMER | 123 | 22 | 59.63 | 36.36 | 2.00 | 1.00 | ttttgttccttgtaatggctga |

SEQUENCE SIZE: 136
INCLUDED REGION SIZE: 136

PRODUCT SIZE: 107, PAIR ANY COMPL: 5.00, PAIR 3' COMPL: 1.00

TABLE 2-continued

```
  1gaccacaattcacaaatgcaaagatgcagaaccaacctaagtggccaCtgactaatgaga
                 >>>>>>>>>>>>>>>>>>>>

61ggataaagaagatgtggcatatataTatcagggactactactcagccattacaaggaaca
                                   <<<<<<<<<<<<<<<<<<<<<

121aaataatgtcttttgc
```

30) Whole sequence ::: rs2898102-rs458848 gaccacaattcacaaatgcaaagatgcagaaccaacctaagtggccactgactaatgaga ggataaagaagatgtggcatatataCatcagggactactTctcagccattacaaggaaca aaataatgtcttttgcaacaacttggatagagctggaggc (SEQ ID NO: 91)

| OLIGO | start | len | tm | gc % | any | 3' | seq (SEQ ID NOs: 92, 93) |
|---|---|---|---|---|---|---|---|
| LEFT PRIMER | 17 | 20 | 59.85 | 45.00 | 4.00 | 0.00 | tgcaaagatgcagaaccaac |
| RIGHT PRIMER | 160 | 21 | 59.86 | 52.38 | 4.00 | 3.00 | gcctccagctctatccaagtt |

SEQUENCE SIZE: 160
INCLUDED REGION SIZE: 160

PRODUCT SIZE: 144, PAIR ANY COMPL: 4.00, PAIR 3' COMPL: 3.00

```
  1gaccacaattcacaaatgcaaagatgcagaaccaacctaagtggccactgactaatgaga
                 >>>>>>>>>>>>>>>>>>>>

61ggataaagaagatgtggcatatataCatcagggactactTctcagccattacaaggaaca

121aaataatgtcttttgcaacaacttggatagagctggaggc
                       <<<<<<<<<<<<<<<<<<<<<
```

31) Whole sequence ::: rs961301-rs2830208

AATCCTAGACCTTGGATTGCAAGAGACTCCTTAATATCTTCCCATGTCCACATTTcCTTC

ACATAGTTTGAATGTGGCTTCTATTATATACAGATACAAGATTCAAATCCAACCTCTAtG

ATGACTGGTCTTGTGAATAAGCAGAAGAGGCACTAACAAT (SEQ ID NO: 94)

| OLIGO | start | len | tm | gc % | any | 3' | seq (SEQ ID NOs: 95, 96) |
|---|---|---|---|---|---|---|---|
| LEFT PRIMER | 29 | 22 | 57.95 | 40.91 | 4.00 | 2.00 | CCTTAATATCTTCCCATGTCCA |
| RIGHT PRIMER | 160 | 22 | 57.35 | 40.91 | 3.00 | 0.00 | ATTGTTAGTGCCTCTTCTGCTT |

SEQUENCE SIZE: 160
INCLUDED REGION SIZE: 160

PRODUCT SIZE: 132, PAIR ANY COMPL: 3.00, PAIR 3' COMPL: 1.00

```
  1AATCCTAGACCTTGGATTGCAAGAGACTCCTTAATATCTTCCCATGTCCACATTTcCTTC
                             >>>>>>>>>>>>>>>>>>>>>>

61ACATAGTTTGAATGTGGCTTCTATTATATACAGATACAAGATTCAAATCCAACCTCTAtG

121ATGACTGGTCTTGTGAATAAGCAGAAGAGGCACTAACAAT
                       <<<<<<<<<<<<<<<<<<<<<<
```

32) Whole sequence ::: rs2174536-rs458076

AAGAGAAGTGAGGTCAGCAGCTGCAAGCCACCTCCGTCATTTAGAAAAGCTTCaTGATGT

AGTGTGTCGTTTCGATGTGACACTGTCTCACAGAGTTAAAATGATGTtAAGGAACTGTTC

AATGGAAATTTAGAAATTTCTCTTTTTCTCAATTTTAGTGTA (SEQ ID NO: 97)

| OLIGO | start | len | tm | gc % | any | 3' | seq (SEQ ID NOs: 98, 99) |
|---|---|---|---|---|---|---|---|
| LEFT PRIMER | 3 | 20 | 57.31 | 55.00 | 5.00 | 5.00 | GAGAAGTGAGGTCAGCAGCT |
| RIGHT PRIMER | 136 | 22 | 53.92 | 27.27 | 6.00 | 2.00 | TTTCTAAATTTCCATTGAACAG |

SEQUENCE SIZE: 162
INCLUDED REGION SIZE: 162

PRODUCT SIZE: 134, PAIR ANY COMPL: 4.00, PAIR 3' COMPL: 2.00

```
  1AAGAGAAGTGAGGTCAGCAGCTGCAAGCCACCTCCGTCATTTAGAAAAGCTTCaTGATGT
```

TABLE 2-continued

```
      >>>>>>>>>>>>>>>>>>>>
  61 AGTGTGTCGTTTCGATGTGACACTGTCTCACAGAGTTAAAATGATGTtAAGGAACTGTTC
                                                      <<<<<<
 121 AATGGAAATTTAGAAATTTCTCTTTTTCTCAATTTTAGTGTA
     <<<<<<<<<<<<<<
```

33) Whole sequence ::: rs432557-rs1012766

ATGGCTGAATAGTATTCCCTTGTGTATATATCTaTTTATCCTTTTATTCATTGATGGACA

CTTAGGCTGATTTTCTCTCTTCTCATGGCTGGCTTCTCATCACCCTTTGGTCCTCCTGTA

TCCTCgTGTAATAAAGCTCTTCCCCAATATCTCGATAGAT (SEQ ID NO: 100)

```
OLIGO          start   len   tm      gc %    any    3'     seq (SEQ ID NOs: 101, 102)
LEFT PRIMER      3      22   57.77   45.45   9.00   0.00   GGCTGAATAGTATTCCCTTGTG
RIGHT PRIMER   155      20   59.22   50.00   4.00   2.00   TCGAGATATTGGGGAAGAGC
```

SEQUENCE SIZE: 160
INCLUDED REGION SIZE: 160

PRODUCT SIZE: 153, PAIR ANY COMPL: 5.00, PAIR 3' COMPL: 1.00

```
   1 ATGGCTGAATAGTATTCCCTTGTGTATATATCTaTTTATCCTTTTATTCATTGATGGACA
       >>>>>>>>>>>>>>>>>>>>>>
  61 CTTAGGCTGATTTTCTCTCTTCTCATGGCTGGCTTCTCATCACCCTTTGGTCCTCCTGTA

121 TCCTCgTGTAATAAAGCTCTTCCCCAATATCTCGATAGAT
             <<<<<<<<<<<<<<<<<<<<
```

34) Whole sequence ::: rs10222076-rs10222075 cattttaacttgatta cctccacaaagactattccagaataaggttatgttctgaggtat taggggttacAacttcaacatatgaattttgagtggacacaattcaacccatagcaCCTC

CGTGTAAGAGCTGGGAAGGGAAAGTGGCTAAGTTGTGCAAATGTGCACATTGGTTGGAGA

TGATTAACTTCTGGCATGT (SEQ ID NO: 103)

```
OLIGO          start   len   tm      gc %    any    3'     seq (SEQ ID NOs: 104, 105)
LEFT PRIMER     17      22   58.32   45.45   4.00   2.00   cctccacaaagactattccaga
RIGHT PRIMER   146      20   60.76   55.00   4.00   2.00   CACTTTCCCTTCCCAGCTCT
```

SEQUENCE SIZE: 199
INCLUDED REGION SIZE: 199

PRODUCT SIZE: 130, PAIR ANY COMPL: 4.00, PAIR 3' COMPL: 3.00

```
   1 cattttaacttgattacctccacaaagactattccagaataaggttatgttctgaggtat
                     >>>>>>>>>>>>>>>>>>>>>>
  61 taggggttacAacttcaacatatgaattttgagtggacacaattcaacccatagcaCCTC 121 CGTGTAAGAGCTGGGAAGGGAAAGTGGCTAAGTTGTGCAAATGTGCACATTGGTTGGAGA
             <<<<<<<<<<<<<<<<<<<<
 181 TGATTAACTTCTGGCATGT
```

35) Whole sequence ::: rs11088023-rs11088024 agggggaaattggcaatctgattctaaaattcataCggaaaaaaacaatggagttagaat aactaaaacaagtccgaaaaagaaaaagaaatggaggactaatgctacctgatttcaagt cttatcTtataaatctacatcaataaaggacaagttg (SEQ ID NO: 106)

```
OLIGO          start   len   tm      gc %    any    3'     seq (SEQ ID NOs: 107, 108)
LEFT PRIMER      6      20   54.34   35.00   7.00   3.00   gaaattggcaatctgattct
RIGHT PRIMER   157      21   51.94   33.33   5.00   0.00   caacttgtcctttattgatgt
```

SEQUENCE SIZE: 157
INCLUDED REGION SIZE: 157

TABLE 2-continued

PRODUCT SIZE: 152, PAIR ANY COMPL: 4.00, PAIR 3' COMPL: 0.00

```
  1 aggggggaaattggcaatctgattctaaaattcataCggaaaaaaacaatggagttagaat
      >>>>>>>>>>>>>>>>>>>>

61 aactaaaacaagtccgaaaaagaaaaagaaatggaggactaatgctacctgatttcaagt 121 cttatcTtataaatctacatcaataaaggacaagttg
              <<<<<<<<<<<<<<<<<<<<
```

36) Whole sequence ::: rs1011734-rs1011733

TCTGTGTTTGTCTATGTTGATAAAACATTGAAATGCCAaATAGCTCAAAGGTCATTCACT

TAAGAAATCTAAGTACTGATAACATCTTAGCCCCGATTCTTCATAGGCATTGTTAAGCCT

ATTATAATTTTGGTtCAGAGAGAAGGTAAACTATATTCCAGACAGGCATATAA (SEQ ID NO: 109)

| OLIGO | start | len | tm | gc % | any | 3' | seq (SEQ ID NOs: 110, 111) |
|---|---|---|---|---|---|---|---|
| LEFT PRIMER | 12 | 22 | 50.06 | 22.73 | 6.00 | 2.00 | CTATGTTGATAAAACATTGAAA |
| RIGHT PRIMER | 167 | 20 | 51.09 | 40.00 | 4.00 | 2.00 | GCCTGTCTGGAATATAGTTT |

SEQUENCE SIZE: 173
INCLUDED REGION SIZE: 173

PRODUCT SIZE: 156, PAIR ANY COMPL: 5.00, PAIR 3' COMPL: 3.00

```
  1 TCTGTGTTTGTCTATGTTGATAAAACATTGAAATGCCAaATAGCTCAAAGGTCATTCACT
       >>>>>>>>>>>>>>>>>>>>>>

61 TAAGAAATCTAAGTACTGATAACATCTTAGCCCCGATTCTTCATAGGCATTGTTAAGCCT

121 ATTATAATTTTGGTtCAGAGAGAAGGTAAACTATATTCCAGACAGGCATATAA
                             <<<<<<<<<<<<<<<<<<<<
```

37) Whole sequence ::: rs2831244-rs9789838

TGCAGGGCATATAATCTAAGCTGTAAACGTCCTGTcAGAAGACAACATATTCATCTTGCT

AAGGTtTAAGCTATATGACTGGCACTGTGCTCAACTCAGAGTCATTGAATGAACAGTATT

TATTTA (SEQ ID NO: 112)

| OLIGO | start | len | tm | gc % | any | 3' | seq (SEQ ID NOs: 113, 114) |
|---|---|---|---|---|---|---|---|
| LEFT PRIMER | 3 | 22 | 55.40 | 40.91 | 5.00 | 3.00 | CAGGGCATATAATCTAAGCTGT |
| RIGHT PRIMER | 107 | 21 | 55.99 | 47.62 | 7.00 | 2.00 | CAATGACTCTGAGTTGAGCAC |

SEQUENCE SIZE: 126
INCLUDED REGION SIZE: 126

PRODUCT SIZE: 105, PAIR ANY COMPL: 4.00, PAIR 3' COMPL: 2.00

```
  1 TGCAGGGCATATAATCTAAGCTGTAAACGTCCTGTcAGAAGACAACATATTCATCTTGCT
      >>>>>>>>>>>>>>>>>>>>>>

61 AAGGTtTAAGCTATATGACTGGCACTGTGCTCAACTCAGAGTCATTGAATGAACAGTATT
                              <<<<<<<<<<<<<<<<<<<<<

121 TATTTA
```

38) Whole sequence ::: rs8132769-rs2831440

TTCACATTATTCCCTTAAAATAAACTCTCTCCCTCCCCTCTCCCGTCTCAaCCTTGTCCC

TTTCTTTATATAATGGGTAATtCGTTAATGTCAGCAGAATAGTTTTGGGGCCATAATGGC

AAGTATCACGTG (SEQ ID NO: 115)

| OLIGO | start | len | tm | gc % | any | 3' | seq (SEQ ID NOs: 116, 117) |
|---|---|---|---|---|---|---|---|
| LEFT PRIMER | 23 | 19 | 56.84 | 57.89 | 1.00 | 0.00 | AACTCTCTCCCTCCCCTCT |
| RIGHT PRIMER | 115 | 20 | 56.24 | 40.00 | 4.00 | 2.00 | TATGGCCCCAAAACTATTCT |

SEQUENCE SIZE: 132
INCLUDED REGION SIZE: 132

PRODUCT SIZE: 93, PAIR ANY COMPL: 2.00, PAIR 3' COMPL: 0.00

TABLE 2-continued

```
  1 TTCACATTATTCCCTTAAAATAAACTCTCTCCCTCCCCTCTCCCGTCTCAaCCTTGTCCC
                               >>>>>>>>>>>>>>>>>>>>

61 TTTCTTTATATAATGGGTAATtCGTTAATGTCAGCAGAATAGTTTTGGGGCCATAATGGC
                                     <<<<<<<<<<<<<<<<<<<<

121 AAGTATCACGTG
```

39) Whole sequence ::: rs8134080-rs2831524

TCAGGAAGCAACAAGTACTGGGCAGATTGATACTGTAGCTaGGCTCTAGCTCTATACCTC

TAGAATaaatgttacaaactagcaacttgaaagctaaacctggcccacag (SEQ ID NO: 118)

| OLIGO | start | len | tm | gc % | any | 3' | seq (SEQ ID NOs: 119, 120) |
|---|---|---|---|---|---|---|---|
| LEFT PRIMER | 11 | 20 | 55.75 | 45.00 | 6.00 | 2.00 | ACAAGTACTGGGCAGATTGA |
| RIGHT PRIMER | 104 | 20 | 56.27 | 45.00 | 4.00 | 2.00 | gccaggtttagctttcaagt |

SEQUENCE SIZE: 110
INCLUDED REGION SIZE: 110

PRODUCT SIZE: 94, PAIR ANY COMPL: 4.00, PAIR 3' COMPL: 3.00

```
  1 TCAGGAAGCAACAAGTACTGGGCAGATTGATACTGTAGCTaGGCTCTAGCTCTATACCTC
                 >>>>>>>>>>>>>>>>>>>>

61 TAGAATaaatgttacaaactagcaacttgaaagctaaacctggcccacag
                                <<<<<<<<<<<<<<<<<<<<
```

40) Whole sequence ::: rs4817219-rs4817220 tggttcttgagaattttatatcaggagaaacactgtcagtCtgtattgaaaggaacagag aaaatTcgaaattaaagaagactattaaacctccaaaattctggca (SEQ ID NO: 121)

| OLIGO | start | len | tm | gc % | any | 3' | seq (SEQ ID NOs: 122, 123) |
|---|---|---|---|---|---|---|---|
| LEFT PRIMER | 14 | 22 | 51.54 | 31.82 | 4.00 | 3.00 | ttttatatcaggagaaacactg |
| RIGHT PRIMER | 104 | 21 | 55.03 | 33.33 | 8.00 | 2.00 | ccagaatttttggaggtttaat |

SEQUENCE SIZE: 106
INCLUDED REGION SIZE: 106

PRODUCT SIZE: 91, PAIR ANY COMPL: 4.00, PAIR 3' COMPL: 2.00

```
  1 tggttcttgagaattttatatcaggagaaacactgtcagtCtgtattgaaaggaacagag
                    >>>>>>>>>>>>>>>>>>>>>>

61 aaaatTcgaaattaaagaagactattaaacctccaaaattctggca
                                <<<<<<<<<<<<<<<<<<<<<
```

41) Whole sequence ::: rs2250911-rs2250997

GCATCAAACTACACACTGTCATTCCTCCTTTATCTCCAAAAGCTTGAAAATTCCTCACTT

GTaTCTCATTCTTTCTCTCTTAGAAAACTGATCACCTCTGATGAATTAgAACGGAATGAC

CAAGCTTTGGGAGAGGCAAAAGAATCTCGGTGTTAAAGACTCAGAGTTTAA (SEQ ID NO: 124)

| OLIGO | start | len | tm | gc % | any | 3' | seq (SEQ ID NOs: 125, 126) |
|---|---|---|---|---|---|---|---|
| LEFT PRIMER | 17 | 22 | 58.65 | 40.91 | 3.00 | 0.00 | TGTCATTCCTCCTTTATCTCCA |
| RIGHT PRIMER | 144 | 20 | 59.42 | 45.00 | 4.00 | 2.00 | TTCTTTTGCCTCTCCCAAAG |

SEQUENCE SIZE: 171
INCLUDED REGION SIZE: 171

PRODUCT SIZE: 128, PAIR ANY COMPL: 4.00, PAIR 3' COMPL: 0.00

```
  1 GCATCAAACTACACACTGTCATTCCTCCTTTATCTCCAAAAGCTTGAAAATTCCTCACTT
                    >>>>>>>>>>>>>>>>>>>>>>

61 GTaTCTCATTCTTTCTCTCTTAGAAAACTGATCACCTCTGATGAATTAgAACGGAATGAC

121 CAAGCTTTGGGAGAGGCAAAAGAATCTCGGTGTTAAAGACTCAGAGTTTAA
           <<<<<<<<<<<<<<<<<<<<
```

TABLE 2-continued

42) Whole sequence ::: rs2831899-rs2831900

TTGAAAATTAAGAAACCCTGGCACAGTGTTGACTGGAGCCaCTTACCTTAATAGAAAATA

AAGCTCACATATATCCATAATGAAAAGCAGAGACCAGCACAACCATAGTCACCTGACAGT

TTtAAAATCCAAGGCCAGGATCTTCTCAACTCAGGCCCACTCA (SEQ ID NO: 127)

```
OLIGO           start   len   tm      gc %    any    3'     seq (SEQ ID NOs: 128, 129)
LEFT PRIMER     15      20    60.63   55.00   6.00   2.00   ACCCTGGCACAGTGTTGACT
RIGHT PRIMER    159     20    59.80   50.00   4.00   2.00   TGGGCCTGAGTTGAGAAGAT
```

SEQUENCE SIZE: 163
INCLUDED REGION SIZE: 163

PRODUCT SIZE: 145, PAIR ANY COMPL: 5.00, PAIR 3' COMPL: 1.00

```
   1 TTGAAAATTAAGAAACCCTGGCACAGTGTTGACTGGAGCCaCTTACCTTAATAGAAAATA
                    >>>>>>>>>>>>>>>>>>>>

61 AAGCTCACATATATCCATAATGAAAAGCAGAGACCAGCACAACCATAGTCACCTGACAGT

121 TTtAAAATCCAAGGCCAGGATCTTCTCAACTCAGGCCCACTCA
                         <<<<<<<<<<<<<<<<<<<<
```

43) Whole sequence ::: rs2831902-rs2831903

CACATAACTAATAAATTTGTAAGTATGTGCAACGGCTCACaCTTGCTTCCAGAATGGCAC

CTAAAAAACAGATTTACCTCTCCCCAAATTCAGATATGGAATTAAATGTAATGTCAGGAA

AAcTGTCTAAGAGTTGGAAATGGGAAAAAAATGTTCTTTTGGT (SEQ ID NO: 212)

```
OLIGO           start   len   tm      gc %    any    3'     seq (SEQ ID NOs: 213, 130)
LEFT PRIMER     14      21    53.16   33.33   4.00   2.00   AATTTGTAAGTATGTGCAACG
RIGHT PRIMER    149     20    56.27   35.00   2.00   0.00   TTTTTCCCATTTCCAACTCT
```

SEQUENCE SIZE: 163
INCLUDED REGION SIZE: 163

PRODUCT SIZE: 136, PAIR ANY COMPL: 4.00, PAIR 3' COMPL: 2.00

```
   1 CACATAACTAATAAATTTGTAAGTATGTGCAACGGCTCACaCTTGCTTCCAGAATGGCAC
                   >>>>>>>>>>>>>>>>>>>>>

61 CTAAAAAACAGATTTACCTCTCCCCAAATTCAGATATGGAATTAAATGTAATGTCAGGAA

121 AAcTGTCTAAGAGTTGGAAATGGGAAAAAAATGTTCTTTTGGT
                        <<<<<<<<<<<<<<<<<<<<
```

44) Whole sequence ::: rs11088086-rs2251447

AAAAAAAAAGATGAGACAGGCAGGTGCGAAAGAAATAAAAGTCAaAACTGATCCAGTTGG

GAAACTCAGAATTGACAGTTAcGTGTCCTTTCATTTATTGATATTTTGAGATTCACAGGG

GT (SEQ ID NO: 131)

```
OLIGO           start   len   tm      gc %    any    3'     seq (SEQ ID NOs: 132, 133)
LEFT PRIMER     6       20    56.41   45.00   2.00   2.00   AAAAGATGAGACAGGCAGGT
RIGHT PRIMER    122     20    55.99   40.00   5.00   2.00   ACCCCTGTGAATCTCAAAAT
```

SEQUENCE SIZE: 122
INCLUDED REGION SIZE: 122

PRODUCT SIZE: 117, PAIR ANY COMPL: 5.00, PAIR 3' COMPL: 2.00

```
   1 AAAAAAAAAGATGAGACAGGCAGGTGCGAAAGAAATAAAAGTCAaAACTGATCCAGTTGG
             >>>>>>>>>>>>>>>>>>>>

61 GAAACTCAGAATTGACAGTTAcGTGTCCTTTCATTTATTGATATTTTGAGATTCACAGGG
                                             <<<<<<<<<<<<<<<<<<<<

121 GT
     <<
```

TABLE 2-continued

45) Whole sequence ::: rs2832040-rs11088088

GAGTTAAATAAAGCACTTGCTTCTATTGTTTGTACCTAAACTTAACAGAAcACAGTAAGT

AACAAGTCATTGGGATGCAGAAAAGAAAAAAGAGAGTGAAGGAAGGAGAaAAGGTGAAGG

GAGAATGGAAGAGAGGAAGGGAGGGAGGAA (SEQ ID NO: 134)

```
OLIGO          start   len   tm      gc %    any    3'     seq (SEQ ID NOs: 135, 136)
LEFT PRIMER    13      21    54.81   38.10   4.00   0.00   GCACTTGCTTCTATTGTTTGT
RIGHT PRIMER   141     20    57.37   50.00   2.00   0.00   CCCTTCCTCTCTTCCATTCT
```

SEQUENCE SIZE: 150
INCLUDED REGION SIZE: 150

PRODUCT SIZE: 129, PAIR ANY COMPL: 2.00, PAIR 3' COMPL: 0.00

```
  1 GAGTTAAATAAAGCACTTGCTTCTATTGTTTGTACCTAAACTTAACAGAAcACAGTAAGT
                >>>>>>>>>>>>>>>>>>>>>

61 AACAAGTCATTGGGATGCAGAAAAGAAAAAAGAGAGTGAAGGAAGGAGAaAAGGTGAAGG

121 GAGAATGGAAGAGAGGAAGGGAGGGAGGAA
       <<<<<<<<<<<<<<<<<<<<
```

46) Whole sequence ::: rs2832141-rs2246777 aaacgagccaccagtgggAGCACTGCAGGTATCTGTGTGAGACCcGTACTTCACAACTCC

TGCTTTCCCTCCATAAAGtAGCTTGCATTTTCCACATTGACTTTGCAGTTCTTTGGTATC

TGTATTGGT (SEQ ID NO: 137)

```
OLIGO          start   len   tm      gc %    any    3'     seq (SEQ ID NOs: 138, 139)
LEFT PRIMER    14      18    58.28   61.11   6.00   2.00   gtgggAGCACTGCAGGTA
RIGHT PRIMER   123     21    55.05   38.10   4.00   2.00   ACAGATACCAAAGAACTGCAA
```

SEQUENCE SIZE: 129
INCLUDED REGION SIZE: 129

PRODUCT SIZE: 110, PAIR ANY COMPL: 5.00, PAIR 3' COMPL: 3.00

```
  1 aaacgagccaccagtgggAGCACTGCAGGTATCTGTGTGAGACCcGTACTTCACAACTCC
                   >>>>>>>>>>>>>>>>>>

61 TGCTTTCCCTCCATAAAGtAGCTTGCATTTTCCACATTGACTTTGCAGTTCTTTGGTATC
                                           <<<<<<<<<<<<<<<<<<<<<

121 TGTATTGGT
       <<<
```

47) Whole sequence ::: rs2832959-rs9980934

TGGACACCTTTCAACTTAGAAATCATAAACAGATTCATTTcCTTAAAGTTAATGaaaaga attaacagaccctcctcaaaaaagacatatatgcagcctacaatcatatgaaaaaaagtt caacattactgttcagcaaatcaaa (SEQ ID NO: 140)

```
OLIGO          start   len   tm      gc %    any    3'     seq (SEQ ID NOs: 141, 142)
LEFT PRIMER    1       20    53.30   40.00   3.00   3.00   TGGACACCTTTCAACTTAGA
RIGHT PRIMER   134     22    50.67   27.27   8.00   3.00   gaacagtaatgttgaacttttt
```

SEQUENCE SIZE: 145
INCLUDED REGION SIZE: 145

PRODUCT SIZE: 134, PAIR ANY COMPL: 7.00, PAIR 3' COMPL: 3.00

```
  1 TGGACACCTTTCAACTTAGAAATCATAAACAGATTCATTTcCTTAAAGTTAATGaaaaga
    >>>>>>>>>>>>>>>>>>>>

61 attaacagaccctcctcaaaaaagacatatatgcagcctacaatcatatgaaaaaaagtt
                                                      <<<<<<<
```

TABLE 2-continued

```
121caacattactgttcagcaaatcaaa
   <<<<<<<<<<<<

7th group
48) Whole sequence ::: rs2833734-rs2833735
```

TGGATACATTCCTAGAAATAGATGGAAACTGCTCTTGCAAAAAGCTTAGCACATGTTAAA aATTTTAGAAACAATTTGCCAAAGTTTATTTAGTCTAGTGATTTtGACAGGTTAAATGGA

CCCTTTGAGATCTTTTTTCCTCAAGTACAAAGGCT (SEQ ID NO: 143)

```
OLIGO          start   len    tm     gc %   any    3'     seq (SEQ ID NOs: 144, 145)
LEFT PRIMER     33      21   58.90   38.10  6.00  2.00   TCTTGCAAAAAGCTTAGCACA
RIGHT PRIMER   137      21   57.77   38.10  6.00  1.00   AAAAAGATCTCAAAGGGTCCA

SEQUENCE SIZE: 155
INCLUDED REGION SIZE: 155

PRODUCT SIZE: 105, PAIR ANY COMPL: 4.00, PAIR 3' COMPL: 0.00

1TGGATACATTCCTAGAAATAGATGGAAACTGCTCTTGCAAAAAGCTTAGCACATGTTAAA
                                   >>>>>>>>>>>>>>>>>>>>>

61aATTTTAGAAACAATTTGCCAAAGTTTATTTAGTCTAGTGATTTtGACAGGTTAAATGGA
                                                           <<<<

121CCCTTTGAGATCTTTTTTCCTCAAGTACAAAGGCT
    <<<<<<<<<<<<<<<<<

49) Whole sequence ::: rs933121-rs933122
```

GCTTTTGCTGAACATCAAGTGGTGAGCCAGGACTCAAaGCCAGATCTTCTTGTTTCCCTG

TTAGGTGTtTGTAGCACAACTGGTATCTGCAGACTATGCTGCTGGAAGGGCTAGCCGTC (SEQ ID NO: 146)

```
OLIGO          start   len    tm     gc %   any    3'     seq (SEQ ID NOs: 147, 148)
LEFT PRIMER     1       20   55.61   40.00  6.00  3.00   GCTTTTGCTGAACATCAAGT
RIGHT PRIMER   109      19   55.56   52.63  3.00  3.00   CCTTCCAGCAGCATAGTCT

SEQUENCE SIZE: 119
INCLUDED REGION SIZE: 119

PRODUCT SIZE: 109, PAIR ANY COMPL: 5.00, PAIR 3' COMPL: 1.00

1GCTTTTGCTGAACATCAAGTGGTGAGCCAGGACTCAAaGCCAGATCTTCTTGTTTCCCTG
    >>>>>>>>>>>>>>>>>>>>

61TTAGGTGTtTGTAGCACAACTGGTATCTGCAGACTATGCTGCTGGAAGGGCTAGCCGTC
                                                <<<<<<<<<<<<<<<<<<<

50) Whole sequence ::: rs2834140-rs12626953
```

ACTGTCCTAGAAAATCCAGGATGTGCAGTGATCAtGTATGAATGCATGGACCTGCACACA

CAGGAGTGAACAAAAGACCCACCCCTGCCAGGTCACCACTCATATCTCACCCCAGCCCAC

GCTAGCTCACaCTCCTCCCCACACACCACTGACCTCATCAT (SEQ ID NO: 149)

```
OLIGO          start   len    tm     gc %   any    3'     seq (SEQ ID NOs: 150, 151)
LEFT PRIMER     12      18   53.64   44.44  7.00  1.00   AAATCCAGGATGTGCAGT
RIGHT PRIMER   161      19   53.29   47.37  4.00  0.00   ATGATGAGGTCAGTGGTGT

SEQUENCE SIZE: 161
INCLUDED REGION SIZE: 161

PRODUCT SIZE: 150, PAIR ANY COMPL: 3.00, PAIR 3' COMPL: 0.00

1ACTGTCCTAGAAAATCCAGGATGTGCAGTGATCAtGTATGAATGCATGGACCTGCACACA
               >>>>>>>>>>>>>>>>>>

61CAGGAGTGAACAAAAGACCCACCCCTGCCAGGTCACCACTCATATCTCACCCCAGCCCAC

121GCTAGCTCACaCTCCTCCCCACACACCACTGACCTCATCAT
                       <<<<<<<<<<<<<<<<<<<
```

TABLE 2-continued

51) Whole sequence ::: rs2834485-rs3453

CACATCACAGATCATAGTAAATGGCTTTAATTTTTTAaCGAAATCTCACTACTGCAAATG

CATTGTTGTCCTAGCTAATGAATGCAtAGAGTATTGCCTGCAAAATAATAATTGAGATTC

TATT (SEQ ID NO: 152)

| OLIGO | start | len | tm | gc % | any | 3' | seq (SEQ ID NOs: 153, 154) |
|---|---|---|---|---|---|---|---|
| LEFT PRIMER | 3 | 22 | 52.35 | 36.36 | 4.00 | 0.00 | CATCACAGATCATAGTAAATGG |
| RIGHT PRIMER | 113 | 21 | 53.50 | 23.81 | 6.00 | 4.00 | AATTATTATTTTGCAGGCAAT |

SEQUENCE SIZE: 124
INCLUDED REGION SIZE: 124

PRODUCT SIZE: 111, PAIR ANY COMPL: 5.00, PAIR 3' COMPL: 2.00

```
  1 CACATCACAGATCATAGTAAATGGCTTTAATTTTTTAaCGAAATCTCACTACTGCAAATG
    >>>>>>>>>>>>>>>>>>>>>>

61 CATTGTTGTCCTAGCTAATGAATGCAtAGAGTATTGCCTGCAAAATAATAATTGAGATTC
                                            <<<<<<<<<<<<<<<<<<<<<

121 TATT
```

8th group
52) Whole sequence ::: rs9974986-rs2834703

TTATCCTCCACATCCTCATGAGGCAAACACCTTTCCTACCTTACCGCTCCcCAGTGGCCT

CCCTGTTGCCTTCTTATTCAAGACTAAGACtCTCTAGAATGTTCTTTATCCTGAGTCCAG

CTGATTGTCTATACTAATATCAGTACGGGGT (SEQ ID NO: 155)

| OLIGO | start | len | tm | gc % | any | 3' | seq (SEQ ID NOs: 156, 157) |
|---|---|---|---|---|---|---|---|
| LEFT PRIMER | 17 | 20 | 60.50 | 50.00 | 4.00 | 2.00 | CATGAGGCAAACACCTTTCC |
| RIGHT PRIMER | 121 | 22 | 58.46 | 45.45 | 3.00 | 0.00 | GCTGGACTCAGGATAAAGAACA |

SEQUENCE SIZE: 151
INCLUDED REGION SIZE: 151

PRODUCT SIZE: 105, PAIR ANY COMPL: 4.00, PAIR 3' COMPL: 1.00

```
  1 TTATCCTCCACATCCTCATGAGGCAAACACCTTTCCTACCTTACCGCTCCcCAGTGGCCT
                    >>>>>>>>>>>>>>>>>>>>

61 CCCTGTTGCCTTCTTATTCAAGACTAAGACtCTCTAGAATGTTCTTTATCCTGAGTCCAG
                                           <<<<<<<<<<<<<<<<<<<<<<

121 CTGATTGTCTATACTAATATCAGTACGGGGT
    <
```

53) Whole sequence ::: rs12482353-rs2205032

ATCACCTGGTTTGGTGCATCCTCGCAGAAAGAGAGCCATACAGTGAAGTGGAAACACACCCAAAAGCTCTGCAATATTCCT

AGAAGTTCTCGAATCTCCTCCTTAAcAGAGCTGCAGAAGGGAAACACAGACAGGAAGCACCTGTTTGACTCAgACAGCAGC

CCTAATGCAGTGCCACTCAGGAGCATTCCCTCATTTGAAGACCCCCCAATTACATGAAATTATCAACCCC (SEQ ID NO: 346)

| OLIGO | start | len | tm | gc % | any | 3' | seq (SEQ ID NOs: 347, 348) |
|---|---|---|---|---|---|---|---|
| LEFT PRIMER | 56 | 20 | 59.74 | 45.00 | 4.00 | 2.00 | ACACCCAAAAGCTCTGCAAT |
| RIGHT PRIMER | 199 | 20 | 60.59 | 50.00 | 4.00 | 2.00 | CAAATGAGGGAATGCTCCTG |

SEQUENCE SIZE: 232
INCLUDED REGION SIZE: 232

PRODUCT SIZE: 144, PAIR ANY COMPL: 3.00, PAIR 3' COMPL: 0.00

```
  1 ATCACCTGGTTTGGTGCATCCTCGCAGAAAGAGAGCCATACAGTGAAGTGGAAACACACC
                                                         >>>>>

61 CAAAAGCTCTGCAATATTCCTAGAAGTTCTCGAATCTCCTCCTTAAcAGAGCTGCAGAAG
    >>>>>>>>>>>>>>>

121 GGAAACACAGACAGGAAGCACCTGTTTGACTCAgACAGCAGCCCTAATGCAGTGCCACTC
                                                               <
```

TABLE 2-continued

```
181AGGAGCATTCCCTCATTTGAAGACCCCCCAATTACATGAAATTATCAACCCC
      <<<<<<<<<<<<<<<<<<<<
```

54) Whole sequence ::: rs2776266-rs2835001

```
agggtgcagcactttattatggaagcctgagctgactaatacaGGTGTCTcTATATCTCA

CTGAGGGAAAGTGACAGGAAAGTAAGAACCATTTaTGTCCAAGAGTCCAGAGGAGTCAAC

CAGATTCTGGGGGAAAAGAAGGTAC (SEQ ID NO: 158)

OLIGO          start    len   tm     gc %   any   3'    seq (SEQ ID NOs: 159, 160)

LEFT PRIMER     20       20    58.75  50.00  4.00  1.00  tggaagcctgagctgactaa
RIGHT PRIMER   142       20    59.87  50.00  4.00  3.00  CCTTCTTTTCCCCCAGAATC
SEQUENCE SIZE: 145
INCLUDED REGION SIZE: 145

PRODUCT SIZE: 123, PAIR ANY COMPL: 4.00, PAIR 3' COMPL: 0.00

1agggtgcagcactttattatggaagcctgagctgactaatacaGGTGTCTcTATATCTCA
                        >>>>>>>>>>>>>>>>>>>>

61CTGAGGGAAAGTGACAGGAAAGTAAGAACCATTTaTGTCCAAGAGTCCAGAGGAGTCAAC

121CAGATTCTGGGGGAAAAGAAGGTAC
        <<<<<<<<<<<<<<<<<<<<
```

55) Whole sequence ::: rs1984014-rs1984015

```
TGAGAAT TTAGGAGAACAGAAGATCAGAGGGCTGCACaGGCTAAACTAGACAATGAGCCC

ATGCAAGTAAGTTAAGAGGAGAAGCGGGTAAGTATGCACCTGCTTTGTCTAGGtGACCAG

CAAGCATTTAGCAATAGTCTTT TCAAAACAACAG (SEQ ID NO: 161)

OLIGO          start    len   tm     gc %   any   3'    seq (SEQ ID NOs: 162, 163)

LEFT PRIMER      8       22    53.09  40.91  4.00  1.00  TTAGGAGAACAGAAGATCAGAG
RIGHT PRIMER   142       22    53.52  31.82  4.00  2.00  AAAGACTATTGCTAAATGCTTG
SEQUENCE SIZE: 154
INCLUDED REGION SIZE: 154

PRODUCT SIZE: 135, PAIR ANY COMPL: 4.00, PAIR 3' COMPL: 2.00

1TGAGAATTTAGGAGAACAGAAGATCAGAGGGCTGCACaGGCTAAACTAGACAATGAGCCC
            >>>>>>>>>>>>>>>>>>>>>>

61ATGCAAGTAAGTTAAGAGGAGAAGCGGGTAAGTATGCACCTGCTTTGTCTAGGtGACCAG

121CAAGCATTTAGCAATAGTCTTTTCAAAACAACAG
        <<<<<<<<<<<<<<<<<<<<<<
```

56) Whole sequence ::: rs1014593-rs9305569

```
GGAACTGCAGGAGATCCCTGCTGCCTTCCAGTTCATGGGATGATGGCCTCCACTTCTGCCCCTGTTTGCTTCTCCTTTCAa

ATCTTACATGAAGGTATACAGTTTGAAGAAGCCAGTTTGACTCCAATATCTGTGCAATGGAATACTGCTCATTAAAAAGgA

ATTAAACTATTGATACACACAACATGGGTGAAGATCAAACTGTCTCCTTCCCTTTGATTCAAGGGAATCTGAGAAATG (SEQ ID NO: 349)

OLIGO          start    len   tm     gc %   any   3'    seq (SEQ ID NOs: 350, 351)

LEFT PRIMER     51       19    59.86  52.63  2.00  0.00  ACTTCTGCCCCTGTTTGCT
RIGHT PRIMER   198       21    58.84  42.86  4.00  3.00  TGATCTTCACCCATGTTGTGT
SEQUENCE SIZE: 239
INCLUDED REGION SIZE: 239

PRODUCT SIZE: 148, PAIR ANY COMPL: 2.00, PAIR 3' COMPL: 0.00

1GAACTGCAGGAGATCCCTGCTGCCTTCCAGTTCATGGGATGATGGCCTCCACTTCTGCCC
                                                      >>>>>>>>>

61CTGTTTGCTTCTCCTTTCAaATCTTACATGAAGGTATACAGTTTGAAGAAGCCAGTTTGA
     >>>>>>>>>>
```

```
121 CTCCAATATCTGTGCAATGGAATACTGCTCATTAAAAAGgAATTAAACTATTGATACACA
                                                             <<<

181 CAACATGGGTGAAGATCAAACTGTCTCCTTCCCTTTGATTCAAGGGAATCTGAGAAATG
    <<<<<<<<<<<<<<<
```

57) Whole sequence ::: rs7281674-rs2835316

AAACAGGCAAAATAAGCGTAGGGCTGTGTGTGCAACAGTTaATCATAAAGCCATCACCAG

GAGACgTCACTGGGCGCCTTCTGGAGTCTATCCGTCCTAACTTTGC (SEQ ID NO: 164)

| OLIGO | start | len | tm | gc % | any | 3' | seq (SEQ ID NOs: 165, 166) |
|---|---|---|---|---|---|---|---|
| LEFT PRIMER | 13 | 20 | 59.93 | 55.00 | 4.00 | 0.00 | TAAGCGTAGGGCTGTGTGTG |
| RIGHT PRIMER | 97 | 21 | 60.08 | 57.14 | 3.00 | 1.00 | GGACGGATAGACTCCAGAAGG |

SEQUENCE SIZE: 106
INCLUDED REGION SIZE: 106

PRODUCT SIZE: 85, PAIR ANY COMPL: 3.00, PAIR 3' COMPL: 0.00

```
  1 AAACAGGCAAAATAAGCGTAGGGCTGTGTGTGCAACAGTTaATCATAAAGCCATCACCAG
                >>>>>>>>>>>>>>>>>>>>

61 GAGACgTCACTGGGCGCCTTCTGGAGTCTATCCGTCCTAACTTTGC
                    <<<<<<<<<<<<<<<<<<<<<
```

58) Whole sequence ::: rs13047304-rs13047322 gaatgaccttggcacttttatcaaacatcaactggccacaCacaggtgagtctacttctg gacacttaTcctgttccattcatctgtatatctctatccttacac (SEQ ID NO: 167)

| OLIGO | start | len | tm | gc % | any | 3' | seq (SEQ ID NOs: 168, 169) |
|---|---|---|---|---|---|---|---|
| LEFT PRIMER | 1 | 23 | 60.36 | 39.13 | 3.00 | 2.00 | gaatgaccttggcacttttatca |
| RIGHT PRIMER | 101 | 27 | 57.86 | 33.33 | 4.00 | 0.00 | aaggatagagatatacagatgaatgga |

SEQUENCE SIZE: 105
INCLUDED REGION SIZE: 105

PRODUCT SIZE: 101, PAIR ANY COMPL: 4.00, PAIR 3' COMPL: 1.00

```
  1 gaatgaccttggcacttttatcaaacatcaactggccacaCacaggtgagtctacttctg
    >>>>>>>>>>>>>>>>>>>>>>>

61 gacacttaTcctgttccattcatctgtatatctctatccttacac
                    <<<<<<<<<<<<<<<<<<<<<<<<<<<
```

59) Whole sequence ::: rs2835545-rs4816551

CTGCTGGAATAGGCTGCTTGGCCATGTTCTTGGAAGCTACCACCATATCAaGGTAATTTC

CCACACAACATTCCAGCCCCTGCTTTCCtCTCTGGCCTTATCTAGGGCCATTCCCCAACT

CAGGTGAAT (SEQ ID NO: 170)

| OLIGO | start | len | tm | gc % | any | 3' | seq (SEQ ID NOs: 171, 172) |
|---|---|---|---|---|---|---|---|
| LEFT PRIMER | 20 | 20 | 60.21 | 50.00 | 4.00 | 2.00 | GGCCATGTTCTTGGAAGCTA |
| RIGHT PRIMER | 128 | 20 | 60.89 | 50.00 | 5.00 | 0.00 | TTCACCTGAGTTGGGGAATG |

SEQUENCE SIZE: 129
INCLUDED REGION SIZE: 129

PRODUCT SIZE: 109, PAIR ANY COMPL: 3.00, PAIR 3' COMPL: 0.00

```
  1 CTGCTGGAATAGGCTGCTTGGCCATGTTCTTGGAAGCTACCACCATATCAaGGTAATTTC
                       >>>>>>>>>>>>>>>>>>>>

61 CCACACAACATTCCAGCCCCTGCTTTCCtCTCTGGCCTTATCTAGGGCCATTCCCCAACT
                                                  <<<<<<<<<<<<

121 CAGGTGAAT
    <<<<<<<<
```

TABLE 2-continued

60) Whole sequence ::: rs2835735-rs2835736

ACCTTTGTTCCATGCACCGCGCAAATACCTGGGAACCCTTaTTGCCCAACTCAAGAGCCA

GAGTCCTCTGTCATCATTTTGCCTCTCTCCTAAGTGAgAGGACTGAGTGCAGACTTGGTG

TTTGTGGGTGAGGCATGT (SEQ ID NO: 173)

| OLIGO | start | len | tm | gc % | any | 3' | seq (SEQ ID NOs: 174, 175) |
|---|---|---|---|---|---|---|---|
| LEFT PRIMER | 11 | 18 | 62.22 | 55.56 | 5.00 | 0.00 | CATGCACCGCGCAAATAC |
| RIGHT PRIMER | 136 | 19 | 59.38 | 52.63 | 2.00 | 0.00 | ATGCCTCACCCACAAACAC |

SEQUENCE SIZE: 138
INCLUDED REGION SIZE: 138

PRODUCT SIZE: 126, PAIR ANY COMPL: 3.00, PAIR 3' COMPL: 0.00

```
  1 ACCTTTGTTCCATGCACCGCGCAAATACCTGGGAACCCTTaTTGCCCAACTCAAGAGCCA
              >>>>>>>>>>>>>>>>>>

61 GAGTCCTCTGTCATCATTTTGCCTCTCTCCTAAGTGAgAGGACTGAGTGCAGACTTGGTG
                                                          <<<

121 TTTGTGGGTGAGGCATGT
    <<<<<<<<<<<<<<<
```

61) Whole sequence ::: rs13047608-rs2835826

CTCCTGAGTCCAAGCCCTTCTCACTCACCTCTTTCTTGAACTAATTTCTTcCTGTTTTTT

TCCAGTCCTCCCTTCTGTTCATGTCTCTCCTCTGCACACTTCCATTTTgTGGTTCAGAAA

ATGTCACCGTCCCAG TCACACTTGCCTTATGGCTGTTGT (SEQ ID NO: 176)

| OLIGO | start | len | tm | gc % | any | 3' | seq (SEQ ID NOs: 177, 178) |
|---|---|---|---|---|---|---|---|
| LEFT PRIMER | 9 | 20 | 60.39 | 55.00 | 4.00 | 0.00 | TCCAAGCCCTTCTCACTCAC |
| RIGHT PRIMER | 135 | 20 | 59.97 | 50.00 | 3.00 | 1.00 | CTGGGACGGTGACATTTTCT |

SEQUENCE SIZE: 159
INCLUDED REGION SIZE: 159

PRODUCT SIZE: 127, PAIR ANY COMPL: 4.00, PAIR 3' COMPL: 0.00

```
  1 CTCCTGAGTCCAAGCCCTTCTCACTCACCTCTTTCTTGAACTAATTTCTTcCTGTTTTTT
              >>>>>>>>>>>>>>>>>>>>

61 TCCAGTCCTCCCTTCTGTTCATGTCTCTCCTCTGCACACTTCCATTTTgTGGTTCAGAAA
                                                         <<<<<

121 ATGTCACCGTCCCAGTCACACTTGCCTTATGGCTGTTGT
       <<<<<<<<<<<<<<<
```

62) Whole sequence ::: rs857998-rs17284497

TGGAGAAAGTTGTTGCAAACTGCCCAGAGACCCTGGGAGTCACTCCAGTTTTCTGAAACCCAGATATTTCAGtGCCTCAGG

AGAGACAAGTCCTGACCTTCTCTCCTCCAGCTCTCCCAGgAGATAGGCAAGCCCCTAACTCCCTAACTAAGCCCTTCAGAC

CTGAAATCCATTGAGTGGCTTCTTT (SEQ ID NO: 352)

| OLIGO | start | len | tm | gc % | any | 3' | seq (SEQ ID NOs: 353, 354) |
|---|---|---|---|---|---|---|---|
| LEFT PRIMER | 15 | 18 | 59.35 | 61.11 | 4.00 | 0.00 | GCAAACTGCCCAGAGACC |
| RIGHT PRIMER | 147 | 20 | 60.57 | 55.00 | 2.00 | 2.00 | TTAGGGAGTTAGGGGCTTGC |

SEQUENCE SIZE: 189
INCLUDED REGION SIZE: 189

PRODUCT SIZE: 133, PAIR ANY COMPL: 5.00, PAIR 3' COMPL: 2.00

```
  1 TGGAGAAAGTTGTTGCAAACTGCCCAGAGACCCTGGGAGTCACTCCAGTTTTCTGAAACC
                   >>>>>>>>>>>>>>>>>>

61 CAGATATTTCAGtGCCTCAGGAGAGACAAGTCCTGACCTTCTCTCCTCCAGCTCTCCCAG 121 gAGATAGGCAAGCCCCTAACTCCCTAACTAAGCCCTTCAGACCTGAAATCCATTGAGTGG
            <<<<<<<<<<<<<<<<<<<<
```

181 CTTCTTTAC

9<sup>th</sup> group
63) Whole sequence ::: rs2836550-rs2212596

CCCAGGAAGAGTGGAAAGATTAACCTTTGTGAGCCAAACCaGTGACACTTGATTACTTGA

CAGAACTAATCCTTCTGTCCTGATGACAGAAcTTCAACTACACAGGTACATGCAAGCTAA

TATCTGTTGTAA (SEQ ID NO: 179)

| OLIGO | start | len | tm | gc % | any | 3' | seq (SEQ ID NOs: 180, 181) |
|---|---|---|---|---|---|---|---|
| LEFT PRIMER | 1 | 21 | 59.56 | 47.62 | 3.00 | 2.00 | CCCAGGAAGAGTGGAAAGATT |
| RIGHT PRIMER | 120 | 21 | 56.03 | 42.86 | 6.00 | 1.00 | TTAGCTTGCATGTACCTGTGT |

SEQUENCE SIZE: 132
INCLUDED REGION SIZE: 132

PRODUCT SIZE: 120, PAIR ANY COMPL: 5.00, PAIR 3' COMPL: 3.00

```
  1 CCCAGGAAGAGTGGAAAGATTAACCTTTGTGAGCCAAACCaGTGACACTTGATTACTTGA
    >>>>>>>>>>>>>>>>>>>>>

61 CAGAACTAATCCTTCTGTCCTGATGACAGAAcTTCAACTACACAGGTACATGCAAGCTAA
                                               <<<<<<<<<<<<<<<<<<<<<

121 TATCTGTTGTAA
```

64) Whole sequence ::: rs2836660-rs2836661

GCCTGGCAAGCTAGATGGGGTGAATTTTCACCTGCCACAGcCGCAAGTCAAAGCCACCGG

CTTCTCTCTTCTCCCTCCCATTGCTCCTGACAGCCAGGGTTAATATTTTGCCTCATGTAA

ACAGGGAGGCAtCCACCCGAGAATCTCCCCTCAGCCCACATAAGC (SEQ ID NO: 182)

| OLIGO | start | len | tm | gc % | any | 3' | seq (SEQ ID NOs: 183, 184) |
|---|---|---|---|---|---|---|---|
| LEFT PRIMER | 9 | 20 | 55.41 | 40.00 | 4.00 | 2.00 | AGCTAGATGGGGTGAATTTT |
| RIGHT PRIMER | 158 | 18 | 61.14 | 61.11 | 3.00 | 3.00 | TGGGCTGAGGGGAGATTC |

SEQUENCE SIZE: 165
INCLUDED REGION SIZE: 165

PRODUCT SIZE: 150, PAIR ANY COMPL: 4.00, PAIR 3' COMPL: 3.00

```
  1 GCCTGGCAAGCTAGATGGGGTGAATTTTCACCTGCCACAGcCGCAAGTCAAAGCCACCGG
            >>>>>>>>>>>>>>>>>>>>

61 CTTCTCTCTTCTCCCTCCCATTGCTCCTGACAGCCAGGGTTAATATTTTGCCTCATGTAA

121 ACAGGGAGGCAtCCACCCGAGAATCTCCCCTCAGCCCACATAAGC
                                <<<<<<<<<<<<<<<<<<
```

65) Whole sequence ::: rs465612-rs8131220 atcaagctaattaatgttatctatcacttcAcatagttcaacctttttttgtggtgagag tactgaagatctactctcttagcaattttcaaatctaaaatacattattattaacacagt cactgtgccGtacgttagctctgaggaccttattcatttt (SEQ ID NO: 185)

| OLIGO | start | len | tm | gc % | any | 3' | seq (SEQ ID NOs: 186, 187) |
|---|---|---|---|---|---|---|---|
| LEFT PRIMER | 1 | 22 | 47.51 | 22.73 | 6.00 | 4.00 | atcaagctaattaatgttatct |
| RIGHT PRIMER | 158 | 20 | 50.92 | 40.00 | 5.00 | 5.00 | aatgaataaggtcctcagag |

SEQUENCE SIZE: 160
INCLUDED REGION SIZE: 160

PRODUCT SIZE: 158, PAIR ANY COMPL: 5.00, PAIR 3' COMPL: 2.00

```
  1 atcaagctaattaatgttatctatcacttcAcatagttcaacctttttttgtggtgagag
    >>>>>>>>>>>>>>>>>>>>>>

61 tactgaagatctactctcttagcaattttcaaatctaaaatacattattattaacacagt 121 cactgtgccGtacgttagctctgaggaccttattcatttt
                        <<<<<<<<<<<<<<<<<<<<
```

TABLE 2-continued 66) whole sequence ::: rs9980072-rs8130031

TTTAATCTGATCATTGCCCTATGAGGTAGGgAGTATTCTGATTCCCATTTTATAAATAAG

GAACCCGAGGCTTAGAGAGCATCaGTGACTTGTTCAAGGTCACCCACAGCTGTCAAGTGA

CAGA (SEQ ID NO: 188)

| OLIGO | start | len | tm | gc % | any | 3' | seq (SEQ ID NOs: 189, 190) |
|---|---|---|---|---|---|---|---|
| LEFT PRIMER | 1 | 21 | 55.02 | 33.33 | 6.00 | 2.00 | TTTAATCTGATCATTGCCCTA |
| RIGHT PRIMER | 111 | 18 | 57.61 | 55.56 | 5.00 | 1.00 | AGCTGTGGGTGACCTTGA |

SEQUENCE SIZE: 124
INCLUDED REGION SIZE: 124

PRODUCT SIZE: 111, PAIR ANY COMPL: 3.00, PAIR 3' COMPL: 1.00

```
  1 TTTAATCTGATCATTGCCCTATGAGGTAGGgAGTATTCTGATTCCCATTTTATAAATAAG
    >>>>>>>>>>>>>>>>>>>>>

61 GAACCCGAGGCTTAGAGAGCATCaGTGACTTGTTCAAGGTCACCCACAGCTGTCAAGTGA
                                                    <<<<<<<<<<<<<<

121 CAGA
```

10<sup>th</sup> group
67) Whole sequence ::: rs418359-rs2836926 tgtcccaccattgtgtattaggtttgtagagCgtagacaacttgccttttagtttgtag gtttctgtatcaagagaagatgtgtgtGggcctaacctagattacaggatcctggacttc aagtctga (SEQ ID NO: 191)

| OLIGO | start | len | tm | gc % | any | 3' | seq (SEQ ID NOs: 192, 193) |
|---|---|---|---|---|---|---|---|
| LEFT PRIMER | 1 | 20 | 54.64 | 40.00 | 6.00 | 3.00 | tgtcccaccattgtgtatta |
| RIGHT PRIMER | 128 | 20 | 54.70 | 45.00 | 9.00 | 3.00 | tcagacttgaagtccaggat |

SEQUENCE SIZE: 128
INCLUDED REGION SIZE: 128

PRODUCT SIZE: 128, PAIR ANY COMPL: 3.00, PAIR 3' COMPL: 1.00

```
  1 tgtcccaccattgtgtattaggtttgtagagCgtagacaacttgccttttagtttgtag
    >>>>>>>>>>>>>>>>>>>>

61 gtttctgtatcaagagaagatgtgtgtGggcctaacctagattacaggatcctggacttc
                                                        <<<<<<<<<<

121 aagtctga
         <<<<<<<
```

68) Whole sequence ::: rs11701943-rs4816634 tcatttgctaaggtcggatagctcctaattggcaaagtcaCgatgggatcccagggattc tgaggatgaagcctgtgtttaataactAttatgccaAGTGAGCATTTTCAAATATATGAG

AGAAATTA (SEQ ID NO: 194)

| OLIGO | start | len | tm | gc % | any | 3' | seq (SEQ ID NOs: 162, 163) |
|---|---|---|---|---|---|---|---|
| LEFT PRIMER | 2 | 19 | 53.86 | 42.11 | 4.00 | 2.00 | catttgctaaggtcggata |
| RIGHT PRIMER | 114 | 20 | 51.56 | 30.00 | 6.00 | 2.00 | TATTTGAAAATGCTCACTtg |

SEQUENCE SIZE: 128
INCLUDED REGION SIZE: 128

PRODUCT SIZE: 113, PAIR ANY COMPL: 6.00, PAIR 3' COMPL: 0.00

```
  1 tcatttgctaaggtcggatagctcctaattggcaaagtcaCgatgggatcccagggattc
     >>>>>>>>>>>>>>>>>>>

61 tgaggatgaagcctgtgtttaataactAttatgccaAGTGAGCATTTTCAAATATATGAG
                                        <<<<<<<<<<<<<<<<<<<<

121 AGAAATTA
```

TABLE 2-continued

69) Whole sequence ::: rs7278447-rs7278858

CATTGCTTCAGGGGTGTTAGTTTTGTGTTCaCAACTAGATTATAAACTCCTCTTGCATTC

CTGATGGCAGTGACTTGAAGGCAtttatttgaagaataatagacatacagaaaggggcac atgtcataaaggtacagctggacgacttttcacaaagtg (SEQ ID NO: 197)

| OLIGO | start | len | tm | gc % | any | 3' | seq (SEQ ID NOs: 198, 199) |
|---|---|---|---|---|---|---|---|
| LEFT PRIMER | 5 | 20 | 55.96 | 45.00 | 2.00 | 0.00 | GCTTCAGGGGTGTTAGTTTT |
| RIGHT PRIMER | 157 | 20 | 55.97 | 45.00 | 5.00 | 1.00 | ctttgtgaaaagtcgtccag |

SEQUENCE SIZE: 159
INCLUDED REGION SIZE: 159

PRODUCT SIZE: 153, PAIR ANY COMPL: 4.00, PAIR 3' COMPL: 0.00

```
  1 CATTGCTTCAGGGGTGTTAGTTTTGTGTTCaCAACTAGATTATAAACTCCTCTTGCATTC
       >>>>>>>>>>>>>>>>>>>>

61 CTGATGGCAGTGACTTGAAGGCAtttatttgaagaataatagacatacagaaaggggcac 121 atgtcataaaggtacagctggacgacttttcacaaagtg
                   <<<<<<<<<<<<<<<<<<<<
```

70) Whole sequence ::: rs385787-rs367001

GAGAGGATGGTGCCATCATGGAAAGCATGGGGCAGTCATGGAGATGACGGaGTAGCTCAT

GGAGAAgATAATGCCATCATGGAAGGCATAGTGCAGTCATGGAGATGATGGTGCAGC (SEQ ID NO: 200)

| OLIGO | start | len | tm | gc % | any | 3' | seq (SEQ ID NOs: 201, 202) |
|---|---|---|---|---|---|---|---|
| LEFT PRIMER | 13 | 18 | 58.34 | 50.00 | 7.00 | 3.00 | CCATCATGGAAAGCATGG |
| RIGHT PRIMER | 108 | 20 | 55.09 | 45.00 | 4.00 | 2.00 | TCATCTCCATGACTGCACTA |

SEQUENCE SIZE: 117
INCLUDED REGION SIZE: 117

PRODUCT SIZE: 96, PAIR ANY COMPL: 7.00, PAIR 3' COMPL: 3.00

```
  1 GAGAGGATGGTGCCATCATGGAAAGCATGGGGCAGTCATGGAGATGACGGaGTAGCTCAT
                >>>>>>>>>>>>>>>>>>

61 GGAGAAgATAATGCCATCATGGAAGGCATAGTGCAGTCATGGAGATGATGGTGCAGC
                          <<<<<<<<<<<<<<<<<<<<
```

71) Whole sequence ::: rs367001-rs386095

ATGGGGCAGTCATGGAGATGACGGAGTAGCTCATGGAGAAaATAATGCCATCATGGAAGG

CATAGTGCAGTCATGGAGATGATGGTGCAGCTCATGGAGAAGATGGTGCCATCATGGAAG

GCATGGTGCAATCATGGAGTAGACAGTGCAGCTGGGCCaagattctc (SEQ ID NO: 203)

| OLIGO | start | len | tm | gc % | any | 3' | seq (SEQ ID NOs: 204, 205) |
|---|---|---|---|---|---|---|---|
| LEFT PRIMER | 15 | 20 | 54.39 | 50.00 | 4.00 | 3.00 | GAGATGACGGAGTAGCTCAT |
| RIGHT PRIMER | 156 | 18 | 55.17 | 61.11 | 6.00 | 2.00 | CCCAGCTGCACTGTCTAC |

SEQUENCE SIZE: 167
INCLUDED REGION SIZE: 167

PRODUCT SIZE: 142, PAIR ANY COMPL: 6.00, PAIR 3' COMPL: 2.00

```
  1 ATGGGGCAGTCATGGAGATGACGGAGTAGCTCATGGAGAAaATAATGCCATCATGGAAGG
                  >>>>>>>>>>>>>>>>>>>>

61 CATAGTGCAGTCATGGAGATGATGGTGCAGCTCATGGAGAAGATGGTGCCATCATGGaAG

121 GCATGGTGCAATCATGGAGTAGACAGTGCAGCTGGGCCaagattctc
                        <<<<<<<<<<<<<<<<<<
```

72) Whole sequence ::: rs2837296-rs2837297

GATGTGCCTCTCTTGTTCCAATCACAGGACAGGGGTATAAcTAGGGGCACTGTCTATACT

GGCTGCACTCTGGCCAGTGCTGTCCCAgGTAGATTCATCAGGGTCTAGAGCTTCAGCTAA

TABLE 2-continued

CAGCATGA (SEQ ID NO: 206)

| OLIGO | start | len | tm | gc % | any | 3' | seq (SEQ ID NOs: 207, 208) |
|---|---|---|---|---|---|---|---|
| LEFT PRIMER | 11 | 20 | 56.00 | 45.00 | 4.00 | 1.00 | TCTTGTTCCAATCACAGGAC |
| RIGHT PRIMER | 126 | 20 | 54.59 | 45.00 | 6.00 | 3.00 | ATGCTGTTAGCTGAAGCTCT |

SEQUENCE SIZE: 128
INCLUDED REGION SIZE: 128

PRODUCT SIZE: 116, PAIR ANY COMPL: 4.00, PAIR 3' COMPL: 1.00

```
  1 GATGTGCCTCTCTTGTTCCAATCACAGGACAGGGGTATAAcTAGGGGCACTGTCTATACT
              >>>>>>>>>>>>>>>>>>>>

61 GGCTGCACTCTGGCCAGTGCTGTCCCAgGTAGATTCATCAGGGTCTAGAGCTTCAGCTAA
                                               <<<<<<<<<<<<

121 CAGCATGA
    <<<<<<
```

73) Whole sequence ::: rs4239808-rs2410205

AGGGCCATGGGATGATGCAGGTGGAGACTGGAGTGCTACAGCTGCAAGCAAATACATTTCTGTGCTGTGAAGCCAcCCATT

TGGTGGTACTACGTTAAAACAGCTCTAGGAAATTAAtACAGATGTTGCCTGTATTTTGTTTCTCATATTACTACTCATTG

TTTTAATGATGACTGTTTTATT (SEQ ID NO: 355)

| OLIGO | start | len | tm | gc % | any | 3' | seq (SEQ ID NOs: 356, 357) |
|---|---|---|---|---|---|---|---|
| LEFT PRIMER | 19 | 20 | 57.45 | 55.00 | 4.00 | 2.00 | AGGTGGAGACTGGAGTGCTA |
| RIGHT PRIMER | 145 | 22 | 56.58 | 31.82 | 2.00 | 0.00 | AGAAACAAAAATACAGGCAACA |

SEQUENCE SIZE: 184
INCLUDED REGION SIZE: 184

PRODUCT SIZE: 127, PAIR ANY COMPL: 3.00, PAIR 3' COMPL: 1.00

```
  1 AGGGCCATGGGATGATGCAGGTGGAGACTGGAGTGCTACAGCTGCAAGCAAATACATTTC
                      >>>>>>>>>>>>>>>>>>>>

61 TGTGCTGTGAAGCCAcCCATTTGGTGGTACTACGTTAAAACAGCTCTAGGAAATTAAtAC

121 AGATGTTGCCTGTATTTTGTTTCTCATATTACTACTCATTGTTTTAATGATGACTGTTT
        <<<<<<<<<<<<<<<<<<<<<<

181 TATT
```

74) Whole sequence ::: rs2837381-rs4816672

TTTTATTCATTAAGTTGAAAGCTCCTAAAGCAGAGGGACCaTATTTTTATGTCCCAACTC

TCCTTAAGgCCTTGCCTATGATAGCACATCTCTTCAATAGAATTGTCCT (SEQ ID NO: 209)

| OLIGO | start | len | tm | gc % | any | 3' | seq (SEQ ID NOs: 210, 211) |
|---|---|---|---|---|---|---|---|
| LEFT PRIMER | 16 | 20 | 55.17 | 45.00 | 4.00 | 0.00 | TGAAAGCTCCTAAAGCAGAG |
| RIGHT PRIMER | 97 | 20 | 50.59 | 35.00 | 4.00 | 3.00 | TTGAAGAGATGTGCTATCAT |

SEQUENCE SIZE: 109
INCLUDED REGION SIZE: 109

PRODUCT SIZE: 82, PAIR ANY COMPL: 5.00, PAIR 3' COMPL: 1.00

```
  1 TTTTATTCATTAAGTTGAAAGCTCCTAAAGCAGAGGGACCaTATTTTTATGTCCCAACTC
                   >>>>>>>>>>>>>>>>>>>>

61 TCCTTAAGgCCTTGCCTATGATAGCACATCTCTTCAATAGAATTGTCCT
                <<<<<<<<<<<<<<<<<<<<
```

11 th group
75) Whole sequence ::: rs13047873-rs2837697

AAAGACCAGCTTTTAGCTGAACATCAGGGCTGCCTTCAGAGTTTAATTACCGCCCTCCCC

ATGGGGCCAAATGAGCCATCGACTCCTCCCAAGGGGGTTCgGCTTGGTACTGATCTTTAA

GTAAGTaAACGCTAAACCAGCTCATCTTAAAGCGCCCACATCTGATTTCCTGCTCTGCTG

TABLE 2-continued

CAAGACAGTAGGTGACTGGTAATGACC (SEQ ID NO: 214)

| OLIGO | start | len | tm | gc % | any | 3' | seq (SEQ ID NOs: 215, 216) |
|---|---|---|---|---|---|---|---|
| LEFT PRIMER | 26 | 20 | 59.08 | 50.00 | 5.00 | 2.00 | AGGGCTGCCTTCAGAGTTTA |
| RIGHT PRIMER | 155 | 20 | 59.62 | 50.00 | 5.00 | 2.00 | GCGCTTTAAGATGAGCTGGT |

SEQUENCE SIZE: 207
INCLUDED REGION SIZE: 207

PRODUCT SIZE: 130, PAIR ANY COMPL: 3.00, PAIR 3' COMPL: 1.00

```
  1 AAAGACCAGCTTTTAGCTGAACATCAGGGCTGCCTTCAGAGTTTAATTACCGCCCTCCCC
                              >>>>>>>>>>>>>>>>>>>>

61 ATGGGGCCAAATGAGCCATCGACTCCTCCCAAGGGGTTCgGCTTGGTACTGATCTTTAA

121 GTAAGTaAACGCTAAACCAGCTCATCTTAAAGCGCCCACATCTGATTTCCTGCTCTGCTG
                    <<<<<<<<<<<<<<<<<<<<

181 CAAGACAGTAGGTGACTGGTAATGACC
```

76) Whole sequence ::: rs455999-rs9305700

ACTCTGCTCCCAGTGTGAACATGGGGAAAGTTGATTAAACTCTCTGACTTCAGATTCCTC aTGTAAAATGTGGGGAAACAGCTCTGACTTAATGGTGTCACTGTGAGGAGTAAATGAGGT

AgCATATTTAAAGGATTTTGTATAGTGCTGGTGACAGTAACCAGCCAATAGATGATATAG

CTAGTAATAGCA (SEQ ID NO: 217)

| OLIGO | start | len | tm | gc % | any | 3' | seq (SEQ ID NOs: 218, 219) |
|---|---|---|---|---|---|---|---|
| LEFT PRIMER | 16 | 20 | 57.84 | 40.00 | 4.00 | 2.00 | TGAACATGGGGAAAGTTGAT |
| RIGHT PRIMER | 154 | 22 | 56.81 | 40.91 | 4.00 | 0.00 | TCACCAGCACTATACAAAATCC |

SEQUENCE SIZE: 192
INCLUDED REGION SIZE: 192

PRODUCT SIZE: 139, PAIR ANY COMPL: 4.00, PAIR 3' COMPL: 2.00

```
  1 ACTCTGCTCCCAGTGTGAACATGGGGAAAGTTGATTAAACTCTCTGACTTCAGATTCCTC
                    >>>>>>>>>>>>>>>>>>>>

61 aTGTAAAATGTGGGGAAACAGCTCTGACTTAATGGTGTCACTGTGAGGAGTAAATGAGGT

121 AgCATATTTAAAGGATTTTGTATAGTGCTGGTGACAGTAACCAGCCAATAGATGATATAG
                              <<<<<<<<<<<<<<<<<<<<<<

181 CTAGTAATAGCA
```

77) Whole sequence ::: rs9976207-rs455473 cttcactgaccacttccttaactgtccactccgaaacaccCcttcttcctgttcttccaa tacaccaaactctttcttgcctctgtgtgcttgcccatgctgttccttctggcttcttcc ttcACATTCAAGTCTTGACTTAGATGTCACTTGCCAAGGGAGACCTTGGA (SEQ ID NO: 220)

| OLIGO | start | len | tm | gc % | any | 3' | seq (SEQ NOs: 221, 222) |
|---|---|---|---|---|---|---|---|
| LEFT PRIMER | 12 | 21 | 54.96 | 47.62 | 4.00 | 0.00 | acttccttaactgtccactcc |
| RIGHT PRIMER | 159 | 19 | 54.64 | 47.37 | 7.00 | 2.00 | CCTTGGCAAGTGACATCTA |

SEQUENCE SIZE: 170
INCLUDED REGION SIZE: 170

PRODUCT SIZE: 148, PAIR ANY COMPL: 5.00, PAIR 3' COMPL: 3.00

```
  1 cttcactgaccacttccttaactgtccactccgaaacaccCcttcttcctgttcttccaa
                >>>>>>>>>>>>>>>>>>>>>

61 tacaccaaactctttcttgcctctgtgtgcttgcccatgctgttccttctggcttcttcc 121 ttcACATTCAAGTCTTGACTTAGATGTCACTTGCCAAGGGAGACCTTGGA
                              <<<<<<<<<<<<<<<<<<<
```

TABLE 2-continued

78) Whole sequence ::: rs2837807-rs2837808

AAACATCCCAATAGACAAAACTCCAAGAAGAGTCAAAACAAGAATAAAGTaCAGGTCATC

TTTTCTTTTGCACTCCTGACAGCACTTTGTACATGGTAATAATAATCTACCAATTAACTA

CATAAGCCACATGGTTTTATcATAGTGTGAAGCTTTGTATCCAGAAAGGAGAGAAGGCTCC (SEQ ID NO: 223)

| OLIGO | start | len | tm | gc % | any | 3' | seq (SEQ ID NOs: 224, 225) |
|---|---|---|---|---|---|---|---|
| LEFT PRIMER | 23 | 22 | 56.31 | 36.36 | 3.00 | 0.00 | CCAAGAAGAGTCAAAACAAGAA |
| RIGHT PRIMER | 172 | 21 | 56.19 | 42.86 | 4.00 | 2.00 | TCTCCTTTCTGGATACAAAGC |

SEQUENCE SIZE: 181
INCLUDED REGION SIZE: 181

PRODUCT SIZE: 150, PAIR ANY COMPL: 5.00, PAIR 3' COMPL: 1.00

```
  1 AAACATCCCAATAGACAAAACTCCAAGAAGAGTCAAAACAAGAATAAAGTaCAGGTCATC
                           >>>>>>>>>>>>>>>>>>>>>>

61 TTTTCTTTTGCACTCCTGACAGCACTTTGTACATGGTAATAATAATCTACCAATTAACTA

121 CATAAGCCACATGGTTTTATcATAGTGTGAAGCTTTGTATCCAGAAAGGAGAGAAGGCTC
                           <<<<<<<<<<<<<<<<<<<<<

181 C
```

79) Whole sequence ::: rs9974587-rs2776356

GGCAGAGGCATGGGGTGCATAGGGATATGGGGTGGGCCAGTTTGCTCCTCAGACCAGAAG

GGGTGCAGGAcTCCCCCCGATCAGGATCaTGGAGAAAGGTGTGGACAGAGGAAGGGAGGG

AGGGAGAAATGGCAGCTGCCCTGCAGTGG (SEQ ID NO: 226)

| OLIGO | start | len | tm | gc % | any | 3' | seq (SEQ NOs: 227, 228) |
|---|---|---|---|---|---|---|---|
| LEFT PRIMER | 42 | 20 | 60.52 | 55.00 | 3.00 | 2.00 | TTGCTCCTCAGACCAGAAGG |
| RIGHT PRIMER | 118 | 20 | 59.68 | 60.00 | 4.00 | 2.00 | CTCCCTTCCTCTGTCCACAC |

SEQUENCE SIZE: 149
INCLUDED REGION SIZE: 149

PRODUCT SIZE: 77, PAIR ANY COMPL: 5.00, PAIR 3' COMPL: 1.00

```
  1 GGCAGAGGCATGGGGTGCATAGGGATATGGGGTGGGCCAGTTTGCTCCTCAGACCAGAAG
                                             >>>>>>>>>>>>>>>>>>>>

61 GGGTGCAGGAcTCCCCCCGATCAGGATCaTGGAGAAAGGTGTGGACAGAGGAAGGGAGGG
      >                              <<<<<<<<<<<<<<<<<<<<

121 AGGGAGAAATGGCAGCTGCCCTGCAGTGG
```

80) Whole sequence ::: rs2838089-rs2838090 cagggactaagtgtctctgacaatacattcagccactactAcagtatgaagccagcccct catccccaccttcagagacccctggtgcctcagattcctcggccattctggagctgctgt gCCCGAGGCTTGTGTAGTTGGAGATCATTTTGGCAGTCAGTGCTG (SEQ ID NO: 229)

| OLIGO | start | len | tm | gc % | any | 3' | seq (SEQ ID NOs: 230, 231) |
|---|---|---|---|---|---|---|---|
| LEFT PRIMER | 12 | 22 | 55.48 | 40.91 | 5.00 | 2.00 | tgtctctgacaatacattcagc |
| RIGHT PRIMER | 160 | 20 | 55.81 | 45.00 | 4.00 | 2.00 | CTGACTGCCAAAATGATCTC |

SEQUENCE SIZE: 165
INCLUDED REGION SIZE: 165

PRODUCT SIZE: 149, PAIR ANY COMPL: 5.00, PAIR 3' COMPL: 1.00

```
  1 cagggactaagtgtctctgacaatacattcagccactactAcagtatgaagccagcccct
               >>>>>>>>>>>>>>>>>>>>>>

61 catccccaccttcagagacccctggtgcctcagattcctcggccattctggagctgctgt
```

TABLE 2-continued

```
121 gCCCGAGGCTTGTGTAGTTGGAGATCATTTTGGCAGTCAGTGCTG
          <<<<<<<<<<<<<<<<<<<<
```

12th group
81) Whole sequence ::: rs453592-rs380152

CCTGTCTCCGTGCGTGAAAGCCGGCTCCAAAGTGCCTTCTGTCCTATCTGCCTTCcGCAC

CTGGCTTTCCTGAAAGAAAGAAAACGCGTGGCTTATCTTTTCACGGCACGCCACCTTCAC

TCTCaCTTTTTCTTTTCTAATAAATACCTCTGGATGGGTTAGTGGTAATCTCTCCTCAAAC (SEQ ID NO: 232)

| OLIGO | start | len | tm | gc % | any | 3' | seq (SEQ ID NOs: 233, 234) |
|---|---|---|---|---|---|---|---|
| LEFT PRIMER | 24 | 20 | 60.00 | 55.00 | 4.00 | 1.00 | GCTCCAAAGTGCCTTCTGTC |
| RIGHT PRIMER | 165 | 20 | 58.87 | 55.00 | 3.00 | 2.00 | CCACTAACCCATCCAGAGGT |

SEQUENCE SIZE: 181
INCLUDED REGION SIZE: 181

PRODUCT SIZE: 142, PAIR ANY COMPL: 4.00, PAIR 3' COMPL: 1.00

```
  1 CCTGTCTCCGTGCGTGAAAGCCGGCTCCAAAGTGCCTTCTGTCCTATCTGCCTTCcGCAC
                            >>>>>>>>>>>>>>>>>>>>

61 CTGGCTTTCCTGAAAGAAAGAAAACGCGTGGCTTATCTTTTCACGGCACGCCACCTTCAC

121 TCTCaCTTTTTCTTTTCTAATAAATACCTCTGGATGGGTTAGTGGTAATCTCTCCTCAAA
                              <<<<<<<<<<<<<<<<<<<<

181 C
```

82) Whole sequence ::: rs442723-rs449888

GGGAGCACAACCTAGGCCCCTCCTGGGGAGGTGGTGGAGTCAGAATCACGTAAGAGaCAA

AGTTCCAGTCCCTCAGTGCCGGCTCCATTGTCCCCTGGACTTCCCTTACAAACCACAGAT

GCAAAGAGAGCACTTCTCgGAATCTCCACACAGCCACGGTGGAGCACTCAACCCACGCGA

CCCTCGGGCGCAGGTGCT (SEQ ID NO: 235)

| OLIGO | start | len | tm | gc % | any | 3' | seq (SEQ ID NOs: 236, 237) |
|---|---|---|---|---|---|---|---|
| LEFT PRIMER | 23 | 20 | 65.82 | 65.00 | 3.00 | 1.00 | CTGGGGAGGTGGTGGAGTCA |
| RIGHT PRIMER | 169 | 20 | 66.12 | 65.00 | 7.00 | 1.00 | GAGTGCTCCACCGTGGCTGT |

SEQUENCE SIZE: 198
INCLUDED REGION SIZE: 198

PRODUCT SIZE: 147, PAIR ANY COMPL: 7.00, PAIR 3' COMPL: 1.00

```
  1 GGGAGCACAACCTAGGCCCCTCCTGGGGAGGTGGTGGAGTCAGAATCACGTAAGAGaCAA
                           >>>>>>>>>>>>>>>>>>>>

61 AGTTCCAGTCCCTCAGTGCCGGCTCCATTGTCCCCTGGACTTCCCTTACAAACCACAGAT

121 GCAAAGAGAGCACTTCTCgGAATCTCCACACAGCCACGGTGGAGCACTCAACCCACGCGA
                              <<<<<<<<<<<<<<<<<<<<

181 CCCTCGGGCGCAGGTGCT
```

83) Whole sequence ::: rs375886-rs9976560

CCTGAGAAGCTTCCAGCAAAGCACCAGCACGAACCGCCCCACCTCCCCACCTCCCCGCAA

GCGTTGcCGGGACTGACAGATTACAGAGCTCTGgTCCCTCTGCACTCCTGCTCTGCCACC

CCCAGGGTGTCAGAATGTGCCCCCCACACAGTTTCCAAAAG (SEQ ID NO: 238)

| OLIGO | start | len | tm | gc % | any | 3' | seq (SEQ ID NOs: 239, 240) |
|---|---|---|---|---|---|---|---|
| LEFT PRIMER | 18 | 18 | 59.84 | 55.56 | 2.00 | 0.00 | AAAGCACCAGCACGAACC |
| RIGHT PRIMER | 143 | 18 | 59.89 | 61.11 | 3.00 | 3.00 | GGGGCACATTCTGACACC |

SEQUENCE SIZE: 161
INCLUDED REGION SIZE: 161

PRODUCT SIZE: 126, PAIR ANY COMPL: 3.00, PAIR 3' COMPL: 0.00

TABLE 2-continued

```
  1 CCTGAGAAGCTTCCAGCAAAGCACCAGCACGAACCGCCCCACCTCCCCACCTCCCCGCAA
               >>>>>>>>>>>>>>>>>

61 GCGTTGcCGGGACTGACAGATTACAGAGCTCTGgTCCCTCTGCACTCCTGCTCTGCCACC

121 CCCAGGGTGTCAGAATGTGCCCCCCACACAGTTTCCAAAAG
       <<<<<<<<<<<<<<<
```

84) Whole sequence ::: rs3819900-rs3819901

ATGGAGCTGCTGCGCCGGCCTGAGCTCTGATCCCTCCTCCGACCCAGCCTCACCCTGCaA

GCAGCACCATGTGGGGCTCAGAATGGGGATCTTAAGGGACCCTcCCCACAACCTCCCGAT

AAGCCTTTCCACGGAGGGCCCAAGCGGAGACAGGAGAACACT (SEQ ID NO: 241)

| OLIGO | start | len | tm | gc % | any | 3' | seq (SEQ ID NOs: 242, 243) |
|---|---|---|---|---|---|---|---|
| LEFT PRIMER | 20 | 19 | 57.00 | 57.89 | 6.00 | 0.00 | CTGAGCTCTGATCCCTCCT |
| RIGHT PRIMER | 158 | 18 | 57.51 | 55.56 | 2.00 | 0.00 | TTCTCCTGTCTCCGCTTG |

SEQUENCE SIZE: 162
INCLUDED REGION SIZE: 162

PRODUCT SIZE: 139, PAIR ANY COMPL: 3.00, PAIR 3' COMPL: 0.00

```
  1 ATGGAGCTGCTGCGCCGGCCTGAGCTCTGATCCCTCCTCCGACCCAGCCTCACCCTGCaA
                        >>>>>>>>>>>>>>>>>>>

61 GCAGCACCATGTGGGGCTCAGAATGGGGATCTTAAGGGACCCTcCCCACAACCTCCCGAT

121 AAGCCTTTCCACGGAGGGCCCAAGCGGAGACAGGAGAACACT
                    <<<<<<<<<<<<<<<<<<
```

85) Whole sequence ::: rs10451852-rs10451853

ACTTTCAGAATGTGCTGCCTTCCACGTGTGAACCAGACTGAGCTCCTTTCTGCCACTGAT

GTTGAATTGTCCATTTGCTCACaTCAGTGTCCACGTGGCAAATCCACAGGGCgTGGGTGG

GATCCTGCAGTCTAGACAAAGCCAAGGAGCACCGCTGGAGGCCACGTTGGGCTTCCCAAT

CCACATGCAAACCC (SEQ ID NO: 244)

| OLIGO | start | len | tm | gc % | any | 3' | seq (SEQ ID NOs: 245, 246) |
|---|---|---|---|---|---|---|---|
| LEFT PRIMER | 45 | 20 | 59.29 | 50.00 | 3.00 | 1.00 | CCTTTCTGCCACTGATGTTG |
| RIGHT PRIMER | 190 | 19 | 60.46 | 47.37 | 4.00 | 0.00 | TTGCATGTGGATTGGGAAG |

SEQUENCE SIZE: 194
INCLUDED REGION SIZE: 194

PRODUCT SIZE: 146, PAIR ANY COMPL: 4.00, PAIR 3' COMPL: 0.00

```
  1 ACTTTCAGAATGTGCTGCCTTCCACGTGTGAACCAGACTGAGCTCCTTTCTGCCACTGAT
                                             >>>>>>>>>>>>>>>>>

61 GTTGAATTGTCCATTTGCTCACaTCAGTGTCCACGTGGCAAATCCACAGGGCgTGGGTGG
     >>>>

121 GATCCTGCAGTCTAGACAAAGCCAAGGAGCACCGCTGGAGGCCACGTTGGGCTTCCCAAT
                                                       <<<<<<<<

181 CCACATGCAAACCC
       <<<<<<<<
```

86) Whole sequence ::: rs7278528-rs11701158

TCTCCAGCCAGCGTGTCACAAAGCCGCTCACCTGCTCGTGTGAGTGTCTGAATGCACGTG

TTTGAGTGTCAGaGGCGTGTGAACCACAGCAACTCAATCTTGAATAGGGGCTGGGTAAAG

TGAGGCTgAGACCTCCCGGGGCTGCATTCCCAGATGGTTAAGGCATTCTAAGTCACAAGA

TGAGATAGGAAGTTCGCACAAGACACTGGTCAT (SEQ ID NO: 247)

| OLIGO | start | len | tm | gc % | any | 3' | seq (SEQ ID NOs: 248, 249) |
|---|---|---|---|---|---|---|---|
| LEFT PRIMER | 28 | 20 | 60.53 | 55.00 | 4.00 | 0.00 | TCACCTGCTCGTGTGAGTGT |

TABLE 2-continued

```
RIGHT PRIMER 163    20  59.39  50.00  4.00 2.00 CCTTAACCATCTGGGAATGC

SEQUENCE SIZE: 213
INCLUDED REGION SIZE: 213

PRODUCT SIZE: 136, PAIR ANY COMPL: 3.00, PAIR 3' COMPL: 0.00

1 TCTCCAGCCAGCGTGTCACAAAGCCGCTCACCTGCTCGTGTGAGTGTCTGAATGCACGTG
                    >>>>>>>>>>>>>>>>>>>>

61 TTTGAGTGTCAGaGGCGTGTGAACCACAGCAACTCAATCTTGAATAGGGGCTGGGTAAAG

121 TGAGGCTgAGACCTCCCGGGGCTGCATTCCCAGATGGTTAAGGCATTCTAAGTCACAAGA
                      <<<<<<<<<<<<<<<<<<<<

181 TGAGATAGGAAGTTCGCACAAGACACTGGTCAT
```

87) Whole sequence ::: rs2839627-rs170916

TTGAGTCCTCTTAAGTAGTTACTATAGTGGAGAACTTGAGTCATTCTTTGTAGCGTGCTT cGTAGAGCAGCGTGTTTGTTAGAAGGATTTGTTAATCCTGTATAGgGTCTTTACGAAGGC

TGTTTTCATGGAAGCTTCTCTTTGTTGACTCC (SEQ ID NO: 250)

```
OLIGO          start   len    tm    gc %   any   3'   seq (SEQ ID NOs: 251, 252)

LEFT PRIMER     28     22   55.68  36.36  5.00  1.00 TGGAGAACTTGAGTCATTCTTT
RIGHT PRIMER   152     19   52.33  47.37  3.00  2.00 GGAGTCAACAAAGAGAAGC

SEQUENCE SIZE: 152
INCLUDED REGION SIZE: 152

PRODUCT SIZE: 125, PAIR ANY COMPL: 5.00, PAIR 3' COMPL: 3.00

1 TTGAGTCCTCTTAAGTAGTTACTATAGTGGAGAACTTGAGTCATTCTTTGTAGCGTGCTT
                             >>>>>>>>>>>>>>>>>>>>>>

61 cGTAGAGCAGCGTGTTTGTTAGAAGGATTTGTTAATCCTGTATAGgGTCTTTACGAAGGC

121 TGTTTTCATGGAAGCTTCTCTTTGTTGACTCC
             <<<<<<<<<<<<<<<<<<<
```

88) Whole sequence ::: rs2839628-rs234740

CATTCTCTCCAGCTGCAAACTTTCTTCAACTTTCCTAAATTCTTAcTAAATTCAGAGGAA

TAGGATAAAGATCACTTAGAGAAAGGGTGCTTATGGACATAGCCTGAGTTTCCTTTAACC

TCTCTgCAATGGGTGCTTTTAACTAGCTTCTACATGGCAAGCTGTTTCAGTTTG (SEQ ID NO: 253)

```
OLIGO          start   len    tm    gc %   any   3'   seq (SEQ ID NOs: 254, 255)

LEFT PRIMER     20     21   50.06  28.57  3.00  2.00 CTTTCTTCAACTTTCCTAAAT
RIGHT PRIMER   160     19   50.96  42.11  4.00  2.00 TTGCCATGTAGAAGCTAGT

SEQUENCE SIZE: 174
INCLUDED REGION SIZE: 174

PRODUCT SIZE: 141, PAIR ANY COMPL: 5.00, PAIR 3' COMPL: 2.00

1 CATTCTCTCCAGCTGCAAACTTTCTTCAACTTTCCTAAATTCTTAcTAAATTCAGAGGAA
                         >>>>>>>>>>>>>>>>>>>>>

61 TAGGATAAAGATCACTTAGAGAAAGGGTGCTTATGGACATAGCCTGAGTTTCCTTTAACC

121 TCTCTgCAATGGGTGCTTTTAACTAGCTTCTACATGGCAAGCTGTTTCAGTTTG
                     <<<<<<<<<<<<<<<<<<<
```

89) Whole sequence ::: rs2838239-rs2838240

GGACATCTGGAACTGCACCAGCACAGAACCGACACGTTGTTAcTCATCGTCACTCGGCAG

GGCTGAAGACCACCAGAACTCATGACAGGCAGACGTGCCTGGCCCAGTTGAGGATGTAGC tTCAGAGCCAAGCGCCAGTCCTGTTGGCCACGTGGGCTGGGGGCAGGATAGACCA (SEQ ID NO: 256)

```
OLIGO          start   len    tm    gc %   any   3'   seq (SEQ ID NOs: 257, 258)

LEFT PRIMER     17     19   59.73  57.89  2.00  0.00 ACCAGCACAGAACCGACAC
```

TABLE 2-continued

```
RIGHT PRIMER  145      18     62.40  61.11  4.00 0.00  AACAGGACTGGCGCTTGG

SEQUENCE SIZE: 175
INCLUDED REGION SIZE: 175

PRODUCT SIZE: 129, PAIR ANY COMPL: 4.00, PAIR 3' COMPL: 1.00

1 GGACATCTGGAACTGCACCAGCACAGAACCGACACGTTGTTACTCATCGTCACTCGGCAG
             >>>>>>>>>>>>>>>>>>

61 GGCTGAAGACCACCAGAACTCATGACAGGCAGACGTGCCTGGCCCAGTTGAGGATGTAGC 121 tTCAGAGCCAAGCGCCAGTCCTGTTGGCCACGTGGGCTGGGGGCAGGATAGACCA
              <<<<<<<<<<<<<<<<<<
```

90) Whole sequence ::: rs630397-rs11089106

GGCTGGTTCTGCCCTTGGGAGGTGGTTCCTTTGGCTGGACCAGAATGTCTGaAGATGATC

AGGAGAGGGCCAAGGGTTGGGGGGTGCCCCATGTGCACCCTGAGAATTGCACCAGGCACA

GtGAGCAACTTCAGCCCTCCTTGTGCAGAGCTGCAGCGTACAGTGCCAGCCCTCGCTGGC

CC (SEQ ID NO: 259)

```
OLIGO          start   len    tm     gc %   any  3'   seq (SEQ ID NOs: 260, 261)

LEFT PRIMER    14      20     61.79  55.00  3.00 0.00  CTTGGGAGGTGGTTCCTTTG
RIGHT PRIMER   148     18     61.15  61.11  4.00 1.00  CTGCACAAGGAGGGCTGA

SEQUENCE SIZE: 182
INCLUDED REGION SIZE: 182

PRODUCT SIZE: 135, PAIR ANY COMPL: 5.00, PAIR 3' COMPL: 0.00

1 GGCTGGTTCTGCCCTTGGGAGGTGGTTCCTTTGGCTGGACCAGAATGTCTGaAGATGATC
                   >>>>>>>>>>>>>>>>>>>>

61 AGGAGAGGGCCAAGGGTTGGGGGGTGCCCCATGTGCACCCTGAGAATTGCACCAGGCACA

121 GtGAGCAACTTCAGCCCTCCTTGTGCAGAGCTGCAGCGTACAGTGCCAGCCCTCGCTGGC
              <<<<<<<<<<<<<<<<<<

181 CC
```

91) Whole sequence ::: rs9637180-rs481767

GTTCTCACTTTACTGAGAAACCTGGCAGCTTCTCAGGCCACCGCCCAGGTCACCTGCTCA

CCAGCAAcGTGAACCACAGGAACtGAGGCTGTGCGGGAGGCGGCTCTGCTCTGTGCTGGG

CCCCCCTCCTCCTCACTCACCCTCTTCAGTCAAAG (SEQ ID NO: 262)

```
OLIGO          start   len    tm     gc %   any  3'   seq (SEQ ID NOs: 263, 264)

LEFT PRIMER    11      20     57.70  50.00  5.00 5.00  TACTGAGAAACCTGGCAGCT
RIGHT PRIMER   155     20     54.98  50.00  3.00 0.00  CTTTGACTGAAGAGGGTGAG

SEQUENCE SIZE: 155
INCLUDED REGION SIZE: 155

PRODUCT SIZE: 145, PAIR ANY COMPL: 3.00, PAIR 3' COMPL: 2.00

1 GTTCTCACTTTACTGAGAAACCTGGCAGCTTCTCAGGCCACCGCCCAGGTCACCTGCTCA
                 >>>>>>>>>>>>>>>>>>>>

61 CCAGCAAcGTGAACCACAGGAACtGAGGCTGTGCGGGAGGCGGCTCTGCTCTGTGCTGGG

121 CCCCCCTCCTCCTCACTCACCCTCTTCAGTCAAAG
                   <<<<<<<<<<<<<<<<<<<<
```

92) Whole sequence ::: rs162360-rs162359

TTAGTATTATTATTTTCATATATATTTTTATAATAATCATATATTCAATTTTATCATCA

AGAAAAAAGTTTTAAAATTCaAAATCCTTTCATGTGCACTGTTTTAAACTtAGGTAGAAG

AAAAAAAGTCACTGAAAATCCAAGATGTAATAAACAGGCCCAACAAAGGCCAACAAACTT (SEQ ID NO: 265)

TABLE 2-continued

| OLIGO | start | len | tm | gc % | any | 3' | seq (SEQ ID NOs: 266, 267) |
|---|---|---|---|---|---|---|---|
| LEFT PRIMER | 45 | 20 | 48.37 | 20.00 | 5.00 | 3.00 | TTCAATTTTATCATCAAGAA |
| RIGHT PRIMER | 163 | 20 | 55.18 | 40.00 | 4.00 | 1.00 | TTGGGCCTGTTTATTACATC |

SEQUENCE SIZE: 180
INCLUDED REGION SIZE: 180

PRODUCT SIZE: 119, PAIR ANY COMPL: 4.00, PAIR 3' COMPL: 1.00

```
  1 TTAGTATTATTATTTTCATATATATTTTTTATAATAATCATATATTCAATTTTATCATCA
                                                 >>>>>>>>>>>>>>>
 61 AGAAAAAAGTTTTAAAATTCaAAATCCTTTCATGTGCACTGTTTTAAACTtAGGTAGAAG
    >>>>
121 AAAAAAAGTCACTGAAAATCCAAGATGTAATAAACAGGCCCAACAAAGGCCAACAAACTT
                     <<<<<<<<<<<<<<<<<<<<
```

93) Whole sequence ::: rs162356-rs162355

AGGGAACATGGCCTTGCCCACACAGATTTCAGACATCTGGCTCCAGAACTGTGGGAGGAC

ACATTTCTGTTGTTTAGAACTGCaTGTTTTTTATACTTTGTTATGGCTGCCCTAGGcAAC

TAATACAGATATTATTTTCCACTTCTGAACTTAGCAAAATATTTTTAAAATGAAAATTCT

TAAATGTTGGCACAGT (SEQ ID NO: 268)

| OLIGO | start | len | tm | gc % | any | 3' | seq (SEQ ID NOs: 269, 270) |
|---|---|---|---|---|---|---|---|
| LEFT PRIMER | 14 | 20 | 60.24 | 45.00 | 3.00 | 3.00 | TTGCCCACACAGATTTCAGA |
| RIGHT PRIMER | 156 | 22 | 56.88 | 36.36 | 5.00 | 0.00 | TGCTAAGTTCAGAAGTGGAAAA |

SEQUENCE SIZE: 196
INCLUDED REGION SIZE: 196

PRODUCT SIZE: 143, PAIR ANY COMPL: 4.00, PAIR 3' COMPL: 2.00

```
  1 AGGGAACATGGCCTTGCCCACACAGATTTCAGACATCTGGCTCCAGAACTGTGGGAGGAC
                 >>>>>>>>>>>>>>>>>>>>
 61 ACATTTCTGTTGTTTAGAACTGCaTGTTTTTTATACTTTGTTATGGCTGCCCTAGGcAAC
121 TAATACAGATATTATTTTCCACTTCTGAACTTAGCAAAATATTTTTAAAATGAAAATTCT
                         <<<<<<<<<<<<<<<<<<<<<<
181 TAAATGTTGGCACAGT
```

94) Whole sequence ::: rs91424-rs463738

CTGGATAAAGGATGCTACACGTCCCTGGTGGGACAGAGCAGGACGGCAGGGGATTTCATT

AcGCCAcTCAGAATGGCAGGCAATTGAAAAAACTTATAAATTGTTTATTTCCAGAATTTT (SEQ ID NO: 271)

| OLIGO | start | len | tm | gc % | any | 3' | seq (SEQ ID NOs: 272, 273) |
|---|---|---|---|---|---|---|---|
| LEFT PRIMER | 3 | 20 | 54.33 | 45.00 | 4.00 | 4.00 | GGATAAAGGATGCTACACGT |
| RIGHT PRIMER | 120 | 20 | 49.40 | 20.00 | 4.00 | 0.00 | AAAATTCTGGAAATAAACAA |

SEQUENCE SIZE: 120
INCLUDED REGION SIZE: 120

PRODUCT SIZE: 118, PAIR ANY COMPL: 3.00, PAIR 3' COMPL: 1.00

```
  1 CTGGATAAAGGATGCTACACGTCCCTGGTGGGACAGAGCAGGACGGCAGGGGATTTCATT
      >>>>>>>>>>>>>>>>>>>>
 61 AcGCCAcTCAGAATGGCAGGCAATTGAAAAAACTTATAAATTGTTTATTTCCAGAATTTT
                                         <<<<<<<<<<<<<<<<<<<<
```

95) Whole sequence ::: rs2838318-rs2838319

TGTCAGTGGTGTAATCCGACTGTGAAAGATCAGTCTAACAAAACAGCGGGGAGAGAGAGG

GCTGAATCAGAGCaACTAGGTCCAAAGCCGAGGGAACCACCAACAGATCCCCTGGTGACC

CAACAAGAAATGCTCACAGTCTGGACCCAgTCAGAGTCTGCAGGACACAGCAGACATTCT

TABLE 2-continued

GGAAGTTACAACAGCCAGGAGCAAGAGGACGCATGGCCTGACTG (SEQ ID NO: 274)

| OLIGO | start | len | tm | gc % | any | 3' | seq (SEQ ID NOs: 275, 276) |
|---|---|---|---|---|---|---|---|
| LEFT PRIMER | 49 | 20 | 60.30 | 60.00 | 3.00 | 3.00 | GGGAGAGAGAGGGCTGAATC |
| RIGHT PRIMER | 202 | 21 | 59.00 | 52.38 | 4.00 | 2.00 | GCTCCTGGCTGTTGTAACTTC |

SEQUENCE SIZE: 224
INCLUDED REGION SIZE: 224

PRODUCT SIZE: 154, PAIR ANY COMPL: 4.00, PAIR 3' COMPL: 1.00

```
  1 TGTCAGTGGTGTAATCCGACTGTGAAAGATCAGTCTAACAAAACAGCGGGGAGAGAGAGG
                                                 >>>>>>>>>>>

61 GCTGAATCAGAGCaACTAGGTCCAAAGCCGAGGGAACCACCAACAGATCCCCTGGTGACC
    >>>>>>>>

121 CAACAAGAAATGCTCACAGTCTGGACCCAgTCAGAGTCTGCAGGACACAGCAGACATTCT

181 GGAAGTTACAACAGCCAGGAGCAAGAGGACGCATGGCCTGACTG
    <<<<<<<<<<<<<<<<<<<<<
```

96) Whole sequence ::: rs915770-rs731935

CGCCAGAGCACCCCTTCTCAGAACAGAAAGCGTCTCTACAaAGTGATCCGGAAGTGAGTG

TGTGAGGGCGCTGCGTCCTCCCTGCTCCCCTTGGAGTTGCCCTTTCTTGCTCAGATCTGG

GTGCCTTgGCCTTGTCCTGGGCCCTTCCGCAGCCCCGGGGTGATCCCCGCTAG (SEQ ID NO: 277)

| OLIGO | start | len | tm | gc % | any | 3' | seq (SEQ ID NOs: 278, 279) |
|---|---|---|---|---|---|---|---|
| LEFT PRIMER | 3 | 19 | 60.95 | 63.16 | 3.00 | 3.00 | CCAGAGCACCCCTTCTCAG |
| RIGHT PRIMER | 148 | 18 | 62.95 | 66.67 | 6.00 | 0.00 | GGAAGGGCCCAGGACAAG |

SEQUENCE SIZE: 174
INCLUDED REGION SIZE: 174

PRODUCT SIZE: 146, PAIR ANY COMPL: 6.00, PAIR 3' COMPL: 2.00

```
  1 CGCCAGAGCACCCCTTCTCAGAACAGAAAGCGTCTCTACAaAGTGATCCGGAAGTGAGTG
      >>>>>>>>>>>>>>>>>>>

61 TGTGAGGGCGCTGCGTCCTCCCTGCTCCCCTTGGAGTTGCCCTTTCTTGCTCAGATCTGG

121 GTGCCTTgGCCTTGTCCTGGGCCCTTCCGCAGCCCCGGGGTGATCCCCGCTAG
             <<<<<<<<<<<<<<<<<<
```

Final Set
97) Whole sequence ::: rs1573338-rs1573339

TATCTTACGGATTTGTCAACATCATTTGAGAAGAAGTCCATAGGCTCAGCAGATTTTTAT

GCCAGGTGGGCCATGGCATAAAAATGTGAAGAATGTGCTCaCTTAGACAATACcTGTGCT

AAAATTGGAACAATACAGAGAAGATTAGCAAATTAAAACAATGTTAGGAAGTCAGTGTGG

TGAGGTACGGTGCCTCATGCC (SEQ ID NO: 280)

| OLIGO | start | len | tm | gc % | any | 3' | seq (SEQ ID NOs: 281, 282) |
|---|---|---|---|---|---|---|---|
| LEFT PRIMER | 47 | 21 | 59.24 | 42.86 | 3.00 | 1.00 | CAGCAGATTTTTATGCCAGGT |
| RIGHT PRIMER | 192 | 20 | 60.06 | 60.00 | 4.00 | 3.00 | CACCGTACCTCACCACACTG |

SEQUENCE SIZE: 201
INCLUDED REGION SIZE: 201

PRODUCT SIZE: 146, PAIR ANY COMPL: 4.00, PAIR 3' COMPL: 3.00

```
  1 TATCTTACGGATTTGTCAACATCATTTGAGAAGAAGTCCATAGGCTCAGCAGATTTTTAT
                                                 >>>>>>>>>>>>

61 GCCAGGTGGGCCATGGCATAAAAATGTGAAGAATGTGCTCaCTTAGACAATACcTGTGCT
    >>>>>>>>

121 AAAATTGGAACAATACAGAGAAGATTAGCAAATTAAAACAATGTTAGGAAGTCAGTGTGG
                                                     <<<<<<<<

181 TGAGGTACGGTGCCTCATGCC
```

TABLE 2-continued

<<<<<<<<<<

98) Whole sequence ::: rs3788094-rs3788095

AGGCAGGGCCCTCCTTGCCACATGTAAAGCTGCACAGAGCGGTCACTATATGTGTTTCCA

TATTTGCAATCCAACCACCACCAACTGAGTGTGCGTCCTGaTCAGCCGAGCCTGCCCACG

GTGGCCACAGGCCCTCTACATTCTAATCTCGAGAGCCTGAGCATGTACAAATTAAACgAA

GCAAAACGACACCACCCAGTTCTGGCCGTACTATAGGAGGTTTCCAGGAAGGGTTTGTGA

ACATAAACATAAGCTAGGTAACACTCCTTTCTGAA (SEQ ID NO: 283)

| OLIGO | start | len | tm | gc % | any | 3' | seq. (SEQ ID NOs: 284, 285) |
|---|---|---|---|---|---|---|---|
| LEFT PRIMER | 73 | 20 | 57.88 | 50.00 | 5.00 | 3.00 | AACCACCACCAACTGAGTGT |
| RIGHT PRIMER | 220 | 20 | 56.94 | 55.00 | 6.00 | 2.00 | CCTCCTATAGTACGGCCAGA |

SEQUENCE SIZE: 275
INCLUDED REGION SIZE: 275

PRODUCT SIZE: 148, PAIR ANY COMPL: 3.00, PAIR 3' COMPL: 1.00

1 AGGCAGGGCCCTCCTTGCCACATGTAAAGCTGCACAGAGCGGTCACTATATGTGTTTCCA

61 TATTTGCAATCCAACCACCACCAACTGAGTGTGCGTCCTGaTCAGCCGAGCCTGCCCACG
             >>>>>>>>>>>>>>>>>>>>

121 GTGGCCACAGGCCCTCTACATTCTAATCTCGAGAGCCTGAGCATGTACAAATTAAACgAA

181 GCAAAACGACACCACCCAGTTCTGGCCGTACTATAGGAGGTTTCCAGGAAGGGTTTGTGA
                        <<<<<<<<<<<<<<<<<<<<

241 ACATAAACATAAGCTAGGTAACACTCCTTTCTGAA

99) Whole sequence ::: rs756554-rs756555

TCAGAGCATCGCCTCAGTGGCCATCAATAGCTCGGGGGACTGGATTGCTTTTGGCTGTTC

AGGTTTGTCCCCaGCCTGGGTGGTAGAGATGGACTCCCCATTAGGGACCAGTGCTGCCCG

GCTACAGGCtTACTTGACAGCCACCCACTGGGGGTGCCCTCCCCTCCCCAGTTGTCTTC

CATGGGGTGCCCTCTCCCCCAGCCGCCTTTCAGAAGGGGCCCTCCCCTCC (SEQ ID NO: 286)

| OLIGO | start | len | tm | gc % | any | 3' | seq (SEQ ID NOs: 287, 288) |
|---|---|---|---|---|---|---|---|
| LEFT PRIMER | 41 | 20 | 61.15 | 45.00 | 2.00 | 0.00 | TGGATTGCTTTTGGCTGTTC |
| RIGHT PRIMER | 189 | 20 | 61.37 | 55.00 | 6.00 | 2.00 | CACCCCATGGAAGACAACTG |

SEQUENCE SIZE: 230
INCLUDED REGION SIZE: 230

PRODUCT SIZE: 149, PAIR ANY COMPL: 4.00, PAIR 3' COMPL: 2.00

1 TCAGAGCATCGCCTCAGTGGCCATCAATAGCTCGGGGGACTGGATTGCTTTTGGCTGTTC
                                            >>>>>>>>>>>>>>>>>>>>

61 AGGTTTGTCCCCaGCCTGGGTGGTAGAGATGGACTCCCCATTAGGGACCAGTGCTGCCCG

121 GCTACAGGCtTACTTGACAGCCACCCACTGGGGGTGCCCTCCCCTCCCCAGTTGTCTTC
                                                   <<<<<<<<<<<

181 CATGGGGTGCCCTCTCCCCCAGCCGCCTTTCAGAAGGGGCCCTCCCCTCC
       <<<<<<<<<

100) Whole sequence ::: rs4350841-rs2838545

CTCATGCTTACATCCTTAGCTGATCATTAAACTTTGTGACCATTTCATGCTCACTGCTTT

CTTGCCcGGGAGCTAATGGTGAGGAAAGGTCACTGGGAACCAGCGCACCAACCTCAGACA

TcGATTTTGTTCCAGCCTTTTTTCCTGGGCAGGGGTGGCTATCACCTGCTGGTAGGCAGC

GGCAGGCCCACTGTCCTGC (SEQ ID NO: 289)

| OLIGO | start | len | tm | gc % | any | 3' | seq (SEQ ID NOs: 290, 291) |
|---|---|---|---|---|---|---|---|
| LEFT PRIMER | 27 | 21 | 53.45 | 28.57 | 5.00 | 2.00 | TTAAACTTTGTGACCATTTCA |

TABLE 2-continued

```
RIGHT PRIMER 174    18   54.55 55.56 6.00 2.00 TACCAGCAGGTGATAGCC

SEQUENCE SIZE: 199
INCLUDED REGION SIZE: 199

PRODUCT SIZE: 148, PAIR ANY COMPL: 3.00, PAIR 3' COMPL: 0.00

1 CTCATGCTTACATCCTTAGCTGATCATTAAACTTTGTGACCATTTCATGCTCACTGCTTT
                   >>>>>>>>>>>>>>>>>>>>

61 CTTGCCcGGGAGCTAATGGTGAGGAAAGGTCACTGGGAACCAGCGCACCAACCTCAGACA

121 TcGATTTTGTTCCAGCCTTTTTTCCTGGGCAGGGGTGGCTATCACCTGCTGGTAGGCAGC
                                           <<<<<<<<<<<<<<<<<<

181 GGCAGGCCCACTGTCCTGC
```

101) Whole sequence ::: rs2838551-rs2838552

TGACAGAAAAGTCTCAGAGCAGTGCCTTCTGAGCTCTTCTACACCAAGCAGGCAGAATGT

TCACTGCTAATGAGgCTGGAGCTGGTCCCCAGCAGTGGTAGGAAGCTTCCAaCAGGCTCA

GGCTGTGGGTGCTTGCAGGGGCACAGTGTGACGGCCACGGGCCTCAGAGCTCTGGTGGGC (SEQ ID NO: 292)

T

```
OLIGO          start   len   tm    gc %  any   3'   seq (SEQ ID NOs: 293, 294)

LEFT PRIMER      2     20   53.05 45.00 5.00 3.00 GACAGAAAAGTCTCAGAGCA
RIGHT PRIMER   135     18   62.10 61.11 5.00 3.00 CAAGCACCCACAGCCTGA

SEQUENCE SIZE: 181
INCLUDED REGION SIZE: 181

PRODUCT SIZE: 134, PAIR ANY COMPL: 4.00, PAIR 3' COMPL: 3.00

1 TGACAGAAAAGTCTCAGAGCAGTGCCTTCTGAGCTCTTCTACACCAAGCAGGCAGAATGT
       >>>>>>>>>>>>>>>>>>>>

61 TCACTGCTAATGAGgCTGGAGCTGGTCCCCAGCAGTGGTAGGAAGCTTCCAaCAGGCTCA
                                                              <<<

121 GGCTGTGGGTGCTTGCAGGGGCACAGTGTGACGGCCACGGGCCTCAGAGCTCTGGTGGGC
       <<<<<<<<<<<<<<<

181 T
```

102) Whole sequence ::: rs8134902-rs8133874

ACATCTTTCTCAAATAAAGATAACAGCGATGTATTTTCACAAAAGCAAGAGCTTAGAAAG

TACTcCACCCAGGTATCCCTCTTGGAAAAAATaCTTAAGGAAATATGACAAATGGCAAAG

TGATTGTTATGGATGGAATGTTTGTATCCTCCCAAAATTCACATGTTGAGACCCTAATTC (SEQ ID NO: 295)

CAATATG

```
OLIGO          start   len   tm    gc %  any   3'   seq (SEQ ID NOs: 296, 297)

LEFT PRIMER     33     20   54.84 35.00 5.00 2.00 ATTTTCACAAAAGCAAGAGC
RIGHT PRIMER   155     20   54.97 40.00 3.00 0.00 TTGGGAGGATACAAACATTC

SEQUENCE SIZE: 187
INCLUDED REGION SIZE: 187

PRODUCT SIZE: 123, PAIR ANY COMPL: 4.00, PAIR 3' COMPL: 0.00

1 ACATCTTTCTCAAATAAAGATAACAGCGATGTATTTTCACAAAAGCAAGAGCTTAGAAAG
                                       >>>>>>>>>>>>>>>>>>>>

61 TACTcCACCCAGGTATCCCTCTTGGAAAAAATaCTTAAGGAAATATGACAAATGGCAAAG

121 TGATTGTTATGGATGGAATGTTTGTATCCTCCCAAAATTCACATGTTGAGACCCTAATTC
                      <<<<<<<<<<<<<<<<<<<<

181 CAATATG
```

TABLE 2-continued

103) Whole sequence ::: rs425667-rs382478

AGGGGCATTCTACAAAACACCCAACCGGTCAAGGTCGCTGAGGCCAAGGAGAGATTGGGC

AACCGTCACAAACCAGAGAAGcCGAGGAGAcCTTTCAGCCAACGCCATGTGGGGTCCTGA

GCAGGACCCACCGGAAGTTGGTGCAGCTGCCTAAAGACCGTCCTGGCTGAGAAGAAACAG (SEQ ID NO: 298)

| OLIGO | start | len | tm | gc % | any | 3' | seq (SEQ ID NOs: 299, 300) |
|---|---|---|---|---|---|---|---|
| LEFT PRIMER | 46 | 18 | 55.06 | 50.00 | 4.00 | 2.00 | AAGGAGAGATTGGGCAAC |
| RIGHT PRIMER | 178 | 19 | 54.85 | 52.63 | 3.00 | 1.00 | GTTTCTTCTCAGCCAGGAC |

SEQUENCE SIZE: 180
INCLUDED REGION SIZE: 180

PRODUCT SIZE: 133, PAIR ANY COMPL: 4.00, PAIR 3' COMPL: 0.00

```
  1 AGGGGCATTCTACAAAACACCCAACCGGTCAAGGTCGCTGAGGCCAAGGAGAGATTGGGC
                                                >>>>>>>>>>>>>>

61 AACCGTCACAAACCAGAGAAGcCGAGGAGAcCTTTCAGCCAACGCCATGTGGGGTCCTGA
    >>>

121 GCAGGACCCACCGGAAGTTGGTGCAGCTGCCTAAAGACCGTCCTGGCTGAGAAGAAACAG
                                  <<<<<<<<<<<<<<<<<<<
```

104) Whole sequence ::: rs2838650-rs2838651

TGGCCCTGACCTGCCAGAGCTGTTGGCCTCCAGCTGGCGGGTAAAACCCACGGCCTTCTC

AGAACAGGTTTCTCAACACATGAGACAGAACACACCAGACTTCCaAGGGGAACACCTGGA

TGGAGCTGGTTACCCAGATcGTTCAACACCGAGGGGCAGCGGCTTGAGGGTCTTTCCACG

AAGGCTTGGATTAACAAGAGGAGCASRGGTCTCTCCAGGATGGGCCCA (SEQ ID NO: 301)

| OLIGO | start | len | tm | gc % | any | 3' | seq (SEQ ID NOs: 302, 303) |
|---|---|---|---|---|---|---|---|
| LEFT PRIMER | 79 | 20 | 54.89 | 50.00 | 4.00 | 1.00 | CATGAGACAGAACACACCAG |
| RIGHT PRIMER | 199 | 20 | 54.61 | 40.00 | 5.00 | 3.00 | TCTTGTTAATCCAAGCCTTC |

SEQUENCE SIZE: 228
INCLUDED REGION SIZE: 228

PRODUCT SIZE: 121, PAIR ANY COMPL: 4.00, PAIR 3' COMPL: 1.00

```
  1 TGGCCCTGACCTGCCAGAGCTGTTGGCCTCCAGCTGGCGGGTAAAACCCACGGCCTTCTC

61 AGAACAGGTTTCTCAACACATGAGACAGAACACACCAGACTTCCaAGGGGAACACCTGGA
                       >>>>>>>>>>>>>>>>>>>>

121 TGGAGCTGGTTACCCAGATcGTTCAACACCGAGGGGCAGCGGCTTGAGGGTCTTTCCACG
                                                              <

181 AAGGCTTGGATTAACAAGAGGAGCASRGGTCTCTCCAGGATGGGCCCA
    <<<<<<<<<<<<<<<<<<<
```

105) Whole sequence ::: rs2838654-rs1296489

CCACCCAGTGTCACGTCACGGCCCCGGCACGCCATCCACGGACCCTGGATGGAGCCCAGC

TGCCTCCaGGAGCGCAGTTTAACTACAAAGGAGCCCTGGCTGCCCGCCCCGCCCAGACGC

ACTGACCTGTTGTTCTCTGTGGCTGCTGATGGCCCaTCCCCAACCACTGGTGACTCTTCC

CTGGGGCCCCAAGCTCAGCCCCTAACCCCCTGTTGCTGGAAGT (SEQ ID NO: 304)

| OLIGO | start | len | tm | gc % | any | 3' | seq (SEQ ID NOs: 305, 306) |
|---|---|---|---|---|---|---|---|
| LEFT PRIMER | 37 | 18 | 62.56 | 66.67 | 5.00 | 2.00 | CACGGACCCTGGATGGAG |
| RIGHT PRIMER | 183 | 18 | 53.14 | 55.56 | 3.00 | 2.00 | CAGGGAAGAGTCACCAGT |

SEQUENCE SIZE: 223
INCLUDED REGION SIZE: 223

PRODUCT SIZE: 147, PAIR ANY COMPL: 5.00, PAIR 3' COMPL: 2.00

```
  1 CCACCCAGTGTCACGTCACGGCCCCGGCACGCCATCCACGGACCCTGGATGGAGCCCAGC
                                          >>>>>>>>>>>>>>>>>>
```

TABLE 2-continued

```
 61 TGCCTCCaGGAGCGCAGTTTAACTACAAAGGAGCCCTGGCTGCCCGCCCCGCCCAGACGC

121 ACTGACCTGTTGTTCTCTGTGGCTGCTGATGGCCCaTCCCCAACCACTGGTGACTCTTCC
                                                 <<<<<<<<<<<<<

181 CTGGGGCCCCAAGCTCAGCCCCTAACCCCCTGTTGCTGGAAGT
   <<<
```

106) Whole sequence ::: rs2838659-rs1108261

```
CAGAGGACTGGGCTGCGGGGTCAGGAATGGGCACACTTCCTAACTGCAGGACACTCTAAG

GGCTTTGGTCATGCACACgCAGCCAAGAGAAGGTGTCGCTGaCACACAGCCTTCCAGGAG

CGGACTTGGAGACCTCGCCAAGGACCAGGACTCCCCAGCACTCACACTCCCTTAGGCGCT

GAAGTC (SEQ ID NO: 307)
```

| OLIGO | start | len | tm | gc % | any | 3' | seq (SEQ ID NOs: 308, 309) |
|---|---|---|---|---|---|---|---|
| LEFT PRIMER | 53 | 20 | 55.48 | 45.00 | 4.00 | 2.00 | ACTCTAAGGGCTTTGGTCAT |
| RIGHT PRIMER | 175 | 20 | 56.02 | 55.00 | 3.00 | 1.00 | CTAAGGGAGTGTGAGTGCTG |

SEQUENCE SIZE: 186
INCLUDED REGION SIZE: 186

PRODUCT SIZE: 123, PAIR ANY COMPL: 4.00, PAIR 3' COMPL: 1.00

```
  1 CAGAGGACTGGGCTGCGGGGTCAGGAATGGGCACACTTCCTAACTGCAGGACACTCTAAG
                                                        >>>>>>>>

61 GGCTTTGGTCATGCACACgCAGCCAAGAGAAGGTGTCGCTGaCACACAGCCTTCCAGGAG
    >>>>>>>>>>>>

121 CGGACTTGGAGACCTCGCCAAGGACCAGGACTCCCCAGCACTCACACTCCCTTAGGCGCT
                                           <<<<<<<<<<<<<<<<<<<<

181 GAAGTC
```

107) Whole sequence ::: rs585587-rs585601

```
GAAGAGGACAACACGGGGCTGTCTGCAGAGCACCTGCCACGCGCCAGGCTCTGTGTCCAC

AAGCACGGCGGCTGCTCCCACATGACaGAGCTCGTGcGGCAGCTCCAGGACTGTCTGGTG

CCAGAGCCCCAGCTCTCCGCCAGCCCCAGGCCACTGTGCGAGGCCCTCAGTGAAGAGGGG

GCCGT (SEQ ID NO: 310)
```

| OLIGO | start | len | tm | gc % | any | 3' | seq (SEQ ID NOs: 311, 312) |
|---|---|---|---|---|---|---|---|
| LEFT PRIMER | 42 | 18 | 64.78 | 66.67 | 5.00 | 2.00 | CGCCAGGCTCTGTGTCCA |
| RIGHT PRIMER | 183 | 18 | 60.76 | 66.67 | 5.00 | 3.00 | GGCCCCTCTTCACTGAG |

SEQUENCE SIZE: 185
INCLUDED REGION SIZE: 185

PRODUCT SIZE: 142, PAIR ANY COMPL: 5.00, PAIR 3' COMPL: 3.00

```
  1 GAAGAGGACAACACGGGGCTGTCTGCAGAGCACCTGCCACGCGCCAGGCTCTGTGTCCAC
                                             >>>>>>>>>>>>>>>>>>

61 AAGCACGGCGGCTGCTCCCACATGACaGAGCTCGTGCGGCAGCTCCAGGACTGTCTGGTG

121 CCAGAGCCCCAGCTCTCCGCCAGCCCCAGGCCACTGTGCGAGGCCCTCAGTGAAGAGGGG
                                                <<<<<<<<<<<<<

181 GCCGT
   <<<
```

108) Whole sequence ::: rs9981033-rs4818998

```
TCTAAATAATGTTAATGATCAAATTTAGTCAGATCTCAATCTTCATATGTTAGTTGCCTT

CTTAaTAAATATTCTGTTTTCTTTATCGTTCTTTATTTGTATCTCcACCTTCATTTCTGA

TTAAATTAAGAAGTTTTGTCTCTTCCATTTAATAATTAATGTATTTAATAACC (SEQ ID NO: 313)
```

TABLE 2-continued

```
OLIGO          start  len  tm     gc %    any   3'    seq (SEQ ID NOs: 314, 315)
LEFT PRIMER    24     22   51.86  31.82   6.00  2.00  TTTAGTCAGATCTCAATCTTCA
RIGHT PRIMER   149    22   54.02  31.82   4.00  3.00  AATGGAAGAGACAAAACTTCTT
```

SEQUENCE SIZE: 173
INCLUDED REGION SIZE: 173

PRODUCT SIZE: 126, PAIR ANY COMPL: 5.00, PAIR 3' COMPL: 1.00

```
  1 TCTAAATAATGTTAATGATCAAATTTAGTCAGATCTCAATCTTCATATGTTAGTTGCCTT
                            >>>>>>>>>>>>>>>>>>>>>>

61 CTTAaTAAATATTCTGTTTTCTTTATCGTTCTTTATTTGTATCTCcACCTTCATTTCTGA

121 TTAAATTAAGAAGTTTTGTCTCTTCCATTTAATAATTAATGTATTTAATAACC
              <<<<<<<<<<<<<<<<<<<<<<
```

109) Whole sequence ::: rs2838802-rs2838803

CACACTCCACACTGGCCCCACGCGGGTGGCGAAGGACTCAGCCAGAGCCTGGCAGGATCC

TGGGGTGTCTaTTTCCAAGGAATGTTCTGGAAGAAACATACACACATACTTGTTTGCCAG

ATTTACCTGTGTGGTcTTCCAGATGAGAAGCAGCCTGTGTCACTCCATAAGGGAGAGTGC

GTGCAGCATTGAGA (SEQ ID NO: 316)

```
OLIGO          start  len  tm     gc %    any   3'    seq (SEQ ID NOs: 317, 318)
LEFT PRIMER    31     18   55.96  61.11   5.00  3.00  GAAGGACTCAGCCAGAGC
RIGHT PRIMER   177    20   55.20  50.00   7.00  3.00  CTCTCCCTTATGGAGTGACA
```

SEQUENCE SIZE: 194
INCLUDED REGION SIZE: 194

PRODUCT SIZE: 147, PAIR ANY COMPL: 4.00, PAIR 3' COMPL: 0.00

```
  1 CACACTCCACACTGGCCCCACGCGGGTGGCGAAGGACTCAGCCAGAGCCTGGCAGGATCC
                                    >>>>>>>>>>>>>>>>>>

61 TGGGGTGTCTaTTTCCAAGGAATGTTCTGGAAGAAACATACACACATACTTGTTTGCCAG

121 ATTTACCTGTGTGGTcTTCCAGATGAGAAGCAGCCTGTGTCACTCCATAAGGGAGAGTGC
                                    <<<<<<<<<<<<<<<<<<<<

181 GTGCAGCATTGAGA
```

110) Whole sequence ::: rs2183596-rs2150452

AAGAAACTCCCAAGGAACGCATTGTCCCAAGTTGCTGCACCAGTCAGTGTACATTCCCAC

AAaCAGTGCATGAGAGTTCCTGTTGCTTGTGAAATAAATGGTCAGCATTCAGTGTTGTCA

GCTTTTAAAATTTTCTCCTTTCTAGTGGGCATGTAATGGTcTCACATTATAGTTTTAATT

TGCATTTTCCTGGTGACATGTGATACGGAACCTTCCTCCCATGCT (SEQ ID NO: 319)

```
OLIGO          start  len  tm     gc %    any   3'    seq (SEQ ID NOs: 320, 321)
LEFT PRIMER    39     19   50.19  47.37   6.00  2.00  ACCAGTCAGTGTACATTCC
RIGHT PRIMER   190    19   50.12  26.32   4.00  0.00  GGAAAATGCAAATTAAAAC
```

SEQUENCE SIZE: 225
INCLUDED REGION SIZE: 225

PRODUCT SIZE: 152, PAIR ANY COMPL: 4.00, PAIR 3' COMPL: 1.00

```
  1 AAGAAACTCCCAAGGAACGCATTGTCCCAAGTTGCTGCACCAGTCAGTGTACATTCCCAC
                                            >>>>>>>>>>>>>>>>>>>

61 AAaCAGTGCATGAGAGTTCCTGTTGCTTGTGAAATAAATGGTCAGCATTCAGTGTTGTCA

121 GCTTTTAAAATTTTCTCCTTTCTAGTGGGCATGTAATGGTcTCACATTATAGTTTTAATT
                                                     <<<<<<<<

181 TGCATTTTCCTGGTGACATGTGATACGGAACCTTCCTCCCATGCT
       <<<<<<<<<<<
```

TABLE 2-continued

111) Whole sequence ::: rs4599218-rs9978646

GTGCAATTTAATTACAAACGCTTAAATGGGGAGGTCAGGGGCAGAGGGATGATGTCACAA

ACACACCCAcGTGTGCTTGGTGCAAAACAGTAAAACAAACAGCAAGAAGgTCCATGAAGG

AAAGATCGCCTCTGTCAGTGGGAGTAATGAGAGTGGCTGATGGACAGGTG (SEQ ID NO: 322)

```
OLIGO         start   len   tm      gc %    any    3'     seq (SEQ ID NOs: 323, 324)
LEFT PRIMER   19      20    61.86   55.00   4.00   1.00   CGCTTAAATGGGGAGGTCAG
RIGHT PRIMER  168     20    60.83   60.00   3.00   0.00   CCTGTCCATCAGCCACTCTC
```

SEQUENCE SIZE: 170
INCLUDED REGION SIZE: 170

PRODUCT SIZE: 150, PAIR ANY COMPL: 5.00, PAIR 3' COMPL: 2.00

```
  1 GTGCAATTTAATTACAAACGCTTAAATGGGGAGGTCAGGGGCAGAGGGATGATGTCACAA
                      >>>>>>>>>>>>>>>>>>>>

61 ACACACCCAcGTGTGCTTGGTGCAAAACAGTAAAACAAACAGCAAGAAGgTCCATGAAGG

121 AAAGATCGCCTCTGTCAGTGGGAGTAATGAGAGTGGCTGATGGACAGGTG
                           <<<<<<<<<<<<<<<<<<<<
```

112) Whole sequence ::: rs11702503-rs3827270

ACGCCAAGCAGGAGATGCCAGACACAGAGTCCATCCTGAGAGAGTCTGTTCCTGTCCAAG

CTCAGAAACACAGGAAGCcACCTGTGCTGTAGCAGCACaCGGAGATGCATCCTTTCTGGT

CCACCCCACGGCCCTCATTGCAGTCAGGGATCCTCTCCCAGAAAGTCCCTGCTGCCAGCC

CCTGCCCTT (SEQ ID NO: 325)

```
OLIGO         start   len   tm      gc %    any    3'     seq (SEQ ID NOs: 326, 327)
LEFT PRIMER   7       20    62.02   55.00   3.00   0.00   AGCAGGAGATGCCAGACACA
RIGHT PRIMER  125     20    63.37   55.00   5.00   4.00   GGTGGACCAGAAAGGATGCA
```

SEQUENCE SIZE: 189
INCLUDED REGION SIZE: 189

PRODUCT SIZE: 119, PAIR ANY COMPL: 3.00, PAIR 3' COMPL: 0.00

```
  1 ACGCCAAGCAGGAGATGCCAGACACAGAGTCCATCCTGAGAGAGTCTGTTCCTGTCCAAG
            >>>>>>>>>>>>>>>>>>>>

61 CTCAGAAACACAGGAAGCcACCTGTGCTGTAGCAGCACaCGGAGATGCATCCTTTCTGGT
                                             <<<<<<<<<<<<<<<

121 CCACCCCACGGCCCTCATTGCAGTCAGGGATCCTCTCCCAGAAAGTCCCTGCTGCCAGCC
        <<<<<

181 CCTGCCCTT
```

113) Whole sequence ::: rs2839084-rs9984302

CATGAGAAAGACTTTGTTCCCATGAGAACAACAAGAGAAACTCAAACAAAATTAAAATTG

TACTTTTCTAAAAGACcGGGGTGGGGGTCGTGGTCAGGCAGCaGCATGAAGAAAGCCTTG

AGAACTGAATTCCAGAAAGAAACAAGCATAGGCAAGAAAGAGAGATGACA (SEQ ID NO: 328)

```
OLIGO         start   len   tm      gc %    any    3'     seq (SEQ ID NOs: 329, 330)
LEFT PRIMER   19      22    59.21   40.91   4.00   0.00   CCCATGAGAACAACAAGAGAAA
RIGHT PRIMER  162     20    55.46   45.00   4.00   2.00   CTCTTTCTTGCCTATGCTTG
```

SEQUENCE SIZE: 170
INCLUDED REGION SIZE: 170

PRODUCT SIZE: 144, PAIR ANY COMPL: 5.00, PAIR 3' COMPL: 3.00

```
  1 CATGAGAAAGACTTTGTTCCCATGAGAACAACAAGAGAAACTCAAACAAAATTAAAATTG
                      >>>>>>>>>>>>>>>>>>>>>>

61 TACTTTTCTAAAAGACcGGGGTGGGGGTCGTGGTCAGGCAGCaGCATGAAGAAAGCCTTG
```

TABLE 2-continued

```
121AGAACTGAATTCCAGAAAGAAACAAGCATAGGCAAGAAAGAGAGATGACA
                <<<<<<<<<<<<<<<<<
```

114) Whole sequence ::: rs2249057-rs2249060

AAGATTTAGAACAGCTGAAGCAGCGAGAAAAAACCCAGCATGAGTCaGAACTGGAGCAAC

TGAGGATTTATTTTGAAAAGAAGTTAAGGGATGCTGAGAAAACTTACCAAGAAGACCTAA cCCTGTTACAGCAGAGGCTGCAGGGGGCGAGGGAAGATGCTCTTCTG (SEQ ID NO: 331)

| OLIGO | start | len | tm | gc % | any | 3' | seq (SEQ ID NOs: 332, 333) |
|---|---|---|---|---|---|---|---|
| LEFT PRIMER | 12 | 21 | 63.07 | 47.62 | 6.00 | 0.00 | CAGCTGAAGCAGCGAGAAAAA |
| RIGHT PRIMER | 146 | 19 | 66.33 | 68.42 | 6.00 | 3.00 | CCCCTGCAGCCTCTGCTGT |

SEQUENCE SIZE: 167
INCLUDED REGION SIZE: 167

PRODUCT SIZE: 135, PAIR ANY COMPL: 7.00, PAIR 3' COMPL: 1.00

```
  1AAGATTTAGAACAGCTGAAGCAGCGAGAAAAAACCCAGCATGAGTCaGAACTGGAGCAAC
              >>>>>>>>>>>>>>>>>>>>>

61TGAGGATTTATTTTGAAAAGAAGTTAAGGGATGCTGAGAAAACTTACCAAGAAGACCTAA

121cCCTGTTACAGCAGAGGCTGCAGGGGGCGAGGGAAGATGCTCTTCTG
             <<<<<<<<<<<<<<<<<<<
```

115) Whole sequence ::: rs2839226-rs2839227

GGGAAACTGACTTGGCTTTTGCAAGGGTCATTGCTTCCTGATGCATGTTTAACTGTCCTG

TGTTCACTTTGTTGCcGCAGGTTTTTAGAGGAACGTAAAGAGATCaCCGAGAAATTCAGT

GCGGAACAAGATGCCTTCCTGCAGGAGGCCCAGGAGCAGCATGCCCGTGAGCTG (SEQ ID NO: 334)

| OLIGO | start | len | tm | gc % | any | 3' | seq (SEQ ID NOs: 335, 336) |
|---|---|---|---|---|---|---|---|
| LEFT PRIMER | 1 | 22 | 64.29 | 50.00 | 3.00 | 2.00 | GGGAAACTGACTTGGCTTTTGC |
| RIGHT PRIMER | 135 | 20 | 64.63 | 55.00 | 3.00 | 2.00 | GGCATCTTGTTCCGCACTGA |

SEQUENCE SIZE: 174
INCLUDED REGION SIZE: 174

PRODUCT SIZE: 135, PAIR ANY COMPL: 4.00, PAIR 3' COMPL: 0.00

```
  1GGGAAACTGACTTGGCTTTTGCAAGGGTCATTGCTTCCTGATGCATGTTTAACTGTCCTG
    >>>>>>>>>>>>>>>>>>>>>>

61TGTTCACTTTGTTGCcGCAGGTTTTTAGAGGAACGTAAAGAGATCaCCGAGAAATTCAGT
                                                          <<<<<

121GCGGAACAAGATGCCTTCCTGCAGGAGGCCCAGGAGCAGCATGCCCGTGAGCTG
    <<<<<<<<<<<<<<<
```

116) Whole sequence ::: rs10854482-rs2839261

CCCTGCACACTGACCTGCATGCCCTCGTCACCTGCACTCTGCATGCTCACCATCTGACGG

ACTCCTGCGAcGGGCATGGGAAGGTCGCCGCCGCCGGCAGCCtTGCGAGCACTTTGGATG

TGTGCACCCGGCATGCCAGGCCCGAGTCAACAGACTGGCCGACCTTGGCGTCCTG (SEQ ID NO: 337)

| OLIGO | start | len | tm | gc % | any | 3' | seq (SEQ ID NOs: 338, 339) |
|---|---|---|---|---|---|---|---|
| LEFT PRIMER | 21 | 20 | 65.22 | 65.00 | 4.00 | 0.00 | GCCCTCGTCACCTGCACTCT |
| RIGHT PRIMER | 168 | 20 | 64.77 | 60.00 | 5.00 | 1.00 | CCAAGGTCGGCCAGTCTGTT |

SEQUENCE SIZE: 175
INCLUDED REGION SIZE: 175

PRODUCT SIZE: 148, PAIR ANY COMPL: 4.00, PAIR 3' COMPL: 0.00

```
  1CCCTGCACACTGACCTGCATGCCCTCGTCACCTGCACTCTGCATGCTCACCATCTGACGG
                      >>>>>>>>>>>>>>>>>>>>

61ACTCCTGCGAcGGGCATGGGAAGGTCGCCGCCGCCGGCAGCCtTGCGAGCACTTTGGATG
```

TABLE 2-continued

```
121 TGTGCACCCGGCATGCCAGGCCCGAGTCAACAGACTGGCCGACCTTGGCGTCCTG
       <<<<<<<<<<<<<<<<<<<<<<

117) Whole sequence ::: rs2032111-rs718496

TTTATTGCTGAGTGGTATTCCATTTTATGGGTCCATTATAGTTTATTTGTCCAGACACTT

CATGGAAaGACATCAGTGTTTCCtGTTTTTCAATCATAAATTGATGTTTAATTTTAAAAT

TTTGGAATTGTAGAAGAAATGCAATTCTTTTTTCC (SEQ ID NO: 340)

OLIGO         start    len    tm      gc %    any    3'     seq (SEQ ID NOs: 341, 342)

LEFT PRIMER   28       22     53.65   31.82   4.00   3.00   TGGGTCCATTATAGTTTATTTG
RIGHT PRIMER  143      22     57.46   31.82   4.00   2.00   TGCATTTCTTCTACAATTCCAA

SEQUENCE SIZE: 155
INCLUDED REGION SIZE: 155

PRODUCT SIZE: 116, PAIR ANY COMPL: 5.00, PAIR 3' COMPL: 3.00

1 TTTATTGCTGAGTGGTATTCCATTTTATGGGTCCATTATAGTTTATTTGTCCAGACACTT
                                 >>>>>>>>>>>>>>>>>>>>>>

61 CATGGAAaGACATCAGTGTTTCCtGTTTTTCAATCATAAATTGATGTTTAATTTTAAAAT

121 TTTGGAATTGTAGAAGAAATGCAATTCTTTTTTCC
        <<<<<<<<<<<<<<<<<<<<<<

118) Whole sequence ::: rs2070434-rs2070435

CTTTGGTGCAGAATCATGCTGCAGGCAAGGTGGGCCCACCTCCCTGGAATTTCATCCCCC cCGTCAGTTAAACCCATGGTGGTTTTATTTTCTAGGCCACCTGATCTGGGAGGACCACCT

CCAAGAAAAGCAGTCCTaTCGATGAACGGTCTAAGTTATGGTGTTATCAGAGTGGATACT

GAAGAAAAGTTGTCAGTCCTTACTGTTC (SEQ ID NO: 343)

OLIGO         start    len    tm      gc %    any    3'     seq (SEQ ID NOs: 344, 345)

LEFT PRIMER   33       20     66.57   60.00   4.00   3.00   GGCCCACCTCCCTGGAATTT
RIGHT PRIMER  176      22     54.26   40.91   4.00   0.00   TCCACTCTGATAACACCATAAC

SEQUENCE SIZE: 208
INCLUDED REGION SIZE: 208

PRODUCT SIZE: 144, PAIR ANY COMPL: 4.00, PAIR 3' COMPL: 1.00

1 CTTTGGTGCAGAATCATGCTGCAGGCAAGGTGGGCCCACCTCCCTGGAATTTCATCCCCC
                                     >>>>>>>>>>>>>>>>>>>>

61 cCGTCAGTTAAACCCATGGTGGTTTTATTTTCTAGGCCACCTGATCTGGGAGGACCACCT

121 CCAAGAAAAGCAGTCCTaTCGATGAACGGTCTAAGTTATGGTGTTATCAGAGTGGATACT
                                              <<<<<<<<<<<<<<<<<<<<<<

181 GAAGAAAAGTTGTCAGTCCTTACTGTTC
```

All publications, patents and patent applications cited herein are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of determining the presence or absence of a fetal chromosomal aneuploidy, comprising:
   providing a composition that comprises isolated or purified maternal and fetal nucleic acids molecules from a maternal sample;
   determining sets of tandem single nucleotide polymorphisms present in specific chromosomes;
   producing amplicons from the composition comprising the determined sets of tandem single nucleotide polymorphisms;
   identifying produced amplicons comprising at least 3 different haplotypes of at least one tandem single nucleotide polymorphism (SNP), wherein the single nucleotide polymorphisms in the tandem SNP are at most 250 basepairs apart, and wherein 2 of the 3 haplotypes are present in the maternal nucleic acids and wherein 1 of the 3 haplotypes is not present in the maternal nucleic acids;
   quantifying the amount of each of the identified amplicons produced from the composition and comprising the 3 different haplotypes;
   comparing the quantified amounts of each amplicon to one another;
   comparing the tandem SNPs present in the amplicons so as to identify the chromosomes from which the amplicons are produced;
   and
   determining whether the fetus has a chromosomal aneuploidy based on the compared quantified amounts of amplicons in the composition.

2. The method of claim 1, wherein the single nucleotide polymorphisms in the tandem SNP are at most 150 basepairs apart.

3. The method of claim 1, wherein the single nucleotide polymorphisms in the tandem SNP are at most 100 basepairs apart.

4. The method of claim 1, wherein the chromosomal aneuploidy is trisomy 13, trisomy 18 or trisomy 21.

5. The method of claim 1, wherein the produced amplicons comprise at least one of SEQ ID NOs: 1-357.

6. The method of claim 1, wherein the amplicons are quantified using sequencing.

7. The method of claim 1, wherein the amplicons are detected using constant denaturant capillary electrophoresis.

8. The method of claim 1, wherein the amplicons are produced using high-fidelity PCR.

9. The method of claim 8, further comprising:
   separating the amplicons by constant denaturant capillary electrophoresis (CDCE), wherein the amplicons comprising the 3 different haplotypes identified in the identifying step are resolved as 3 peaks in an electropherogram obtained from the CDCE separation, and
   wherein quantifying the amount of each of the amplicons comprising the 3 haplotypes comprises measuring peak areas of the 3 resolved peaks in the electropherogram, wherein the 3 resolved peak areas represent the amounts of amplicons.

* * * * *